United States Patent
Lauer et al.

(10) Patent No.: US 10,526,609 B2
(45) Date of Patent: Jan. 7, 2020

(54) PROTEIN EXPRESSION ENHANCER SEQUENCES AND USE THEREOF

(71) Applicant: ADURO BIOTECH, INC., Berkeley, CA (US)

(72) Inventors: Peter M. Lauer, Albany, CA (US); William G. Hanson, Walnut Creek, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 0 days.

(21) Appl. No.: 15/664,792

(22) Filed: Jul. 31, 2017

(65) Prior Publication Data

US 2018/0030457 A1 Feb. 1, 2018

Related U.S. Application Data

(60) Provisional application No. 62/369,663, filed on Aug. 1, 2016, provisional application No. 62/373,297, filed on Aug. 10, 2016.

(51) Int. Cl.

| C12N 15/67 | (2006.01) |
|---|---|
| A61K 39/395 | (2006.01) |
| C07K 14/47 | (2006.01) |
| C12N 15/86 | (2006.01) |
| A61K 48/00 | (2006.01) |
| A61K 39/00 | (2006.01) |

(52) U.S. Cl.
CPC ........ *C12N 15/67* (2013.01); *A61K 39/39558* (2013.01); *C07K 14/4748* (2013.01); *C12N 15/86* (2013.01); *A61K 48/00* (2013.01); *A61K 2039/5152* (2013.01); *C07K 2319/00* (2013.01); *C12N 2830/00* (2013.01)

(58) Field of Classification Search
None
See application file for complete search history.

(56) References Cited

U.S. PATENT DOCUMENTS

| 7,041,814 B1 * | 5/2006 | Weinstock | C07K 14/265 435/252.3 |
|---|---|---|---|
| 2004/0029129 A1 * | 2/2004 | Wang | C07K 14/195 435/6.18 |
| 2009/0183270 A1 | 7/2009 | Adams et al. | |

FOREIGN PATENT DOCUMENTS

| WO | 2008034648 A1 | 3/2008 |
|---|---|---|
| WO | 2011061656 A1 | 5/2011 |

OTHER PUBLICATIONS

Sequence Alignment of SEQ ID No. 13826 from U.S. Pat. No. 8,344,211 to Instant SEQ ID No. 1. Search conducted on Jan. 3, 2019, 3 pages. (Year: 2019).*
Sequence Alignment of SEQ ID No. 3752 from US Patent Application Publication No. 2009183270 to Instant SEQ ID No. 1. Search conducted on Jan. 3, 2019, 3 pages. (Year: 2019).*
Sequence Alignment of SEQ ID No. 90247 from U.S. Pat. No. 8,344,211 to Instant SEQ ID No. 1. Search conducted on Jan. 3, 2019, 1 page. (Year: 2019).*
Sequence Alignment of SEQ ID No. 62686 from US Patent Application Publication No. 20040029129 to Instant SEQ ID No. 37. Search conducted on Aug. 13, 2019. 4 pages. (Year: 2019).*
Sequence Alignment of SEQ ID No. 8523 from U.S. Pat. No. 7,041,814 to Instant SEQ ID No. 1. Search conducted on Aug. 13, 2019, 1 page. (Year: 2019).*
International Search Report and Written Opinion issued in PCT/US2017/044699 dated Dec. 26, 2017—14 pages.

* cited by examiner

*Primary Examiner* — Channing S Mahatan
(74) *Attorney, Agent, or Firm* — Acuity Law Group, PC; Michael A. Whittaker

(57) ABSTRACT

The present invention provides nucleic acid and protein sequences that enhance the expression of fusion proteins by host cells, and in particular bacterial species, together with methods use thereof. While described hereinafter in terms of expression of fusion proteins by *Listeria monocytogenes*, the present invention is applicable to expression of fusion proteins generally.

26 Claims, 19 Drawing Sheets

Specification includes a Sequence Listing.

PROTEIN EXPRESSION ENHANCER SEQUENCES AND USE THEREOF

The present application claims priority to U.S. Provisional Patent Application No. 62/369,663, filed Aug. 1, 2016, and to U.S. Provisional Patent Application No. 62/373,297, filed Aug. 10, 2016, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Jul. 27, 2017, is named ADR_1009_UT_SeqListing.txt and is 88 kilobytes in size.

BACKGROUND OF THE INVENTION

The following discussion of the background of the invention is merely provided to aid the reader in understanding the invention and is not admitted to describe or constitute prior art to the present invention.

Pathogenic organisms are, by definition, capable of causing disease in an infected host. For clinical use of such organisms, attenuated vaccine strains are often created which exhibit reduced or eliminated virulence, but which still retain sufficient viability to stimulate a desired immune response against the pathogen or heterologous antigen(s) of interest. Attenuated vector platforms have been demonstrated to elicit protective responses specific for encoded heterologous antigens in a number of experimental models, including infectious and malignant diseases.

Although most attenuated vaccine vectors are viral, bacterial vaccine vector platforms have been developed for both prophylactic and therapeutic applications. Attenuated strains of many otherwise pathogenic bacteria are now available and the ease of manipulation for generating recombinant strains provides a means for using bacteria as efficacious delivery vehicles for a number of foreign proteins such as antigens associated with infectious diseases and cancer. Live attenuated bacterial vaccine strains have been developed from, inter alia, *Listeria, Escherichia, Salmonella, Shigella, Lactobacillus*, and *Yersinia* species.

Regulating the level of heterologous antigen expression can have a significant impact on the immunogenicity of the vaccine. In bacterial vaccine vectors, the heterologous gene encoding the vaccine antigen can be either integrated into the bacterial chromosome or expressed from a plasmid. Chromosomal integration allows maximum genetic stability. However, chromosomal integration usually results in a single copy of heterologous antigen per bacterium, and it is a challenge to ensure that sufficient antigen is expressed to confer protective immunity. In plasmid-based expression, spontaneous loss of plasmid can result in plasmid-less bacteria rapidly outgrowing plasmid-bearing bacteria and becoming the dominant population in tissues.

There remains a need in the art to provide systems and methods to provide bacterial vaccine strains with advantageous expression levels of heterologous antigens for use in the treatment or prevention of diseases.

BRIEF SUMMARY OF THE INVENTION

The present invention provides nucleic acid and protein sequences which enhance the expression of fusion proteins by host cells, and in particular bacterial species, together with methods of use thereof. While described hereinafter in terms of expression of fusion proteins by *Listeria monocytogenes*, the present invention is applicable to expression of fusion proteins generally.

In a first aspect, the present invention relates to fusion proteins, to nucleic acid molecules encoding the fusion proteins, and to methods of expressing the fusion proteins from the nucleic acid molecules, wherein the fusion proteins have the following structure:

A-(B)$n$-C or A-C-(B)$n$, where:

A is a first polypeptide sequence comprising an amino acid sequence of a secretory signal sequence;
Each B is independently a second polypeptide, the sequence of which comprises ESNQSVEDKHNEFMLTEY (SEQ ID NO: 1) or PASRAVDDHHAQFLLSEK (SEQ ID NO: 37) or a sequence having at least 90% identity or homology thereto, or a sequence having 1-5 conservative amino acid substitutions thereof; and
C is a third polypeptide sequence comprising an amino acid sequence of a polypeptide of interest, such as an antigenic sequence; and
n is a number between 1 and 10, and preferably between 2 and 5.

In some embodiments of the first aspect, A is linked to (B)n or C, and (B)n is linked to C with a peptide bond, or each linkage is independently one or more amino acids. In some embodiments, wherein the fusion protein is A-(B)n-C, the carboxy terminus of A is linked to the amino terminus of (B)n with a peptide bond, or with one or more amino acids, e.g. 1-100, 1-50, 1-20, 1-10, 1-9, 1-8, 1-7, 1-6, 1-5, 1-4, 1-3, 1-2 or 1 amino acids, and the carboxy terminus of (B)n is linked to the amino terminus of C with a peptide bond, or with one or more amino acids, e.g. 1-100, 1-50, 1-20, 1-10, 1-9, 1-8, 1-7, 1-6, 1-5, 1-4, 1-3, 1-2 or 1 amino acids. In some embodiments, wherein the fusion protein is A-C-(B)n, the carboxy terminus of A is linked to the amino terminus of C with a peptide bond, or with one or more amino acids, e.g. 1-100, 1-50, 1-20, 1-10, 1-9, 1-8, 1-7, 1-6, 1-5, 1-4, 1-3, 1-2 or 1 amino acids, and the carboxy terminus of C is linked to the amino terminus of (B)n with a peptide bond, or with one or more amino acids, e.g. 1-100, 1-50, 1-20, 1-10, 1-9, 1-8, 1-7, 1-6, 1-5, 1-4, 1-3, 1-2 or 1 amino acids.

In some embodiments of the first aspect, n is 1, 2, 3, 4, or 5, preferably 5, and each B further comprises an independently selected cleaver amino acid sequence linked to each of the amino terminus and carboxy terminus of each B (e.g., SEQ ID NO: 1 or SEQ ID NO: 37). By way of example, a cleaver amino acid sequence linked to the carboxy terminus (Cv1') of the first B (B1) is linked to the cleaver sequence linked to the amino terminus (Cv2) of the second B (B2) such that the linkage is -B1-Cv1'-Cv2-B2-, and so on. Thus, for example, (B)n where n=3 can be represented as Cv1-B1-Cv1'-Cv2-B2-Cv2'-Cv3-B3-Cv3', where Cv1, Cv2, and Cv3 represent a cleaver amino acid sequence linked via its carboxy terminus to the amino terminus of B1, B2, and B3, respectively and Cv1', Cv2', and Cv3' represent a cleaver amino acid sequence linked via its amino terminus to the carboxy terminus of B1, B2, and B3, respectively, wherein e.g. the carboxy terminus of Cv1' is linked to the amino terminus of Cv2. Thus, when the fusion protein is A-(B)n-C, the amino terminus of Cv1 is linked to the carboxy terminus of A, and the carboxy terminus of Cvn' (n representing the number of enhancer sequences B, i.e. the carboxy terminal sequence of B) is linked to the amino terminus of C, and when the fusion protein is A-C-(B)n, the amino terminus of Cv1 is linked to the carboxy terminus of C, and the carboxy terminus of Cvn' is the carboxy terminus of the fusion protein, or may include an additional one or more amino acids at the carboxy terminus of the fusion protein, e.g. 1-100, 1-50, 1-20, 1-10, 1-9, 1-8, 1-7, 1-6, 1-5, 1-4, 1-3, 1-2 or 1 amino acids. Each B1, B2 . . . Bn is independently SEQ ID NO: 1 or SEQ ID NO: 37, or a sequence having at least 90% identity or homology thereto, or a sequence having 1-5 conservative amino acid substitutions thereof, and each Cv1, Cv1', Cv2, Cv2' . . . Cvn, Cvn' is independently selected from the group consisting of ADGSVK (SEQ ID NO: 2), ASKVA (SEQ ID NO: 3), LSKVL (SEQ ID NO: 4), ASKVL (SEQ ID NO: 5), GDGSIK (SEQ ID NO: 6), ADGSV (SEQ ID NO: 7), LAKSL (SEQ ID NO: 8), ADLAVK (SEQ ID NO: 9), ASVVA (SEQ ID NO: 10), GIGSIA (SEQ ID NO: 11), GVEKI (SEQ ID NO: 12), NAANKG (SEQ ID NO: 13), DGSKKA (SEQ ID NO: 14), GDGNKK (SEQ ID NO: 15), KLSKVL (SEQ ID NO: 75), and GDGNK (SEQ ID NO: 76). In some embodiments, each Cv1, Cv1', Cv2, Cv2' . . . Cvn, Cvn' is independently selected from the group consisting of SEQ ID NO: 2, SEQ ID NO: 3, SEQ ID NO: 4, SEQ ID NO: 5, and SEQ ID NO: 6. In some embodiments, each Cv1, Cv2 . . . Cvn is independently SEQ ID NO: 3, SEQ ID NO: 4, or SEQ ID NO: 5 and each Cv1', Cv2' . . . Cvn' is independently SEQ ID NO: 2 or SEQ ID NO: 6. In some embodiments, each carboxy terminus of Cv1', Cv2' . . . Cv(n−1)' is linked to each amino terminus of Cv2, Cv3, . . . Cvn, respectively, independently with a peptide bond, or one or more amino acids, e.g. 1-100, 1-50, 1-20, 1-10, 1-9, 1-8, 1-7, 1-6, 1-5, 1-4, 1-3, 1-2 or 1 amino acids. In some embodiments, each carboxy terminus of Cv1', Cv2' . . . Cv(n−1)' is linked to each amino terminus of Cv2, Cv3, . . . Cvn, respectively, independently with a peptide bond, or 1, 2, 3, 4 or 5 amino acids. In some embodiments, each carboxy terminus of Cv1', Cv2' . . . Cv(n−1)' is linked to each amino terminus of Cv2, Cv3, . . . Cvn, respectively, independently with a peptide bond, or 1, 2 or 3 amino acids. In a preferred embodiment, the amino terminus of each Cv1', Cv2' . . . Cvn' is linked to the carboxy terminus of B1, B2 . . . Bn, respectively with the three amino acid sequence GSC. In some embodiments, each B1, B2, . . . Bn is SEQ ID NO: 1, or a sequence having at least 90% identity or homology thereto, or a sequence having 1-5 conservative amino acid substitutions thereof. In some embodiments, each B1, B2, . . . Bn is SEQ ID NO: 37, or a sequence having at least 90% identity or homology thereto, or a sequence having 1-5 conservative amino acid substitutions thereof. In some embodiments, linked to, as used in this paragraph, unless indicated otherwise, is a peptide bond, or linkage with one or more amino acids, e.g. 1-100, 1-50, 1-20, 1-10, 1-9, 1-8, 1-7, 1-6, 1-5, 1-4, 1-3, 1-2 or 1 amino acids.

In some embodiments of the first aspect, the third polypeptide sequence C comprises more than one independent antigenic sequences. In some embodiments C comprises one or more independent antigenic sequences, e.g. 1-50, 1-25, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 or 1 independent antigenic sequences. In some embodiments, each C further comprises an independently selected cleaver amino acid sequence linked to each of the amino terminus and carboxy terminus of each of the one or more antigenic sequences. Thus, for example, where C comprises 3 antigenic sequences, C can be represented as Cv1-C1-Cv1'-Cv2-C2-Cv2'-Cv3-C3-Cv3', where Cv1, Cv2, and Cv3 represent a cleaver amino acid sequence linked via its carboxy terminus to the amino terminus of C1, C2, and C3, respectively and Cv1', Cv2', and Cv3' represent a cleaver amino acid sequence linked via its amino terminus to the carboxy terminus of C1, C2, and C3, respectively, wherein e.g. the carboxy terminus of Cv1' is linked to the amino terminus of Cv2. In some embodiments, each Cv1, Cv1', Cv2, Cv2' . . . Cvx, Cvx' (where x represents the total number of antigenic sequences) is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76. In some embodiments, each Cv1, Cv1', Cv2, Cv2' . . . Cvx, Cvx' is independently selected from the group consisting of SEQ ID NO: 2, SEQ ID NO: 4, SEQ ID NO: 7, SEQ ID NO: 14, SEQ ID NO: 15, SEQ ID NO: 75 and SEQ ID NO: 76. In some embodiments, each Cv1, Cv2 . . . Cvx is independently SEQ ID NO: 4, SEQ ID NO: 14, or SEQ ID NO: 75 and each Cv1', Cv2' . . . Cvx' is independently SEQ ID NO: 2, SEQ ID NO: 7, SEQ ID NO: 15, or SEQ ID NO: 76. In some embodiments, each carboxy terminus of Cv1', Cv2' . . . Cv(x−1)' is linked to each amino terminus of Cv2, Cv3, . . . Cvx, respectively, independently with a peptide bond, or one or more amino acids, e.g. 1-100, 1-50, 1-20, 1-10, 1-9, 1-8, 1-7, 1-6, 1-5, 1-4, 1-3, 1-2 or 1 amino acids. In some embodiments, each carboxy terminus of Cv1', Cv2' . . . Cv(x−1)' is linked to each amino terminus of Cv2, Cv3, . . . Cvx, respectively, independently with a peptide bond, or by 1, 2, 3, 4 or 5 amino acids. In some embodiments, each carboxy terminus of Cv1', Cv2' . . . Cv(x−1)' is linked to each amino terminus of Cv2, Cv3, . . . Cvx, respectively, independently with a peptide bond, or by 1, 2, or 3 amino acids. In some embodiments, each antigenic sequence within C is independently 10-1,000, 10-500, 10-400, 10-300, 10-200, 10-100, 10-90, 10-80, 10-70, 10-60, 10-50, 10-40, or 10-30 amino acids in length.

In some embodiments, the fusion protein A-(B)n-C or A-C-(B)n is less than 3,000 amino acids, less than 2,000 amino acids, between 200 and 3,000 amino acids, between 200 and 2,000 amino acids, between 300 and 2,000 amino acids, between 300 and 1,500 amino acids or between 300 and 1,000 amino acids.

In a second aspect of the invention, the invention relates to nucleic acid molecules that encode a fusion protein, wherein the fusion protein comprises (i) a first amino acid sequence comprising one or more copies of an enhancer amino acid sequence, each enhancer amino acid sequence independently selected from the group consisting of ESNQSVEDKHNEFMLTEY (SEQ ID NO: 1) and PASRAVDDHHAQFLLSEK (SEQ ID NO: 37), or a sequence having at least 90% identity or homology thereto, or a sequence having 1-5 conservative amino acid substitutions thereof, and (ii) a second amino acid sequence encoding a polypeptide of interest. In some embodiments, the second amino acid sequence is linked to the amino or carboxyl terminus of the first amino acid sequence. In some embodiments, the polypeptide of interest comprises one or more independent antigenic sequences. In some embodiments, the second amino acid sequence comprises one or more cleaver amino acid sequences, wherein each cleaver sequence is independently selected and linked to at least one of the one or more independent antigenic sequences. In some embodiments, each independent antigenic sequence is linked to an independently selected cleaver sequence at its amino terminus and an independently selected cleaver sequence at its carboxy terminus. In some embodiments, the one or more copies of the enhancer amino acid sequence is one or more copies of SEQ ID NO: 1. In some embodiments, the one or more copies of the enhancer amino acid sequence is one or more copies of SEQ ID NO: 37. In some embodiments, the first amino acid sequence comprises 1 copy, 2 copies, 3 copies, 4 copies, or 5 copies of SEQ ID NO: 1. In some embodiments, the first amino acid sequence comprises 1 copy, 2 copies, 3 copies, 4 copies, or 5 copies of SEQ ID NO: 37. In a preferred embodiment, the first amino acid comprises 5 copies of SEQ ID NO: 1 or 5 copies of SEQ ID NO: 37, more preferably 5 copies of SEQ ID NO: 1.

In some embodiments of the second aspect, the one or more copies of the enhancer amino acid sequence is one or more copies of SEQ ID NO: 1. In some embodiments, the one or more copies of the enhancer amino acid sequence is one or more copies of SEQ ID NO: 37. In some embodiments, the first amino acid sequence comprises 1-5 copies, 2-5 copies, 3-5 copies, 4-5 copies, preferably 5 copies of the enhancer amino acid sequence. In some embodiments the first amino acid sequence comprises 1 copy, 2 copies, 3 copies, 4 copies, or 5 copies of SEQ ID NO: 1. In some embodiments, the first amino acid sequence comprises 1 copy, 2 copies, 3 copies, 4 copies, or 5 copies of SEQ ID NO: 37. In a preferred embodiment, the first amino acid comprises 5 copies of SEQ ID NO: 1 or 5 copies of SEQ ID NO: 37, more preferably 5 copies of SEQ ID NO: 1.

In some embodiments of the second aspect, each copy of the enhancer amino acid sequence is linked to the next copy of the enhancer amino acid sequence by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, the first amino acid sequence is linked to the second amino acid sequence by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, the fusion protein comprises an in frame secretory signal sequence. In some embodiments, the carboxy terminus of said secretory signal sequence is linked to the amino terminus of the first amino acid sequence, and the carboxy terminus of the first amino acid sequence is linked to the amino terminus of the second amino acid sequence. In some embodiments, the carboxy terminus of said secretory signal sequence is linked to the amino terminus of the second amino acid sequence, and the carboxy terminus of the second amino acid sequence is linked to the amino terminus of the first amino acid sequence. In these embodiments, the carboxy terminus of the secretory signal sequence is linked to the amino terminus of the first or second amino acid sequence by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids, and the first amino acid sequence is linked to the second amino acid sequence by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, the secretory signal sequence is a *Listeria monocytogenes* signal sequence, in some embodiments the ActA signal sequence. In some embodiments, the fusion protein of the present invention comprise an in-frame ActA signal sequence selected from the group consisting of SEQ ID NO: 25, SEQ ID NO: 26, SEQ ID NO: 27, and SEQ ID NO: 28, or an amino acid sequence having at least 90% sequence identity to said sequence.

In certain embodiments of the second aspect, the first amino acid sequence comprises one or more cleaver amino acid sequences, wherein each cleaver sequence is independently selected and linked to at least one of the one or more enhancer amino acid sequences. In some embodiments, each enhancer amino acid sequence is linked to an independently selected cleaver sequence at its amino terminus and an independently selected cleaver sequence at its carboxy terminus. In some embodiments, each of the one or more cleaver sequences is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76. In some embodiments, each of the one or more cleaver sequences is independently selected from the group consisting of SEQ ID NO: 2, SEQ ID NO: 3, SEQ ID NO: 4, SEQ ID NO: 5, and SEQ ID NO: 6. In some embodiments, the amino terminus of each enhancer sequence is linked to the carboxy terminus of the cleaver sequence selected from the group consisting of SEQ ID NO: 3, SEQ ID NO: 4 and SEQ ID NO: 5, and the carboxy terminus of each enhancer sequence is linked to the amino terminus of the cleaver sequence selected from the group consisting of SEQ ID NO: 2 and SEQ ID NO: 6. In some embodiments, within a fusion protein of the invention, the amino terminus of the enhancer sequence is linked to the carboxy terminus of SEQ ID NO: 4 or SEQ ID NO: 5 and the carboxy terminus of the enhancer sequence is linked to the amino terminus of SEQ ID NO: 2; or the amino terminus of the enhancer sequence is linked to the carboxy terminus of SEQ ID NO: 3 and the carboxy terminus of the enhancer sequence is linked to the amino terminus of SEQ ID NO: 6. In some embodiments, each cleaver sequence linked to an enhancer sequence is linked by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, each cleaver sequence linked to an enhancer sequence is linked by a peptide bond, or by 1, 2, 3, 4 or 5 amino acids. In some embodiments, each cleaver sequence linked to an enhancer sequence is linked by a peptide bond, or by 1, 2 or 3 amino acids. In some embodiments, each cleaver sequence linked by its amino terminus to the carboxy terminus of the enhancer sequence is linked by its carboxy terminus to the adjacent cleaver sequence (i.e. the cleaver sequence linked by its carboxy terminus to the next enhancer sequence). In some embodiments, each cleaver sequence linked by its carboxy terminus to the amino terminus of the next cleaver sequence is linked by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, each cleaver sequence linked by its carboxy terminus to the amino terminus of the next cleaver sequence is linked by a peptide bond, or by 1, 2, 3, 4 or 5 amino acids. In some embodiments, each cleaver sequence linked by its carboxy terminus to the amino terminus of the next cleaver sequence is linked by a peptide bond, or by 1, 2 or 3 amino acids.

In some embodiments of the second aspect, the second amino acid sequence comprises more than one independent antigenic sequence. In some embodiments the second amino acid sequence comprises one or more independent antigenic sequences, e.g. 1-50, 1-25, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 or 1 independent antigenic sequences. In some embodiments, the second amino acid sequence comprises one or more cleaver amino acid sequences, wherein each cleaver sequence is independently selected and linked to at least one of the one or more antigenic sequences. In some embodiments, each one or more independent antigenic sequence is linked to an independently selected cleaver sequence at its amino terminus and an independently selected cleaver sequence at its carboxy terminus. In some embodiments, each of the one or more cleaver sequences is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76. In some embodiments, each of the one or more cleaver sequences is independently selected from the group consisting of SEQ ID NO: 2, SEQ ID NO: 4, SEQ ID NO: 7, SEQ ID NO: 14, SEQ ID NO: 15, SEQ ID NO: 75, and SEQ ID NO: 76. In some embodiments, the amino terminus of each antigenic sequence is linked to the carboxy terminus of the cleaver sequence selected from the group consisting of SEQ ID NO: 4, SEQ ID NO: 14 and SEQ ID NO: 75, and the carboxy terminus of each antigenic sequence is linked to the amino terminus of the cleaver sequence selected from the group consisting of SEQ ID NO: 2, SEQ ID NO: 7, SEQ ID NO: 15 and SEQ ID NO: 76. In some embodiments, within a fusion protein of the invention, the amino terminus of the antigenic sequence is linked to the carboxy terminus of SEQ ID NO: 4 and the carboxy terminus of the antigenic sequence is linked to the amino terminus of SEQ ID NO: 7; or the amino terminus of the antigenic sequence is linked to the carboxy terminus of SEQ ID NO: 14 and the carboxy terminus of the antigenic sequence is linked to the amino terminus of SEQ ID NO: 2, SEQ ID NO: 15 or SEQ ID NO: 76; or the amino terminus of the antigenic sequence is linked to the carboxy terminus of SEQ ID NO: 75 and the carboxy terminus of the antigenic sequence is linked to the amino terminus of SEQ ID NO: 2 or SEQ ID NO: 76. In some embodiments, each cleaver sequence linked to an antigenic sequence is linked by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, each cleaver sequence linked to an antigenic sequence is linked by a peptide bond, or by 1, 2, 3, 4 or 5 amino acids. In some embodiments, each cleaver sequence linked to an antigenic sequence is linked by a peptide bond, or by 1, 2 or 3 amino acids. In some embodiments, each cleaver sequence linked by its amino terminus to the carboxy terminus of the antigenic sequence is linked by its carboxy terminus to the adjacent cleaver sequence (i.e. the cleaver sequence linked by its carboxy terminus to the next antigenic sequence). In some embodiments, each cleaver sequence linked by its carboxy terminus to the amino terminus of the next cleaver sequence is linked by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, each cleaver sequence linked by its carboxy terminus to the amino terminus of the next cleaver sequence is linked by a peptide bond, or by 1, 2, 3, 4 or 5 amino acids. In some embodiments, each cleaver sequence linked by its carboxy terminus to the amino terminus of the next cleaver sequence is linked by a peptide bond, or by 1, 2 or 3 amino acids. In some embodiments, each antigenic sequence within the second amino acid is independently 10-1,000, 10-500, 10-400, 10-300, 10-200, 10-100, 10-90, 10-80, 10-70, 10-60, 10-50, 10-40, or 10-30 amino acids in length.

In some embodiments of the second aspect, the fusion protein of the invention comprises a secretory signal sequence, wherein the amino terminus of the secretory sequence is linked to the carboxy terminus of the first amino acid, and the amino terminus of the first amino acid is linked to the carboxy terminus of the second amino acid. In some embodiments, the fusion protein of the invention comprises a secretory signal sequence, wherein the amino terminus of the secretory sequence is linked to the carboxy terminus of the first amino acid by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids, and the amino terminus of the first amino acid is linked to the carboxy terminus of the second amino acid by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, the fusion protein of the invention comprises a secretory signal sequence, wherein the amino terminus of the secretory sequence is linked to the carboxy terminus of the first amino acid by a peptide bond, or by 1, 2, 3, 4 or 5 amino acids, and the amino terminus of the first amino acid is linked to the carboxy terminus of the second amino acid by a peptide bond, or by 1, 2, 3, 4 or 5 amino acids. In some embodiments, the fusion protein of the invention comprises a secretory signal sequence, wherein the amino terminus of the secretory sequence is linked to the carboxy terminus of the first amino acid by a peptide bond, or by 1, 2 or 3 amino acids, and the amino terminus of the first amino acid is linked to the carboxy terminus of the second amino acid by a peptide bond, or by 1, 2 or 3 amino acids.

In some embodiments of the second aspect, the fusion protein of the invention comprises a secretory signal sequence, wherein the amino terminus of the secretory sequence is linked to the carboxy terminus of the second amino acid, and the amino terminus of the second amino acid is linked to the carboxy terminus of the first amino acid. In some embodiments, the fusion protein of the invention comprises a secretory signal sequence, wherein the amino terminus of the secretory sequence is linked to the carboxy terminus of the second amino acid by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids, and the amino terminus of the second amino acid is linked to the carboxy terminus of the first amino acid by a peptide bond, or by one or more amino acids, e.g. 1-100, 1-50, 1-20, 1-10, 1-9, 1-8, 1-7, 1-6, 1-5, 1-4, 1-3, 1-2 or 1 amino acids. In some embodiments, the fusion protein of the invention comprises a secretory signal sequence, wherein the amino terminus of the secretory sequence is linked to the carboxy terminus of the second amino acid by a peptide bond, or by 1, 2, 3, 4 or 5 amino acids, and the amino terminus of the second amino acid is linked to the carboxy terminus of the first amino acid by a peptide bond, or by 1, 2, 3, 4 or 5 amino acids. In some embodiments, the fusion protein of the invention comprises a secretory signal sequence, wherein the amino terminus of the secretory sequence is linked to the carboxy terminus of the second amino acid by a peptide bond, or by 1, 2 or 3 amino acids, and the amino terminus of the second amino acid is linked to the carboxy terminus of the first amino acid by a peptide bond, or by 1, 2 or 3 amino acids.

In some embodiments of the second aspect, the fusion protein is less than 3,000 amino acids, less than 2,000 amino acids, between 200 and 3,000 amino acids, between 200 and 2,000 amino acids, between 300 and 2,000 amino acids, between 300 and 1,500 amino acids or between 300 and 1,000 amino acids.

In related third aspect, the present invention relates to methods of expressing a polypeptide of interest from a host cell, comprising: introducing into the host cell an expression construct comprising a nucleic acid sequence that encodes a fusion protein, wherein the fusion protein is as described in the first and second aspects of the invention, including all embodiments thereof.

In some embodiments of the third aspect, the fusion protein comprises (i) a first amino acid sequence comprising one or more copies of an enhancer amino acid sequence, each enhancer amino acid sequence independently selected from the group consisting of ESNQSVEDKHNEFMLTEY (SEQ ID NO: 1) and PASRAVDDHHAQFLLSEK (SEQ ID NO: 37), or a sequence having at least 90% identity or homology thereto, or a sequence having 1-5 conservative amino acid substitutions thereof, wherein each copy is optionally flanked at each end by an amino acid sequence comprising a cleaver amino acid sequence as described hereinafter, and (ii) a second amino acid sequence of interest linked to the amino or carboxyl terminus of the first amino acid sequence, wherein the fusion protein is operably linked to one or more regulatory elements that mediate expression, and optionally secretion, of the fusion protein in the host cell.

In yet another related aspect, the present invention relates to a composition comprising a host cell that comprises a nucleic acid molecule of the present invention, wherein the host cell expresses, and optionally secretes, the fusion protein.

In certain embodiments, these nucleic acid molecules can comprise one or more regulatory elements that mediate expression of the fusion protein in a host cell. Such a nucleic acid molecule is referred to herein as a "fusion protein expression construct." The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements also include those that are inducible.

By way of example only, expression of genes under the actA promoter of *Listeria* is dependent upon a regulatory factor known as PrfA for transcriptional activation. Relative to broth-grown *Listeria*, gene expression under actA/PrfA regulation is induced approximately 200-fold when *Listeria* is present in host cells. Thus, in certain embodiments the regulatory sequences comprise a *Listeria monocytogenes* promoter that is PrfA-dependent. PrfA-dependent promoters may be selected from the group consisting of the inlA promoter, the inlB promoter, the inlC promoter, the hpt promoter, the hly promoter, the plcA promoter, the mpl promoter, and the actA promoter. Similar systems to induce gene expression in host organisms for other bacterial species are described hereinafter.

As noted above, the nucleic acid molecules of the present invention comprise a first amino acid sequence comprising one or more copies of an enhancer amino acid sequence, wherein each enhancer amino acid sequence is independently selected from the group consisting of ESNQSVEDKHNEFMLTEY (SEQ ID NO: 1) and PASRAVDDHHAQFLLSEK (SEQ ID NO: 37), or a sequence having at least 90% identity or homology thereto, or a sequence having 1-5 conservative amino acid substitutions thereof. In various embodiments, the first amino acid sequence comprises 2, 3, 4, 5, or more copies of the enhancer amino acid sequence arranged in a single contiguous array, and the second amino acid sequence encoding the polypeptide of interest is linked either preceding or following the first amino acid sequence.

In various embodiments, the first amino acid sequence is ASKVLESNQSVEDKHNEFMLTEYGSCADGSVK (SEQ ID NO: 31); or the first amino acid sequence is ASKVLPASRAVDDHHAQFLLSEKGSCADGSVK (SEQ ID NO: 29); or the first amino acid sequence is ASKVLESNQSVEDKHNEFMLTEYGSCADGSVKTSASKVAESNQSVEDKHNEFMLTEYG SCGDGSIK (SEQ ID NO: 69); or the first amino acid sequence is ASKVLPASRAVDDHHAQFLLSEKGSCADGSVKTSASKVAPASRAVDDHHAQFLLSEKG SCGDGSIK (SEQ ID NO: 70); or the first amino acid sequence is ASKVLESNQSVEDKHNEFMLTEYGSCADGSVKTSASKVAESNQSVEDKHNEFMLTEYG SCGDGSIKLSKVLESNQSVEDKHNEFMLTEYGSCADGSVK (SEQ ID NO: 71); or the first amino acid sequence is ASKVLPASRAVDDHHAQFLLSEKGSCADGSVKTSASKVAPASRAVDDHHAQFLLSEKG SCGDGSIKLSKVLPASRAVDDHHAQFLLSEKGSCADGSVK (SEQ ID NO: 72); or the first amino acid sequence is ASKVLESNQSVEDKHNEFMLTEYGSCADGSVKTSASKVAESNQSVEDKHNEFMLTEYG SCGDGSIKLSKVLESNQSVEDKHNEFMLTEYGSCADGSVKASKVAESNQSVEDKHNEF MLTEYGSCGDGSIK (SEQ ID NO: 73); or the first amino acid sequence is ASKVLPASRAVDDHHAQFLLSEKGSCADGSVKTSASKVAPASRAVDDHHAQFLLSEKG SCGDGSIKLSKVLPASRAVDDHHAQFLLSEKGSCADGSVKASKVAPASRAVDDHHAQF LLSEKGSCGDGSIK (SEQ ID NO: 74); or the first amino acid sequence is SEQ ID NO: 35; or the first amino acid sequence is SEQ ID NO: 33. In one embodiment, the first amino acid sequence is selected from the group consisting of SEQ ID NO: 31, SEQ ID NO: 29, SEQ ID NO: 69, SEQ ID NO: 70, SEQ ID NO: 71, SEQ ID NO: 72, SEQ ID NO: 73, SEQ ID NO: 74, SEQ ID NO: 35, and SEQ ID NO: 33. In one embodiment, the first amino acid is SEQ ID NO: 35.

In a fourth aspect of the invention, a polypeptide is provided having the amino acid sequence of SEQ ID NO: 1 or SEQ ID NO: 37, or an amino acid sequence having 1-5 conservative amino acid substitutions within SEQ ID NO: 1 or SEQ ID NO: 37. In some embodiments the polypeptide has the amino acid sequence of SEQ ID NO: 1 or SEQ ID NO: 37, or an amino acid sequence having 1-3 conservative amino acid substitutions within SEQ ID NO: 1 or SEQ ID NO: 37. In some embodiments the polypeptide has the amino acid sequence of SEQ ID NO: 1 or SEQ ID NO: 37. In some embodiments the polypeptide has the amino acid sequence of SEQ ID NO: 1. In some embodiments the polypeptide has the amino acid sequence of SEQ ID NO: 37.

In a fifth aspect of the invention, a polypeptide is provided wherein the polypeptide comprises the amino acid sequence of SEQ ID NO: 1 or SEQ ID NO: 37, or an amino acid sequence having 1-5 conservative amino acid substitutions with SEQ ID NO: 1 or SEQ ID NO: 37. In some embodiments the polypeptide comprises the amino acid sequence of SEQ ID NO: 1 or SEQ ID NO: 37, or an amino acid sequence having 1-3 conservative amino acid substitutions within SEQ ID NO: 1 or SEQ ID NO: 37. In some embodiments the polypeptide comprises the amino acid sequence of SEQ ID NO: 1 or SEQ ID NO: 37. In some embodiments the polypeptide comprises the amino acid sequence of SEQ ID NO: 1. In some embodiments the polypeptide comprises the amino acid sequence of SEQ ID NO: 37. In some embodiments, the polypeptide is a fusion protein comprising the amino acid sequence of SEQ ID NO: 1 or SEQ ID NO: 37, or an amino acid sequence having 1-5 conservative amino acid substitutions with SEQ ID NO: 1 or SEQ ID NO: 37. In some embodiments the fusion protein comprises the amino acid sequence of SEQ ID NO: 1 or SEQ ID NO: 37, or an amino acid sequence having 1-3 conservative amino acid substitutions within SEQ ID NO: 1 or SEQ ID NO: 37. In some embodiments the fusion protein comprises the amino acid sequence of SEQ ID NO: 1 or SEQ ID NO: 37. In some embodiments the fusion protein comprises the amino acid sequence of SEQ ID NO: 1. In some embodiments the fusion protein comprises the amino acid sequence of SEQ ID NO: 37.

In a sixth aspect, a host cell is provided, wherein the host cell comprises a nucleic acid molecule of the invention, i.e. a nucleic acid molecule encoding a fusion protein, as described herein, and wherein the host cell expresses the fusion protein. In some embodiments, the host cell expresses and secretes the fusion protein. In some embodiments, the nucleic acid molecule is integrated into the genome of the host cell. In some embodiments, the host cell is a bacterium. In some embodiments, the bacterium is *Listeria monocytogenes*. In some embodiments, the bacterium *Listeria monocytogenes* and the nucleic acid molecule is integrated into a virulence gene of *Listeria monocytogenes*, wherein the integration of said nucleic acid molecule disrupts expression of the virulence gene or disrupts a coding sequence of the virulence gene. In some embodiments, the virulence gene is actA or inlB.

In a seventh aspect, a method of expressing a polypeptide of interest from a host cell is provided, said method comprising introducing into the host cell an expression construct comprising the nucleic acid molecule of the invention, i.e. a nucleic acid molecule encoding a fusion protein, as described herein, wherein the fusion protein is operably linked to one or more regulatory elements which mediate expression, and optionally secretion, of the fusion protein in the host cell. In some embodiments, the nucleic acid molecule is integrated into the genome of the host cell. In some embodiments, the host cell is a bacterium. In some embodiments, the bacterium is *Listeria monocytogenes*. In some embodiments, the bacterium *Listeria monocytogenes* and the nucleic acid molecule is integrated into a virulence gene of *Listeria monocytogenes*, wherein the integration of said nucleic acid molecule disrupts expression of the virulence gene or disrupts a coding sequence of the virulence gene. In some embodiments, the virulence gene is actA or inlB.

A number of bacterial species have been developed for use as vaccines, or for use as cancer immunotherapeutics, and the nucleic acid molecules of the present invention can find use in expression of fusion proteins in such species. By way of example, preferred bacterial genuses are selected from the group consisting of *Listeria, Escherichia, Neisseria, Mycobacterium, Francisella, Bacillus, Salmonella, Shigella, Yersinia, Burkholderia, Brucella, Legionella, Rickettsia*, and *Chlamydia*. This list is not meant to be limiting. Most preferably, the bacterium is a facultative intracellular bacterium such as *Listeria, Salmonella, Shigella, Francisella, Mycobacterium, Legionella, Burkholderia* and *Brucella*. In certain exemplary embodiments described hereinafter, the bacterium is *Listeria monocytogenes*, including, e.g., modified *Listeria monocytogenes* ΔactA/ΔinlB (a *L. monocytogenes* in which the native actA and inlB genes have been deleted or rendered functionally deleted by mutation). This list is not meant to be limiting. See, e.g., WO04/006837; WO04/084936; WO04/110481; WO05/037233; WO05/092372; WO06/036550; WO07/103225; WO07/117371; WO08/109155; WO08/130551; WO08/140812; WO09/143085; WO09/143167; WO10/040135; WO11/060260; and WO14/074635, each of which is hereby incorporated by reference in its entirety, including all tables, figures, and claims. The bacterial species may be a facultative, intracellular bacterial vector. The bacterium may be used to deliver a polypeptide of interest (e.g., an antigen) as part of the fusion protein for use therapeutically or prophylactically, e.g. as a vaccine, or as a cancer immunotherapeutic. The bacterium may be used to deliver such a polypeptide of interest to antigen-presenting cells in the host organism.

In various embodiments, the nucleic acid molecule of the present invention may be provided to a host cell on a vector. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors).

Alternatively, the nucleic acid molecule of the present invention may be integrated into the genome of a host cell upon introduction into the host cell, and thereby are replicated along with the host genome. Such a nucleic acid molecule may be integrated into a virulence gene of a bacterium, and the integration of said nucleic acid sequence disrupts expression of the virulence gene or disrupts a coding sequence of the virulence gene. By way of example only, such a virulence gene may be *Listeria monocytogenes* actA or inlB.

In certain embodiments, the nucleic acid molecule of the present invention is expressed as a fusion protein comprising an in frame secretory signal sequence, thereby resulting in the fusion protein being secreted as one or more soluble polypeptide(s) by the bacterium. Numerous exemplary signal sequences are known in the art for use in bacterial, mammalian, and plant expression systems. In the case where the bacterium is *Listeria monocytogenes*, it is preferred that the secretory signal sequence is a *Listeria monocytogenes* signal sequence, most preferably the ActA signal sequence. Additional ActA or other linker amino acids may also be expressed fused to the immunogenic polypeptide(s). In preferred embodiments, the fusion protein of the present invention comprise an in-frame ActA signal sequence selected from the group consisting of SEQ ID NO: 25, SEQ ID NO: 26, SEQ ID NO: 27, and SEQ ID NO: 28, or an amino acid sequence having at least 90% sequence identity to said sequence.

In preferred embodiments, the present invention provides a nucleic acid sequence encoding a fusion protein, comprising:
(a) an ActA signal sequence selected from the group consisting of SEQ ID NO: 25, SEQ ID NO: 26, SEQ ID NO: 27, and SEQ ID NO: 28, or an amino acid sequence having at least 90% sequence identity to said sequence;

(b) a first amino acid sequence comprising (i) a plurality (2, 3, 4, 5, or more copies) of a protein expression enhancer amino acid sequence that is independently ESNQSVEDKH-NEFMLTEY (SEQ ID NO: 1) or PASRAVDDHHAQ-FLLSEK (SEQ ID NO: 37) or a sequence having at least 90% identity or homology thereto, or a sequence having 1-5 conservative amino acid substitutions thereof, and (ii) a linker amino acid sequence flanking each protein expression enhancer amino acid sequence, wherein each linker amino acid sequence is independently selected and configured for proteasomal cleavage; and (c) a polypeptide sequence of interest, such as a polypeptide sequence encoding an antigenic sequence, and most preferably comprising one or more tumor antigens or infectious disease antigens;

wherein the fusion protein is expressed from a nucleic acid sequence operably linked to a *Listeria monocytogenes* ActA promoter.

In certain embodiments the nucleic acid sequences encoding the antigenic polypeptide(s) are codon optimized for expression by the bacterium (e.g., *Listeria monocytogenes*). As described hereinafter, different organisms often display "codon bias"; that is, the degree to which a given codon encoding a particular amino acid appears in the genetic code varies significantly between organisms. In general, the more rare codons that a gene contains, the less likely it is that the heterologous protein will be expressed at a reasonable level within that specific host system. These levels become even lower if the rare codons appear in clusters or in the N-terminal portion of the protein. Replacing rare codons with others that more closely reflect the host system's codon bias without modifying the amino acid sequence can increase the levels of functional protein expression. Methods for codon optimization are described hereinafter.

In some embodiments, the polypeptide sequence of interest, such as the polypeptide sequence encoding an antigenic sequence as described herein, comprises one or more independent antigenic sequences. The term "independent antigenic sequences" refers to a polypeptide sequence that comprises an antigenic epitope (e.g., a predicted T-cell epitope) and that is different in sequence from the other polypeptide sequences present in the longer polypeptide. By way of example only, the polypeptide sequence of interest may comprise 50 independent antigenic sequences, 25 independent antigenic sequences, 20 independent antigenic sequences, 19 independent antigenic sequences, 18 independent antigenic sequences, 17 independent antigenic sequences, 16 independent antigenic sequences, 15 independent antigenic sequences, 14 independent antigenic sequences, 13 independent antigenic sequences, 12 independent antigenic sequences, 11 independent antigenic sequences, 10 independent antigenic sequences, 9 independent antigenic sequences, 8 independent antigenic sequences, 7 independent antigenic sequences, 6 independent antigenic sequences, 5 independent antigenic sequences, 4 independent antigenic sequences, 3 independent antigenic sequences, 2 independent antigenic sequences or 1 antigenic sequence. In some embodiments, the one or more independent antigenic sequences comprise one or more neoantigenic sequences. In some embodiments, the one or more neoantigenic sequences are one or more neoantigenic sequence expressed by one or more tumor cells in an individual suffering from a cancer. In some embodiments, the one or more neoantigenic sequences are expressed by one or more colorectal cancer cells in an individual suffering from a colorectal cancer.

In one aspect, the nucleic acid sequences of the invention, i.e. the nucleic acid sequences encoding the fusion protein as described herein, are used in a personalized live, attenuated, double-deleted *Listeria monocytogenes* (pLADD) based immunotherapy. In one embodiment of this aspect, the *Listeria monocytogenes* is a ΔactA/ΔinlB strain that comprises the nucleic acid sequence encoding the fusion protein, which comprises the polypeptide of interest, as described herein. In some embodiments, the pLADD is administered to an individual having a cancer, wherein the polypeptide of interest comprises one or more tumor-associated antigens expressed by one or more tumor cells in the individual. In some embodiments, the individual has a colorectal cancer.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
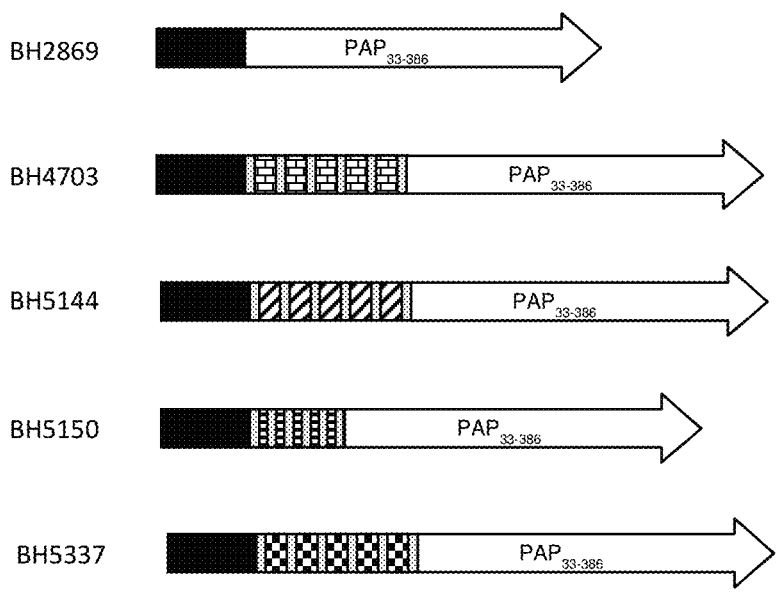
FIG. 1 depicts schematically the fusion protein constructs of *Listeria monocytogenes* strains BH2869, BH4703, BH5144, BH5150, and BH5337.

The present invention relates to compositions and methods for preparing and using attenuated bacterial species modified to increase the expression of one or more heterologous antigens. The present invention can provide attenuated bacterial vaccine strains or attenuated bacterial strains for use as cancer immunotherapeutics, with advantageous safety profiles for use in the treatment or prevention of diseases having a risk-benefit profile not appropriate for live non-attenuated vaccines.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. Definitions

Abbreviations used to indicate a mutation in a gene, or a mutation in a bacterium comprising the gene, are as follows. By way of example, the abbreviation "*L. monocytogenes* ΔactA" means that part, or all, of the actA gene was deleted. The delta symbol (Δ) means deletion. An abbreviation including a superscripted minus sign (*Listeria* ActA⁻) means that the actA gene was mutated, e.g., by way of a deletion, point mutation, or frameshift mutation, but not limited to these types of mutations.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) receptor can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen sequence" or "antigenic sequence" as used herein refers to an amino acid sequence comprising at least a minimal peptide (e.g. a peptide predicted to be immunogenic and bind the subject MHC molecules when flanked by the cleaver sequences as described herein) intended to induce an immune response when the fusion proteins of the invention delivered to a subject, e.g. by administration of a bacteria engineered to express and secrete the fusion protein. The antigenic sequence can comprise a tumor antigen, or an infectious disease antigen. The antigen sequences include known antigens as described herein, including any antigenic fragments thereof. In instances where the antigenic sequences comprise tumor antigens, the sequences include neoantigen sequences, e.g. a sequence determined for a particular individual by assessing antigens expressed by a cancer cell using methods known in the art (e.g. sequencing a biopsy of one or more cancer cells from the individual). In general, the antigenic sequence can include a full length gene sequence, or any antigenic fragment thereof, including a minimal peptide. Typically the antigenic sequence is at least about 8 amino acids, e.g. 8-1,000, 8-500, 8-400, 8-300, 8-200, 8-100, 8-90, 8-80, 8-70, 8-60, 8-50, 8-40, 8-30, 10-1,000, 10-500, 10-400, 10-300, 10-200, 10-100, 10-90, 10-80, 10-70, 10-60, 10-50, 10-40, or 10-30 amino acids in length. In some instances, the fusion protein can include more than one antigenic sequence fragment from a full length sequence, e.g. one or more epitopes from within a full length antigen. In some instances, the fusion protein can include more than one antigenic sequence fragments from different full length sequences, e.g. one or more epitopes from within different full length antigens. In some instances, the antigenic sequence comprises additional amino acids to alter the hydropathy of the peptide, or to enhance the T-cell response to include both CD4 and CD8 T-cell responses. Methods for improving the MHC binding of the antigenic sequence can be found in, e.g., Andreatta and Nielsen, (2016) Bioinformatics 32(4):511-7; and Nielsen et al., (2003) Protein Sci., 12:1007-17. In some instances, the antigenic sequence comprises a minimal peptide sequence and further comprises additional amino acids on either or both of the amino and carboxy terminus thereof, e.g. amino acids intended to alter the hydropathy of the antigenic sequence to improve predicted MHC binding of the antigenic sequence, or to improve the overall response to the antigenic sequence to induce both a CD4 and CD8 response.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses CD34+ CD45RA− early progenitor multipotent cells, CD34+ CD45RA+ cells, CD34+CD45RA+CD4+IL-3Ra+ pro-DC2 cells, CD4+CD11c-plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the LD50, the rate of clearance from an organ, or the competitive index (see, e.g., Auerbuch, et al. (2001) Infect. Immunity 69:5953-5957). Generally, an attenuation results an increase in the LD50 and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

A "cleaver sequence" or "cleaver amino acid sequence" refers to an amino acid sequence that is configured to be cleaved by a host cell proteasome. By way of example, without limitation, such cleaver sequences can be independently selected from the group consisting of ADGSVK (SEQ ID NO: 2), ASKVA (SEQ ID NO: 3), LSKVL (SEQ ID NO: 4), ASKVL (SEQ ID NO: 5), GDGSIK (SEQ ID NO: 6), ADGSV (SEQ ID NO: 7), LAKSL (SEQ ID NO: 8), ADLAVK (SEQ ID NO: 9), ASVVA (SEQ ID NO: 10), GIGSIA (SEQ ID NO: 11), GVEKI (SEQ ID NO: 12), NAANKG (SEQ ID NO: 13), DGSKKA (SEQ ID NO: 14), GDGNKK (SEQ ID NO: 15), KLSKVL (SEQ ID NO: 75), and GDGNK (SEQ ID NO: 76). In some embodiments, the fusion proteins of the invention comprise the enhancer sequence linked to a cleaver sequence at both the amino and carboxy terminus of the enhancer sequence, e.g. the fusion protein can comprise, for example, one or more of SEQ ID NO: 5↓SEQ ID NO: 2; SEQ ID NO: 3↓SEQ ID NO: 6; SEQ ID NO: 4↓SEQ ID NO: 2; SEQ ID NO: 8↓SEQ ID NO: 9; SEQ ID NO: 10↓SEQ ID NO: 11; SEQ ID NO: 12↓SEQ ID NO: 13; and SEQ ID NO: 14↓SEQ ID NO: 15, wherein ↓ represents the enhancer sequence of SEQ ID NO: 1 or SEQ ID NO: 37, or a sequence having at least 90% identity or homology thereto, or a sequence having 1-5 conservative amino acid substitutions thereof, linked to the cleaver sequence as indicated. This list is not meant to be limiting. In some embodiments, the fusion proteins of the invention comprise multiple antigenic sequences linked to a cleaver sequence at both the amino and carboxy terminus of the antigenic sequence, e.g. the fusion protein can comprise, for example, one or more of SEQ ID NO: 5↕ SEQ ID NO: 2; SEQ ID NO: 3↕ SEQ ID NO: 6; SEQ ID NO: 4↕ SEQ ID NO: 2; SEQ ID NO: 4↕ SEQ ID NO: 7; SEQ ID NO: 8↕ SEQ ID NO: 9; SEQ ID NO: 10↕ SEQ ID NO: 11; SEQ ID NO: 12↕ SEQ ID NO: 13; SEQ ID NO: 14↕ SEQ ID NO: 15; SEQ ID NO: 14↕ SEQ ID NO: 2; SEQ ID NO: 14↕ SEQ ID NO: 76; SEQ ID NO: 75↕ SEQ ID NO: 2; and SEQ ID NO: 75↕ SEQ ID NO: 76, wherein ↕ represents the antigenic sequence linked to the cleaver sequence as indicated. This list is not meant to be limiting.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. In some embodiments, the enhancer sequence as described herein include said sequence having 1-5, 1-4, 1-3, 1-2, or 1 conservative amino acid substitutions thereof. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132).

(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

The term "enhancer sequence" or "enhancer amino acid sequence" is used to describe the unique amino acid sequences as described herein (e.g., a sequence independently selected from the group consisting of ESNQSVED-KHNEFMLTEY (SEQ ID NO: 1) and PASRAVDDHHAQ-FLLSEK (SEQ ID NO: 37), or a sequence having at least 90% identity or homology thereto, or a sequence having 1-5 conservative amino acid substitutions thereof), that have been found to significantly enhance the expression and/or secretion from a bacteria or other organism of a fusion protein comprising one or more of these enhancer amino acid sequences. Such enhancer sequences are particularly useful for increasing the expression and/or secretion of antigenic sequences contained within the fusion protein. For example, when a bacterium comprising a nucleic acid sequence of the invention is used as a vaccine or cancer immunotherapeutic, the increased expression/secretion due to the enhancer sequence provides an improved immune response to the antigenic sequences as compared to a fusion protein lacking such an enhancer amino acid sequence.

An “extracellular fluid” encompasses, e.g., serum, plasma, blood, interstitial fluid, cerebrospinal fluid, secreted fluids, lymph, bile, sweat, fecal matter, and urine. An “extracelluar fluid” can comprise a colloid or a suspension, e.g., whole blood or coagulated blood.

The term “fragments” in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

“Gene” refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, “gene” encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressible sequence is generally considered a pseudogene. The term gene also encompasses nucleic acid sequences encoding a ribonucleic acid such as rRNA, tRNA, or a ribozyme.

“Growth” of a bacterium such as *Listeria* encompasses, without limitation, functions of bacterial physiology and genes relating to colonization, replication, increase in protein content, and/or increase in lipid content. Unless specified otherwise explicitly or by context, growth of a *Listeria* encompasses growth of the bacterium outside a host cell, and also growth inside a host cell. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, “growth” of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a Listerial antigen, Listerial nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

A "hydropathy analysis" refers to the analysis of a polypeptide sequence by the method of Kyte and Doolittle: "A Simple Method for Displaying the Hydropathic Character of a Protein". J. Mol. Biol. 157 (1982)105-132. In this method, each amino acid is given a hydrophobicity score between 4.6 and −4.6. A score of 4.6 is the most hydrophobic and a score of −4.6 is the most hydrophilic. Then a window size is set. A window size is the number of amino acids whose hydrophobicity scores will be averaged and assigned to the first amino acid in the window. The calculation starts with the first window of amino acids and calculates the average of all the hydrophobicity scores in that window. Then the window moves down one amino acid and calculates the average of all the hydrophobicity scores in the second window. This pattern continues to the end of the protein, computing the average score for each window and assigning it to the first amino acid in the window. The averages are then plotted on a graph. The y axis represents the hydrophobicity scores and the x axis represents the window number. The following hydrophobicity scores are used for the 20 common amino acids.

| | | |
|---|---|---|
| Arg: −4.5 | Ser: −0.8 | Lys: −3.9 |
| Thr: −0.7 | Asn: −3.5 | Gly: −0.4 |
| Asp: −3.5 | Ala: 1.8 | Gln: −3.5 |
| Met: 1.9 | Glu: −3.5 | Cys: 2.5 |
| His: −3.2 | Phe: 2.8 | Pro: −1.6 |
| Leu: 3.8 | Tyr: −1.3 | Val: 4.2 |
| Trp: −0.9 | Ile: 4.5 | |

A composition that is "labeled" is detectable, either directly or indirectly, by spectroscopic, photochemical, biochemical, immunochemical, isotopic, or chemical methods. For example, useful labels include 32P, 33P, 35S, 14C, 3H, 125I, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Linked to" as it is used herein with respect to fusion protein products, refers to two amino acid sequences of the invention (e.g. a secretary signal sequence and a first amino acid sequence as described herein) within a fusion protein that are linked either directly via the peptide bond of the carboxy terminus of one sequence and the amino terminus of the other sequence, or can be linked via peptide bonds of a "linker sequence" of one or more amino acids (e.g. 1-100, 1-50, 1-20, 1-10, 1-9, 1-8, 1-7, 1-6, 1-5, 1-4, 1-3, 1-2, or 1 amino acids). One skilled in the art can readily provide the nucleic acid sequence necessary to produce the fusion protein of interest, e.g. where the one or more amino acid sequence that links e.g. a signal sequence to a first amino acid sequence comprising the enhancer sequence, as described herein. In some instances the one or more amino acid sequence linking two amino acid sequences of the invention are the result of restriction sites used in preparing the nucleic acids of the invention. Upon ligation of the restriction enzyme products, the resulting nucleic acid sequence translate a residual amino acid sequence into the fusion protein, such sequences may be referred to herein as a "restriction fragment residual". Such a restriction fragment residual is well known in the art, and is typically 2 amino acids. For example, where a BamHI restriction sequence is used, the resulting ggatcc sequence of the nucleic acid results in a residual GS linkage between the two amino acid components expressed as the protein fusion sequence. Similarly, SpeI restriction sequence actagt results in a residual TS linkage.

"Ligand" refers to a small molecule, peptide, polypeptide, or membrane associated or membrane-bound molecule that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

A "neoantigen" or "neoantigenic sequence" refers to a newly formed antigen that has not been previously recognized by the immune system of the individual in which the neoantigen has formed. Neoantigens are often associated with oncogenic or virally-infected cells. Neoantigens can be formed when a protein undergoes further modification within a biochemical pathway such as glycosylation, phosphorylation or proteolysis, or by mutation at the nucleic acid level. By altering the structure of an otherwise normal protein, this process can produce new epitopes (called "neoantigenic determinants") as they give rise to new antigenic determinants. Such antigens are new and can be specific to the tumor cells or virally infected cells in an individual (e.g. as the result of a mutation within a gene in the tumor cells), and provide a target for immunotherapy directed against the tumor or virus. In the context of the present invention, an individual suffering from a cancer will preferably express one or more neoantigens on the cancer cells. The individual's cancer, i.e. tumor cells, can be biopsied and assayed to determine the identity of any neoantigens, which can be engineered into the fusion protein constructs of the present invention for purposes of immunotherapy. Thus the fusion proteins as described herein can comprise one or more independently selected neoantigens, e.g. 1-50, 1-25, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 or 1 independently selected neoantigenic sequences.

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

A "pharmaceutically acceptable excipient" or "diagnostically acceptable excipient" refers to an excipient that can be used with (i.e. in the formulation of) e.g. the bacteria comprising the nucleic acids as described herein for therapeutic or diagnostic use, Such excipients include, but is not limited to, sterile distilled water, saline, phosphate buffered solutions, amino acid based buffers, or bicarbonate buffered solutions. An excipient selected and the amount of excipient used will depend upon the use, e.g. the mode of administration for therapeutic or diagnostic use (e.g. oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration).

By "purified" and "isolated" is meant, when referring to a polypeptide or nucleic acid, that the polypeptide is present in the substantial absence of the other biological macromolecules with which it is associated in nature. In some embodiments, the nucleic acid molecules and fusion proteins of the inventions as described herein are isolated nucleic acid molecules or fusion proteins. The term "purified" as used herein means that an identified polypeptide or nucleic acid often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like.

The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction that is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Cabs (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, delaying relapse of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, delaying relapse of a condition, alleviating one or more symptoms associated with a condition, increasing the quality of life of one suffering from a condition, and/or prolonging survival.

"Vaccine" encompasses preventative vaccines, including vaccines for prevention of the relapse of a disease. Vaccine also encompasses therapeutic vaccines, e.g., a vaccine administered to a mammal that comprises a condition or disorder associated with the antigen or epitope provided by the vaccine.

By "immunogenic" as that term is used herein is meant that the antigen is capable of eliciting an antigen-specific humoral or T-cell response (CD4+ and/or CD8+). Selection of one or more antigens or derivatives thereof for use in the vaccine compositions of the present invention may be performed in a variety of ways, including an assessment of the ability of a bacterium of choice to successfully express and secrete the recombinant antigen(s); and/or the ability of the recombinant antigen(s) to initiate an antigen specific CD4+ and/or CD8+ T cell response. As discussed hereinafter, in order to arrive at a final selection of antigen(s) for use with a particular bacterial delivery vehicle, these attributes of the recombinant antigen(s) are preferably combined with the ability of the complete vaccine platform (meaning the selected bacterial expression system for the selected antigen (s)) to initiate both the innate immune response as well as an antigen-specific T cell response against the recombinantly expressed antigen(s). An initial determination of suitable antigens may be made by selecting antigen(s) or antigen fragment(s) that are successfully recombinantly expressed by the bacterial host of choice (e.g., Listeria), and that are immunogenic.

Direct detection of expression of the recombinant antigen by Western blot may be performed using an antibody that detects the antigenic sequence being recombinantly produced, or using an antibody that detects an included sequence (a "tag") that is expressed with the antigen as a fusion protein. For example, the antigen(s) may be expressed as fusions with an N-terminal portion of the Listeria ActA protein, and an anti-ActA antibody raised against a synthetic peptide (ATDSEDSSLNTDEWEEEK (SEQ ID NO: 77)) corresponding to the mature N terminal 18 amino acids of ActA can be used to detect the expressed protein product.

Assays for testing the immunogenicity of antigens are described herein and are well known in the art. As an example, an antigen recombinantly produced by a bacterium of choice can be optionally constructed to contain the nucleotide sequence encoding an eight amino SIINFEKL (SEQ ID NO: 38) peptide (also known as SL8 and ovalbumin 257-264), positioned in-frame at the carboxyl terminus of the antigen. Compositions such as the C-terminal SL8 epitope serve as a surrogate (i) to demonstrate that the recombinant antigen is being expressed in its entirety from N-terminal to C-terminal, and (ii) to demonstrate the ability of antigen presenting cells to present the recombinant antigen via the MHC class I pathway, using an in vitro antigen presentation assay. Such a presentation assay can be performed using the cloned C57BL/6-derived dendritic cell line DC2.4 together with the B3Z T cell hybridoma cell line as described hereinafter.

Alternatively, or in addition, immunogenicity may be tested using an ELISPOT assay as described hereinafter. ELISPOT assays were originally developed to enumerate B cells secreting antigen-specific antibodies, but have subsequently been adapted for various tasks, especially the identification and enumeration of cytokine-producing cells at the single cell level. Spleens may be harvested from animals inoculated with an appropriate bacterial vaccine, and the isolated splenocytes incubated overnight with or without peptides derived from the one or more antigens expressed by the bacterial vaccine. An immobilized antibody captures any secreted IFN-γ, thus permitting subsequent measurement of secreted IFN-γ, and assessment of the immune response to the vaccine.

2. Recombinant Expression Systems—the "Vaccine Platform"

A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or *Mycobacterium* species, preferably *Listeria monocytogenes*. This list is not meant to be limiting. See, e.g., WO04/006837; WO07/103225; and WO07/117371, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, *L. monocytogenes* provides a preferred vaccine platform for expression of the antigens of the present invention.

Recombinant vectors are prepared using standard techniques known in the art, and contain suitable control elements operably linked to the nucleotide sequence encoding the target antigen. See, for example, Plotkin, et al. (eds.) (2003) Vaccines, 4th ed., W.B. Saunders, Co., Phila., Pa.; Sikora, et al. (eds.) (1996) Tumor Immunology Cambridge University Press, Cambridge, UK; Hackett and Harn (eds.) Vaccine Adjuvants, Humana Press, Totowa, N.J.; Isaacson (eds.) (1992) Recombinant DNA Vaccines, Marcel Dekker, NY, NY; Morse, et al. (eds.) (2004) Handbook of Cancer Vaccines, Humana Press, Totowa, N.J.), Liao, et al. (2005) Cancer Res. 65:9089-9098; Dean (2005) Expert Opin. Drug Deliv. 2:227-236; Arlen, et al. (2003) Expert Rev. Vaccines 2:483-493; Dela Cruz, et al. (2003) Vaccine 21:1317-1326; Johansen, et al. (2000) Eur. J. Pharm. Biopharm. 50:413-417; Excler (1998) Vaccine 16:1439-1443; Disis, et al. (1996) J. Immunol. 156:3151-3158). Peptide vaccines are described (see, e.g., McCabe, et al. (1995) Cancer Res. 55:1741-1747; Minev, et al. (1994) Cancer Res. 54:4155-4161; Snyder, et al. (2004) J. Virology 78:7052-7060.

Antigen expression platforms may also be provided using naked DNA vectors and naked RNA vectors. These vaccines containing nucleic acids may be administered by a gene gun, electroporation, bacterial ghosts, microspheres, microparticles, liposomes, polycationic nanoparticles, and the like (see, e.g., Donnelly, et al. (1997) Ann. Rev. Immunol. 15:617-648; Mincheff, et al. (2001) Crit. Rev. Oncol. Hematol. 39:125-132; Song, et al. (2005) J. Virol. 79:9854-9861; Estcourt, et al. (2004) Immunol. Rev. 199:144-155). Reagents and methodologies for administration of naked nucleic acids, e.g., by way of a gene gun, intradermic, intramuscular, and electroporation methods, are available. The nucleic acid vaccines may comprise a locked nucleic acid (LNA), where the LNA allows for attachment of a functional moiety to the plasmid DNA, and where the functional moiety can be an adjuvant (see, e.g., Fensterle, et al. (1999) J. Immunol. 163:4510-4518; Strugnell, et al. (1997) Immunol. Cell Biol. 75:364-369; Hertoughs, et al. (2003) Nucleic Acids Res. 31:5817-5830; Trimble, et al. (2003) Vaccine 21:4036-4042; Nishitani, et al. (2000) Mol. Urol. 4:47-50; Tuting (1999) Curr. Opin. Mol. Ther. 1:216-225). Nucleic acid vaccines can be used in combination with reagents that promote migration of immature dendritic cells towards the vaccine, and a reagent that promotes migration of mature DCs to the draining lymph node where priming can occur, where these reagents encompass MIP-1alpha and Flt3L (see, e.g., Kutzler and Weiner (2004) J. Clin. Invest. 114:1241-1244; Sumida, et al. (2004) J. Clin. Invest. 114:1334-1342).

Both attenuated and commensal microorganisms have been successfully used as carriers for vaccine antigens, but bacterial carriers for the antigens are optionally attenuated or killed but metabolically active (KBMA). The genetic background of the carrier strain used in the formulation, the type of mutation selected to achieve attenuation, and the intrinsic properties of the immunogen can be adjusted to optimize the extent and quality of the immune response elicited. The general factors to be considered to optimize the immune response stimulated by the bacterial carrier include: selection of the carrier; the specific background strain, the attenuating mutation and the level of attenuation; the stabilization of the attenuated phenotype and the establishment of the optimal dosage. Other antigen-related factors to consider include: intrinsic properties of the antigen; the expression system, antigen-display form and stabilization of the recombinant phenotype; co-expression of modulating molecules and vaccination schedules.

A preferred feature of the vaccine platform is the ability to initiate both the innate immune response as well as an antigen-specific T cell response against the recombinantly expressed antigen(s). For example, *L. monocytogenes* expressing the antigen(s) described herein can induce intrahepatic Type 1 interferon (IFN-$\alpha/\beta$) and a downstream cascade of chemokines and cytokines. In response to this intrahepatic immune stimulation, NK cells and antigen presenting cells (APCs) are recruited to the liver. In certain embodiments, the vaccine platform of the present invention induces an increase at 24 hours following delivery of the vaccine platform to the subject in the serum concentration of one or more, and preferably all, cytokines and chemokines selected from the group consisting of IL-12p70, IFN-$\gamma$, IL-6, TNF $\alpha$, and MCP-1; and induces a CD4+ and/or CD8+ antigen-specific T cell response against one or more antigens expressed by the vaccine platform. In other embodiments, the vaccine platform of the present invention also induces the maturation of resident immature liver NK cells as demonstrated by the upregulation of activation markers such as DX5, CD11b, and CD43 in a mouse model system, or by NK cell-mediated cytolytic activity measured using 51Cr-labeled YAC-1 cells that were used as target cells.

In various embodiments, the vaccines and immunogenic compositions of the present invention can comprise *Listeria monocytogenes* configured to express the fusion protein of the invention. The ability of *L. monocytogenes* to serve as a vaccine vector has been reviewed in Wesikirch, et al., Immunol. Rev. 158:159-169 (1997). A number of desirable features of the natural biology of *L. monocytogenes* make it an attractive platform for application to a therapeutic vaccine. The central rationale is that the intracellular lifecycle of *L. monocytogenes* enables effective stimulation of CD4+ and CD8+ T cell immunity. Multiple pathogen associated molecular pattern (PAMP) receptors including TLRs (TLR2, TLR5, TLR9) and nucleotide-binding oligomerization domains (NOD) are triggered in response to interaction with *L. monocytogenes* macromolecules upon infection, resulting in the pan-activation of innate immune effectors and release of Th-1 polarizing cytokines, exerting a profound impact on the development of a CD4+ and CD8+ T cell response against the expressed antigens.

Strains of *L. monocytogenes* have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn et al., J. Immunol., 167:6471-6479 (2001); Liau, et al., Cancer Research, 62: 2287-2293 (2002); U.S. Pat. No. 6,099,848; WO 99/25376; WO 96/14087; and U.S. Pat. No. 5,830,702), each of which is hereby incorporated by reference in its entirety, including all tables, figures, and claims.

A recombinant *L. monocytogenes* vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

Attenuated and killed but metabolically active forms of *L. monocytogenes* useful in immunogenic compositions have been produced (WO04/006837; WO04/084936; WO04/110481; WO05/037233; WO05/092372; WO06/036550; WO07/103225; WO07/117371; WO08/109155; WO08/130551; WO08/140812; WO09/143085; WO09/143167; WO10/040135; WO11/060260; and WO14/074635), each of which is hereby incorporated by reference in its entirety, including all tables, figures, and claims. The ActA protein of *L. monocytogenes* is sufficient to promote the actin recruitment and polymerization events responsible for intracellular movement. A human safety study has reported that oral administration of an actA/plcB-deleted attenuated form of *L. monocytogenes* caused no serious sequelae in adults (Angelakopoulos et al., Infection and Immunity, 70:3592-3601 (2002)). Other types of attenuated forms of *L. monocytogenes* have also been described (see, for example, WO 99/25376 and U.S. Pat. No. 6,099,848, which describe auxotrophic, attenuated strains of *Listeria* that express heterologous antigens).

In certain embodiments, the *L. monocytogenes* used in the vaccine compositions of the present invention is a live-attenuated strain that comprises an attenuating mutation in actA and/or inlB, and preferably a deletion of all or a portion of actA and inlB (referred to herein as "Lm ΔactA/ΔinlB"), and contains recombinant DNA encoding for the expression of the fusion protein comprising the antigen(s) of interest. The fusion protein containing the antigen(s) is preferably under the control of bacterial expression sequences and are stably integrated into the *L. monocytogenes* genome. Such a *L. monocytogenes* vaccine strain therefore employs no eukaryotic transcriptional or translational elements.

The invention also contemplates a *Listeria* attenuated in at least one regulatory factor, e.g., a promoter or a transcription factor. The following concerns promoters. ActA expression is regulated by two different promoters (Vazwuez-Boland, et al. (1992) Infect. Immun. 60:219-230). Together, InlA and InlB expression is regulated by five promoters (Lingnau, et al. (1995) Infect. Immun. 63:3896-3903). The transcription factor prfA is required for transcription of a number of *L. monocytogenes* genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA box, and the like (see, e.g., Lalic Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun. 73:1917-1926; Wong and Freitag (2004) J. Bacteriol. 186:6265-6276; Ripio, et al. (1997) J. Bacteriol. 179:1533-1540).

Attenuation can be effected by, e.g., heat-treatment or chemical modification. Attenuation can also be effected by genetic modification of a nucleic acid that modulates, e.g., metabolism, extracellular growth, or intracellular growth, genetic modification of a nucleic acid encoding a virulence factor, such as Listerial prfA, actA, listeriolysin (LLO), an adhesion mediating factor (e.g., an internalin such as inlA or inlB), mpl, phosphatidylcholine phospholipase C (PC-PLC), phosphatidylinositol-specific phospholipase C (PI PLC; plcA gene), any combination of the above, and the like. Attenuation can be assessed by comparing a biological function of an attenuated *Listeria* with the corresponding biological function shown by an appropriate parent *Listeria*.

The present invention, in other embodiments, provides a *Listeria* that is attenuated by treating with a nucleic acid targeting agent, such as a cross linking agent, a psoralen, a nitrogen mustard, cis platin, a bulky adduct, ultraviolet light, gamma irradiation, any combination thereof, and the like. Typically, the lesion produced by one molecule of cross linking agent involves cross linking of both strands of the double helix. The *Listeria* of the invention can also be attenuated by mutating at least one nucleic acid repair gene, e.g., uvrA, uvrB, uvrAB, uvrC, uvrD, uvrAB, phrA, and/or a gene mediating recombinational repair, e.g., recA. Moreover, the invention provides a *Listeria* attenuated by both a nucleic acid targeting agent and by mutating a nucleic acid repair gene. Additionally, the invention encompasses treating with a light sensitive nucleic acid targeting agent, such as a psoralen, and/or a light sensitive nucleic acid cross linking agent, such as psoralen, followed by exposure to ultraviolet light.

Attenuated *Listeria* useful in the present invention are described in, e.g., U.S. Pat. Publ. Nos. 2004/0228877 and 2004/0197343, and in PCT publications WO04/006837; WO04/084936; WO04/110481; WO05/037233; WO05/092372; WO06/036550; WO07/103225; WO07/117371; WO08/109155; WO08/130551; WO08/140812; WO09/143085; WO09/143167; WO10/040135; WO11/060260; and WO14/074635, each of which is incorporated by reference herein in its entirety. Various assays for assessing whether a particular strain of *Listeria* has the desired attenuation are provided, e.g., in U.S. Pat. Publ. Nos. 2004/0228877, 2004/0197343, and 2005/0249748, each of which is incorporated by reference herein in its entirety.

In other embodiments, the *L. monocytogenes* used in the vaccine compositions of the present invention is a killed but metabolically active (KBMA) platform derived from Lm ΔactA/ΔinlB, and also is deleted of both uvrA and uvrB, genes encoding the DNA repair enzymes of the nucleotide excision repair (NER) pathway, and contains recombinant DNA encoding for the expression of the fusion protein. The antigen(s) of interest are preferably under the control of bacterial expression sequences and are stably integrated into the *L. monocytogenes* genome. The KBMA platform is exquisitely sensitive to photochemical inactivation by the combined treatment with the synthetic psoralen, S-59, and long-wave UV light. While killed, KBMA *L. monocytogenes* vaccines can transiently express their gene products, allowing them to escape the phagolysosome and induce functional cellular immunity and protection against wild-typeWT Lm and vaccinia virus challenge.

In certain embodiments, an attenuated or KBMA *L. monocytogenes* vaccine strain comprise a constitutively active prfA gene (referred to herein as PrfA* mutants). PrfA is a transcription factor activated intracellularly that induces expression of virulence genes and encoded heterologous antigens (Ags) in appropriately engineered vaccine strains. As noted above, expression of the actA gene is responsive to PrfA, and the actA promoter is a PrfA responsive regulatory element. Inclusion of a prfA G155S allele can confer significant enhanced vaccine potency of live-attenuated or KBMA vaccines. Preferred PrfA mutants are described in WO2009/143085, entitled COMPOSITIONS COMPRISING PRFA* MUTANT *LISTERIA* AND METHODS OF USE THEREOF, filed May 18, 2009, which is hereby incorporated in its entirety including all tables, figures, and claims.

3. Antigenic Constructs

The antigenic portion of the fusion proteins of the present invention preferably comprises a nucleic acid encoding a secretory sequence operable within the vaccine platform to support secretion, one or more enhancer sequences of the present invention, and the antigen(s) to be expressed. In the case of a bacterial platform, the resulting fusion protein may be operably linked to regulatory sequences (e.g., a promoter) necessary for expression of the fusion protein by the bacterial vaccine platform. The present invention is not to be limited to polypeptide and peptide antigens that are secreted, but also embraces polypeptides and peptides that are not secreted or cannot be secreted from a *Listeria* or other bacterium. But preferably, the antigen(s) are expressed in a soluble, secreted form by a bacterial vaccine strain when the strain is inoculated into a recipient.

Examples of antigens that may find use in the invention, without limitation, are listed in the following table. The target antigen may also be a fragment or fusion polypeptide comprising an immunologically active portion of several antigens listed in the following Table 1. The fusion proteins of the present invention may comprise more than one antigenic sequence. This list is not meant to be limiting.

TABLE 1

| Antigens. | |
|---|---|
| Antigen | Reference |
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |

TABLE 1-continued

Antigens.

| Antigen | Reference |
| --- | --- |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |

TABLE 1-continued

Antigens.

| Antigen | Reference |
|---|---|
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |

TABLE 1-continued

| Antigens. | |
|---|---|
| Antigen | Reference |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |
| *Francisella tularensis* antigens | |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |
| Malarial antigens | |
| Circumsporozoite protein (CSP); SSP2; HEP17; Exp-1 orthologs found in *P. falciparum*; and | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank |

TABLE 1-continued

Antigens.

| Antigen | Reference |
|---|---|
| LSA-1. Ring-infected erythrocyte survace protein (RESA); merozoite surface protein 2 (MSP2); Spf66; merozoite surface protein 1(MSP1); 195A; BVp42. | Acc. No. Z30319). See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |

Viruses and viral antigens

| Antigen | Reference |
|---|---|
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |

TABLE 1-continued

Antigens.

| Antigen | Reference |
|---|---|
| E27, E29 to E33, and EV69 and E73), as well as HEV. | |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |

TABLE 1-continued

Antigens.

| Antigen | Reference |
|---|---|
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |

TABLE 1-continued

Antigens.

| Antigen | Reference |
|---|---|
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Caliciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), *enterica* (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

The following Table 2 discloses a number of non-limiting examples of signal peptides for use in expressing and secreting a fusion protein polypeptide of interest such as an antigenic sequence. Signal peptides tend to contain three domains: a positively charged N-terminus (1-5 residues long); a central hydrophobic comain (7-15 residues long); and a neutral but polar C-terminal domain.

TABLE 2

Bacterial signal pathway. Signal peptides are identified by the signal peptidase site.

| Signal peptidase site (cleavage site represented by ') | Gene | Genus/species |
|---|---|---|
| secA1 pathway | | |
| TEA'KD (SEQ ID NO: 18) | hly (LLO) | Listeria monocytogenes |
| VYA'DT (SEQ ID NO: 19) | Usp45 | Lactococcus lactis |
| IQA'EV (SEQ ID NO: 20) | pag (protective antigen) | Bacillus anthracis |
| secA2 pathway | | |
| ASA'ST (SEQ ID NO: 21) | iap (invasion-associated protein) p60 | Listeria monocytogenes |
| VGA'FG (SEQ ID NO: 22) | NamA lmo2691 (autolysin) | Listeria monocytogenes |
| AFA'ED (SEQ ID NO: 23) | * BA_0281 (NLP/P60 Family) | Bacillus anthracis |
| VQA'AE (SEQ ID NO: 24) | * atl (autolysin) | Staphylococcus aureus |
| Tat pathway | | |
| DKA'LT (SEQ ID NO: 65) | lmo0367 | Listeria monocytogenes |
| VGA'FG (SEQ ID NO: 66) | PhoD (alkaline phosphatase) | Bacillus subtilis |

* Bacterial autolysins secreted by sec pathway (not determined whether secA1 or secA2).

Secretory sequences are encompassed by the indicated nucleic acids encoded by the *Listeria* EGD genome (GenBank Acc. No. NC_003210) at, e.g., nucleotides 45434-456936 (inlA); nucleotides 457021-457125 (inlB); nucleotides 1860200-1860295 (inlC); nucleotides 286219-287718 (inlE); nucleotides 205819-205893 (hly gene; LLO) (see also GenBank Acc. No. P13128); nucleotides 209470-209556 (ActA) (see also GenBank Acc. No. S20887).

The referenced nucleic acid sequences, and corresponding translated amino acid sequences, and the cited amino acid sequences, and the corresponding nucleic acid sequences associated with or cited in that reference, are incorporated by reference herein in their entirety.

In certain exemplary embodiments described hereinafter, the fusion protein is fused at its amino terminal end to an amino-terminal portion of the *L. monocytogenes* ActA or LLO protein that permits expression and secretion of a fusion protein from the bacterium within the vaccinated host. The ActA signal sequence is MGLNRFMRAMMV-VFITANCITINPDIIFA (SEQ ID NO: 41); the LLO signal sequence is MKKIMLVFIT LILVSLPIAQQTE (SEQ ID NO: 42). Preferably, the native signal sequence used is not modified in the construct.

Antigens may be expressed as a single polypeptide fused to an amino-terminal portion of the *L. monocytogenes* ActA protein that comprises its secretory signal sequence and permits expression and secretion of a fusion protein from the bacterium within the host cell. This ActA fragment may comprise at least the first 59 amino acids of ActA, or a sequence having at least about 80% sequence identity, at least about 85% sequence identity, at least about 90% sequence identity, at least about 95% sequence identity, or at least about 98% sequence identity to at least the first 59 amino acids of ActA. In some embodiments, the modified ActA comprises at least the first 100 amino acids of ActA, or a sequence having at least about 80% sequence identity, at least about 85% sequence identity, at least about 90% sequence identity, at least about 95% sequence identity, or at least about 98% sequence identity to the first 100 amino acids of ActA. A 100-residue N-terminal fragment of ActA has the following sequence (SEQ ID NO: 25):

```
VGLNRFMRAM MVVFITANCI TINPDIIFAA TDSEDSSLNT DEWEEEKTEE      50
QPSEVNTGPR YETAREVSSR DIEELEKSNK VKNTNKADLI AMLKAKAEKG
                                                          100
```

In this sequence, the first residue is depicted as a valine; the polypeptide is synthesized by *Listeria* with a methionine in this position. Thus, the $Val_1Met$ substituted form may also be used.

The fusion proteins of the present invention may comprise one or more additional amino acid residues that are not associate with ActA (or other secretory signal sequence, such as LLO), an enhancer sequence, a cleaver sequence or an antigenic sequence. Thus, for example, the secretory signal sequence may be linked to the first amino acid sequence (comprising enhancer sequences) or the second amino acid sequence (comprising antigenic sequences) and the first amino acid sequence may be linked to the second amino acid sequence by amino acid residues that are not relevant to the expression or secretion, cleavage or antigenic nature of the fusion protein. Each of these optional amino acid residues linking these sequences can be one or more amino acids, such as 1-100, 1-50, 1-25, 1-20, 1-25, 1-10, 1-9, 1-8, 1-7, 1-6, 1-5, 1-4, 1-3, 1-2 or 1 amino acids. Also, wherein the fusion protein comprises more than on enhancer sequence, and each enhancer sequence is described as linked to a cleaver sequence at both the amino terminus and carboxy terminus, the linkage of the cleaver sequence to the enhancer sequence can be a peptide bond, or one or more amino acids, such as 1-100, 1-50, 1-25, 1-20, 1-25, 1-10, 1-9, 1-8, 1-7, 1-6, 1-5, 1-4, 1-3, 1-2 or 1 amino acids. Also, wherein the fusion protein comprises more than on antigenic sequence, and each antigenic sequence is described as linked to a cleaver sequence at both the amino terminus and carboxy terminus, the linkage of the cleaver sequence to the antigenic sequence can be a peptide bond, or one or more amino acids, such as 1-100, 1-50, 1-25, 1-20, 1-25, 1-10, 1-9, 1-8, 1-7, 1-6, 1-5, 1-4, 1-3, 1-2 or 1 amino acids. By way of example, the fusion proteins of the invention comprising a secretory signal sequence, a first amino acid sequence comprising one or more enhancer amino acid sequences linked to a cleaver sequence at both its amino terminus and carboxy terminus, and a second amino acid sequence comprising one or more antigenic sequence linked to a cleaver sequence at both its amino terminus and carboxy terminus can be represented as comprising the polypeptide structure of (secretory signal sequence)-$L_1$-[first amino acid sequence]-$L_2$-[second amino acid sequence] or (secretory signal sequence)-$L_3$-[second amino acid sequence]-$L_4$-[first amino acid sequence]. Further by way of example, wherein the fusion protein includes two enhancer amino acid sequences and two antigenic sequences, this can be represented as (secretory signal sequence)-$L_1$-[(cleaver sequence 1)-$L_5$-(enhancer sequence 1)-$L_6$-(cleaver sequence 1')-$L_7$-(cleaver sequence 2)-$L_8$-(enhancer sequence 2)-$L_9$-(cleaver sequence 2')]-$L_2$-[(cleaver sequence 3)-$L_{10}$-(antigenic sequence 1)-$L_{11}$-(cleaver sequence 3')-$L_{12}$-(cleaver sequence 4)-$L_{13}$-(antigenic sequence 2)-$L_{14}$-(cleaver sequence 4')], or (secretory signal sequence)-$L_3$-[(cleaver sequence 3)-$L_{10}$-(antigenic sequence 1)-$L_{11}$-(cleaver sequence 3')-$L_{12}$-(cleaver sequence 4)-$L_{13}$-(antigenic sequence 2)-$L_{14}$-(cleaver sequence 4')]-$L_4$-[(cleaver sequence 1)-$L_5$-(enhancer sequence 1)-$L_6$-(cleaver sequence 1')-$L_7$-(cleaver sequence 2)-$L_8$-(enhancer sequence 2)-$L_9$-(cleaver sequence 2')]. In these examples, each $L_1$, $L_2$, $L_3$, $L_4$, $L_5$, $L_6$, $L_7$, $L_8$, $L_9$, $L_{10}$, $L_{11}$, $L_{12}$, $L_{13}$ and $L_{14}$ is independently selected from the group consisting of a direct bond (i.e. peptide bond), or one or more additional linker amino acid residues that are not associated with the secretory signal sequence, the enhancer sequences, the cleaver sequences or the antigenic sequences. In some embodiments, each $L_1$, $L_2$, $L_3$, $L_4$, $L_5$, $L_6$, $L_7$, $L_8$, $L_9$, $L_{10}$, $L_{11}$, $L_{12}$, $L_{13}$ and $L_{14}$ is a direct bond or 1-100, 1-50, 1-25, 1-20, 1-25, 1-10, 1-9, 1-8, 1-7, 1-6, 1-5, 1-4, 1-3, 1-2 or 1 amino acids. In some embodiments, each $L_1$, $L_2$, $L_3$, $L_4$, $L_5$, $L_6$, $L_7$, $L_8$, $L_9$, $L_{10}$, $L_{11}$, $L_{12}$, $L_{13}$ and $L_{14}$ is a direct bond, 1 or 2 amino acids. In some embodiments, any one or more of these linkages are the result of a restriction site used in preparing the nucleic acid sequences encoding the fusion protein. It is understood that this example can be applied to a fusion protein having additional enhancer or antigenic sequences, i.e. can comprise $L_1$, $L_2$ ... $L_m$ such linkages, where numbering is sequential to Lm as needed to describe the fusion proteins. In some embodiments, the entire fusion protein as described herein is less than 3,000 amino acids, less than 2,000 amino acids, between 200 and 3,000 amino acids, between 200 and 2,000 amino acids, between 300 and 2,000 amino acids, between 300 and 1,500 amino acids or between 300 and 1,000 amino acids.

The constructs of the present invention may also comprise one or more additional, non-ActA, residues lying between the C-terminal residue of the modified ActA and the antigen sequence, or between the C-terminal residue of the modified ActA and the first amino acid sequence when the antigen sequence is fused to the amino terminus of the first amino acid sequence. In the following sequences, ActA-N100 is extended by two residues (Gly-Ser) added by inclusion of a BamH1 site (again, the $Val_1Met$ substituted form may also be used) (SEQ ID NO: 26):

```
VGLNRFMRAM MVVFITANCI TINPDIIFAA TDSEDSSLNT DEWEEEKTEE        50

QPSEVNTGPR YETAREVSSR DIEELEKSNK VKNTNKADLI AMLKAKAEKG       100 gs
```

A modified ActA known as ActAN100* may comprise or consist of the following sequence SEQ ID NO: 27 and SEQ ID NO: 28, respectively, which differ only in the first amino acid, per discussion of Val₁Met substitution when expressed by Listeria (dashes indicate deletions and bold text indicates substitutions relative to ActAN100):

```
VGLNRFMRAM MVVFITANCI TINPDIIFAA TDSEDSSLNT DEWEEE----      50
---------- YETAREVSSR DIEELEKSNK VKNTNKADQDNKRKAKAEKG      100
MGLNRFMRAM MVVFITANCI TINPDIIFAA TDSEDSSLNT DEWEEE----      50
---------- YETAREVSSR DIEELEKSNK VKNTNKADQDNKRKAKAEKG      100
```

The DNA and protein sequences used in the antigenic construct are as follows: DNA (SEQ ID NO: 36) expressing the ActAn100* protein SEQ ID NO: 28 when expressed in Listeria (lowercase, not underlined: actA promoter; lowercase, underlined: restriction sites; uppercase, bold: ActAN100* sequence, following which the tested constructs were inserted):

ggtaccgggaagcagttggggttaactgattaacaaatgttagagaaaaa ttaattctccaagtgatattcttaaaataattcatgaatatttttttctta tattagctaattaagaagataattaactgctaatccaatttttaacggaa taaattagtgaaaatgaaggccgaattttccttgttctaaaaaggttgta ttagcgtatcacgaggagggagtataaGTGGGATTAAATAGATTTATGCG

TGCGATGATGGTAGTTTTCATTACTGCCAACTGCATTACGATTAACCCCG

ACATAATATTTGCAGCGACAGATAGCGAAGATTCCAGTCTAAACACAGAT

GAATGGGAAGAAGAATACGAAACTGCACGTGAAGTAAGTTCACGTGATAT

TGAGGAACTAGAAAAATCGAATAAAGTGAAAAATACGAACAAAGCAGACC

AAGATAATAAACGTAAAGCAAAAGCAGAGAAAGGT

Fusion to 5 copies of Syn1 yields the following sequence (SEQ ID NO: 43) (lowercase, not underlined: actA promoter; uppercase, bold: ActAN100* sequence; lowercase, underlined: restriction sites; uppercase underlined: Syn1×5):

gggaagcagttggggttaactgattaacaaatgttagagaaaaattaatt ctccaagtgatattcttaaaataattcatgaatatttttttcttatattag ctaattaagaagataattaactgctaatccaatttttaacggaataaatt agtgaaaatgaaggccgaattttccttgttctaaaaaggttgtattagcg tatcacgaggagggagtataaGTGGGATTAAATAGATTTATGCGTGCGAT

GATGGTAGTTTTCATTACTGCCAACTGCATTACGATTAACCCCGACATAA

TATTTGCAGCGACAGATAGCGAAGATTCCAGTCTAAACACAGATGAATGG

GAAGAAGAATACGAAACTGCACGTGAAGTAAGTTCACGTGATATTGAGGA

ACTAGAAAAATCGAATAAAGTGAAAAATACGAACAAAGCAGACCAAGATA

ATAAACGTAAAGCAAAAGCAGAGAAAGGTggatctGCAAGCAAAGTATTG

CCAGCTAGTCGTGCAGTGGATGATCATCACGCGCAGTTTCTATTATCCGA

AAAAGGATCGTGTGCCGATGGCTCAGTAAAGACTAGCGCGAGCAAAGTGG

CCCCTGCATCACGAGCAGTAGACGACCACCATGCTCAATTCTTACTAAGC

-continued

GAGAAAGGTAGCTGCGGAGATGGTTCAATTAAATTATCAAAAGTCTTACC

AGCATCTAGAGCTGTGGACGATCACCACGCTCAGTTCCTACTATCCGAGA

-continued

AAGGAAGTTGTGCTGACGGAAGTGTTAAAGCGTCGAAAGTAGCTCCAGCT

TCTCGCGCAGTAGATGACCATCATGCGCAATTTTTATTAAGCGAAAAAGG

TAGTTGTGGTGATGGCTCGATCAAATTGTCAAAAGTTCTACCGGCTTCTC

GTGCGGTGGATGATCACCATGCTCAGTTTCTACTAAGCGAGAAAGGCTCT

TGCGCGGATGGTTCCGTTAAA

This translates to the following protein sequence when expressed in *Listeria* (SEQ ID NO: 44) (uppercase, bold: ActAN100* sequence; lowercase, underlined: residues added by restriction sites; uppercase underlined: Syn1×5):

MGLNRFMRAMMVVFITANCITINPDIIFAATDSEDSSLNTDEWEEEYETA

REVSSRDIEELEKSNKVKNTNKADQDNKRKAKAEKGgsASKVLPASRAVD

DHHAQFLLSEKGSCADGSVKTSASKVAPASRAVDDHHAQFLLSEKGSCGD

GSIKLSKVLPASRAVDDHHAQFLLSEKGSCADGSVKASKVAPASRAVDDH

HAQFLLSEKGSCGDGSIKLSKVLPASRAVDDHHAQFLLSEKGSCADGSVK

Fusion to 5 copies of Syn2 yields the following sequence (SEQ ID NO: 45) (lowercase, not underlined: actA promoter; uppercase, bold: ActAN100* sequence; lowercase, underlined: restriction sites; uppercase underlined: Syn2×5):

gggaagcagttggggttaactgattaacaaatgttagagaaaaattaatt ctccaagtgatattcttaaaataattcatgaatatttttttcttatattag ctaattaagaagataattaactgctaatccaatttttaacggaataaatt agtgaaaatgaaggccgaattttccttgttctaaaaaggttgtattagcg tatcacgaggagggagtataaGTGGGATTAAATAGATTTATGCGTGCGAT

GATGGTAGTTTTCATTACTGCCAACTGCATTACGATTAACCCCGACATAA

TATTTGCAGCGACAGATAGCGAAGATTCCAGTCTAAACACAGATGAATGG

GAAGAAGAATACGAAACTGCACGTGAAGTAAGTTCACGTGATATTGAGGA

ACTAGAAAAATCGAATAAAGTGAAAAATACGAACAAAGCAGACCAAGATA

ATAAACGTAAAGCAAAAGCAGAGAAAGGTggatctGCAAGCAAAGTATTG

CCAGCTAGTCGTGCAGGATCGTGTGCCGATGGCTCAGTAAAGACTAGCGC

GAGCAAAGTGGCCCCTGCATCACGAGCAGGTAGCTGCGGAGATGGTTCAA

TTAAATTATCAAAAGTCTTACCAGCATCTAGAGCTGGAAGTTGTGCTGAC

GGAAGTGTTAAAGCGTCGAAAGTAGCTCCAGCTTCTCGCGCAGGTAGTTG

TGGTGATGGCTCGATCAAATTGTCAAAAGTTCTACCGGCTTCTCGTGCGG

GCTCTTGCGCGGATGGTTCCGTTAAA

This translates to the following protein sequence when expressed in *Listeria* (SEQ ID NO: 46) (uppercase, bold: ActAN100* sequence; lowercase, underlined: residues added by restriction sites; uppercase underlined: Syn2×5):

MGLNRFMRAMMVVFITANCITINPDIIFAATDSEDSSLNTDEWEEEYETA

REVSSRDIEELEKSNKVKNTNKADQDNKRKAKAEKGgsASKVLPASRAGS

CADGSVKTSASKVAPASRAGSCGDGSIKLSKVLPASRAGSCADGSVKASK

VAPASRAGSCGDGSIKLSKVLPASRAGSCADGSVK

Fusion to 5 copies of Syn18 yields the following sequence (SEQ ID NO: 47) (lowercase, not underlined: actA promoter; uppercase, bold: ActAN100* sequence; lowercase, underlined: restriction sites; uppercase underlined: Syn18×5):

gggaagcagttggggttaactgattaacaaatgttagagaaaaattaatt ctccaagtgatattcttaaaataattcatgaatattttttcttatattag ctaattaagaagataattaactgctaatccaattttaacggaataaatt agtgaaaatgaaggccgaattttccttgttctaaaaaggttgtattagcg tatcacgaggagggagtataaGTGGGATTAAATAGATTTATGCGTGCGAT

GATGGTAGTTTTCATTACTGCCAACTGCATTACGATTAACCCCGACATAA

TATTTGCAGCGACAGATAGCGAAGATTCCAGTCTAAACACAGATGAATGG

GAAGAAGAATACGAAACTGCACGTGAAGTAAGTTCACGTGATATTGAGGA

ACTAGAAAAATCGAATAAAGTGAAAAATACGAACAAAGCAGACCAAGATA

ATAAACGTAAAGCAAAAGCAGAGAAAGGTggatctGCAAGCAAAGTATTG

GAATCTAATCAAAGCGTAGAGGACAAGCACAATGAGTTCATGTTGACGGA

GTACGGTTCATGTGCCGATGGCTCAGTAAAGACTAGCGCGAGCAAAGTGG

CCGAGTCAAATCAGTCTGTTGAGGACAAACATAATGAGTTCATGTTAACG

GAGTATGGTAGCTGTGGAGATGGTTCAATTAAATTATCAAAAGTCTTAGA

ATCTAATCAGAGCGTTGAGGACAAGCATAATGAGTTCATGTTGACGGAGT

ACGGTTCATGTGCTGACGGAAGTGTTAAAGCGTCGAAAGTAGCTGAATCA

AATCAATCTGTAGAGGACAAACACAATGAATTTATGCTAACAGAATACGG

CAGCTGCGGTGATGGCTCGATCAAATTGTCAAAAGTTTTAGAATCTAACC

AGAGCGTTGAAGATAAGCACAACGAATTTATGTTAACGGAGTACGGTTCA

TGCGCGGATGGTTCCGTTAAA

This translates to the following protein sequence when expressed in *Listeria* (SEQ ID NO: 48) (uppercase, bold: ActAN100* sequence; lowercase, underlined: residues added by restriction sites; uppercase underlined: Syn18×5):

MGLNRFMRAMMVVFITANCITINPDIIFAATDSEDSSLNTDEWEEEYETA

REVSSRDIEELEKSNKVKNTNKADQDNKRKAKAEKGgsASKVLESNQSVE

DKHNEFMLTEYGSCASGSVKTSASKVAESNQSVEDKHNEFMLTEYGSCGD

GSIKLSKVLESNQSVEDKHNEFMLTEYGSCADGSVKASKVAESNQSVEDK

HNEFMLTEYGSCGDGSIKLSKVLESNQSVEDKHNEFMLTEYGSCADGSVK

Alternatively, antigen sequence(s) are preferably expressed fused to a modified amino-terminal portion of the *L. monocytogenes* LLO protein that permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified LLO and (b) one or more antigenic epitopes to be expressed as a fusion protein following the modified LLO sequence. The LLO signal sequence is MKKIMLVFIT LILVSLPIAQ QTEAK (SEQ ID NO: 39). In some embodiments, the promoter is hly promoter. In some embodiments, the fusion protein comprises (c) one or more copies of an enhancer amino acid sequence, each enhancer amino acid sequence independently selected from the group consisting of SEQ ID NO: 1 and SEQ ID NO: 37, or a sequence having at least 90% identity or homology thereto, or a sequence having 1-5 conservative amino acid substitutions thereof.

In some embodiments, the modified LLO comprises a modified form of about the first 441 amino acids of LLO, referred to herein as LLO-N441. LLO-N441 has the following sequence (SEQ ID NO: 40):

```
              10         20         30         40
      MKKIMLVFIT LILVSLPIAQ QTEAKDASAF NKENSISSMA 50         60         70         80
      PPASPPASPK TPIEKKHADE IDKYIQGLDY NKNNVLVYHG 90        100        110        120
      DAVTNVPPRK GYKDGNEYIV VEKKKKSINQ NNADIQVVNA 130        140        150        160
      ISSLTYPGAL VKANSELVEN QPDVLPVKRD SLTLSIDLPG 170        180        190        200
      MTNQDNKIVV KNATKSNVNN AVNTLVERWN EKYAQAYPNV 210        220        230        240
      SAKIDYDDEM AYSESQLIAK FGTAFKAVNN SLNVNFGAIS 250        260        270        280
      EGKMQEEVIS FKQIYYNVNV NEPTRPSRFF GKAVTKEQLQ 290        300        310        320
      ALGVNAENPP AYISSVAYGR QVYLKLSTNS HSTKVKAAFD 330        340        350        360
      AAVSGKSVSG DVELTNIIKN SSFKAVIYGG SAKDEVQIID 370        380        390        400
      GNLGDLRDIL KKGATFNRET PGVPIAYTTN FLKDNELAVI 410        420        430        440
      KNNSEYIETT SKAYTDGKIN IDHSGGYVAQ FNISWDEVNY

D
```

In this sequence, the PEST motif (KENSISSMAPPASP-PASPK, SEQ ID NO: 67) may be functionally deleted by replacement with the following sequence (dashes indicate deletions and bold text indicates substitutions):
KE---------------, or by its complete deletion. This is intended to be exemplary only.

As sequences encoded by one organism are not necessarily codon optimized for optimal expression in a chosen vaccine platform bacterial strain, the present invention also provides nucleic acids that are altered by codon optimized for expressing by a bacterium such as *L. monocytogenes*.

In various embodiments, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 3).

TABLE 3

Optimal codons for expression in *Listeria*.

| | Amino Acid | | | | | | | | |
|---|---|---|---|---|---|---|---|---|---|
| | A | R | N | D | C | Q | E | G | H | I |
| Optimal *Listeria* codon | GCA | CGU | AAU | GAU | UGU | CAA | GAA | GGU | CAU | AUU |

| | Amino Acid | | | | | | | | |
|---|---|---|---|---|---|---|---|---|---|
| | L | K | M | F | P | S | T | W | Y | V |
| Optimal *Listeria* codon | UUA | AAA | AUG | UUU | CCA | AGU | ACA | UGG | UAU | GUU |

The invention supplies a number of *Listeria* species and strains for making or engineering a vaccine platform of the present invention. The *Listeria* of the present invention is not to be limited by the species and strains disclosed in the following table.

Strains of *Listeria* suitable for use in the present invention, e.g., as a vaccine or as a source of nucleic acids.

| | |
|---|---|
| *L. monocytogenes* 10403S wild type. | Bishop and Hinrichs (1987) J. Immunol. 139: 2005-2009; Lauer, et al. (2002) J. Bact. 184: 4177-4186. |
| *L. monocytogenes* DP-L4056 (phage cured). The prophage-cured 10403S strain is designated DP-L4056. | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4029, which is DP-L3078, phage cured, deleted in ActA. | Lauer, et al. (2002) J. Bact. 184: 4177-4186; Skoble, et al. (2000) J. Cell Biol. 150: 527-538. |
| *L. monocytogenes* DP-L4042 (delta PEST) | Brockstedt, et al. (2004) Proc. Natl. Acad. Sci. USA 101: 13832-13837; supporting information. |
| *L. monocytogenes* DP-L4097 (LLO-S44A). | Brockstedt, et al. (2004) Proc. Natl. Acad. Sci. USA 101: 13832-13837; supporting information. |
| *L. monocytogenes* DP-L4364 (delta lplA; lipoate protein ligase). | Brockstedt, et al. (2004) Proc. Natl. Acad. Sci. USA 101: 13832-13837; supporting information. |
| *L. monocytogenes* DP-L4405 (delta inlA). | Brockstedt, et al. (2004) Proc. Natl. Acad. Sci. USA 101: 13832-13837; supporting information. |
| *L. monocytogenes* DP-L4406 (delta inlB). | Brockstedt, et al. (2004) Proc. Natl. Acad. Sci. USA 101: 13832-13837; supporting information. |
| *L. monocytogenes* CS-L0001 (delta ActA-delta inlB). | Brockstedt, et al. (2004) Proc. Natl. Acad. Sci. USA 101: 13832-13837; supporting information. |
| *L. monocytogenes* CS-L0002 (delta ActA-delta lplA). | Brockstedt, et al. (2004) Proc. Natl. Acad. Sci. USA 101: 13832-13837; supporting information. |
| *L. monocytogenes* CS-L0003 (L461T-delta lplA). | Brockstedt, et al. (2004) Proc. Natl. Acad. Sci. USA 101: 13832-13837; supporting information. |
| *L. monocytogenes* DP-L4038 (delta ActA-LLO L461T). | Brockstedt, et al. (2004) Proc. Natl. Acad. Sci. USA 101: 13832-13837; supporting information. |
| *L. monocytogenes* DP-L4384 (S44A-LLO L461T). | Brockstedt, et al. (2004) Proc. Natl. Acad. Sci. USA 101: 13832-13837; supporting information. |

| | |
|---|---|
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Provisional Pat. application Ser. No. 60/490,089 filed Jul. 24, 2003. |
| *L. monocytogenes* EGD. | GenBank Acc. No. AL591824. |
| *L. monocytogenes* EGD-e. | GenBank Acc. No. NC_003210. ATCC Acc. No. BAA-679. |
| *L. monocytogenes* strain EGD, complete genome, segment 3/12 | GenBank Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Provisional Pat. application Ser. No. 60/541,515 filed Feb. 2, 2004; U.S. Provisional Pat. application Ser. No. 60/490,080 filed Jul. 24, 2003. |
| *L. monocytogenes* DP-L4029 deleted in uvrAB treated with a psoralen. | U.S. Provisional Pat. application Ser. No. 60/541,515 filed Feb. 2, 2004. |
| *L. monocytogenes* delta actA delta inlB delta uvrAB | Brockstedt (2005) Nature Medicine and KBMA patent |
| *L. monocytogenes* delta actA delta inlB delta uvrAB treated with psoralen | Brockstedt (2005) Nature Medicine and KBMA patent |
| *L. monocytogenes* delta actA delta inlB delta uvrAB prfA(G155S) | Lauer et al, (2008) Infect. Immun. And WO 2009/143085 |
| *L. monocytogenes* delta actA delta inlB delta uvrAB prfA(G155S) treated with psoralen | Lauer et al, (2008) Infect. Immun. And WO 2009/143085 |
| *L. monocytogenes* ActA−/inlB− double mutant. | Deposited with ATCC on Oct. 3, 2003. Acc. No. PTA-5562. |
| *L. monocytogenes* lplA mutant or hly mutant. | U.S. patent application No. 20040013690 of Portnoy, et al. |
| *L. monocytogenes* DAL/DAT double mutant. | U.S. patent application No. 20050048081 of Frankel and Portnoy. |
| *L. monocytogenes* str. 4b F2365. | GenBank Acc. No. NC_002973. |
| *Listeria ivanovii* | ATCC No. 49954 |
| *Listeria innocua* Clip11262. | GenBank Acc. No. NC_003212; AL592022. |
| *Listeria innocua*, a naturally occurring hemolytic strain containing the PrfA-regulated virulence gene cluster. | Johnson, et al. (2004) Appl. Environ. Microbiol. 70: 4256-4266. |
| *Listeria seeligeri*. | Howard, et al. (1992) Appl. Eviron. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above *Listeria* strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

Targeting antigens to endocytic receptors on professional antigen-presenting cells (APCs) also represents an attractive strategy to enhance the efficacy of vaccines. Such APC-targeted vaccines have an exceptional ability to guide exogenous protein antigens into vesicles that efficiently process the antigen for major histocompatibility complex class I and class II presentation. Efficient targeting not only requires high specificity for the receptor that is abundantly expressed on the surface of APCs, but also the ability to be rapidly internalized and loaded into compartments that contain elements of the antigen-processing machinery. In these embodiments, the antigens of the present invention are provided as fusion constructs that include an immunogenic polypeptide and a desired endocytic receptor-targeting moiety. Suitable APC endocytic receptors include DEC-205, mannose receptor, CLEC9, Fc receptor. This list is not meant to be limiting. A receptor-targeting moiety may be coupled to an antigen polypeptide by recombinant or using chemical crosslinking.

4. Therapeutic Compositions

The compositions described herein, e.g. bacteria engineered to express the fusion protein as described herein for use as a vaccine or cancer immunotherapeutic, can be administered to a host, either alone or in combination with a pharmaceutically acceptable excipient, in an amount sufficient to induce an appropriate immune response. The immune response can comprise, without limitation, specific immune response, non specific immune response, both specific and non specific response, innate response, primary immune response, adaptive immunity, secondary immune response, memory immune response, immune cell activation, immune cell proliferation, immune cell differentiation, and cytokine expression. The vaccines or cancer immunotherapeutics of the present invention can be stored, e.g., frozen, lyophilized, as a suspension, as a cell paste, or complexed with a solid matrix or gel matrix.

In certain embodiments, before or after the subject has been administered an effective dose of a vaccine containing an immunogenic fusion protein of the present invention to prime the immune response, a second vaccine is administered. This is referred to in the art as a "prime-boost" regimen, i.e. where the first administered vaccine primes the immune response, and the second administered vaccine boosts the response. In such a regimen, the compositions and methods of the present invention may be used as the "prime" delivery, as the "boost" delivery, or as both a "prime" and a "boost."

As an example, a first vaccine comprised of killed but metabolically active *Listeria* that encodes and expresses the antigen polypeptide(s) may be delivered as the "prime," and a second vaccine comprised of attenuated (live or killed but metabolically active) *Listeria* that encodes the antigen polypeptide(s) may be delivered as the "boost." It should be understood, however, that each of the prime and boost need not utilize the methods and compositions of the present invention. Rather, the present invention contemplates the use of other vaccine modalities together with the bacterial vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc. This list is not meant to be limiting The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days; about 6 months, and about 1 year after administration of the prime vaccination is initiated. Preferably one or both of the prime and boost vaccination comprises delivery of a composition of the present invention.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof. In a preferred embodiment, administration is intravenous administration.

Administration of the vaccine and cancer immunotherapeutics of the present invention by a non oral route can avoid tolerance. Methods are known in the art for administration intravenously, subcutaneously, intramuscularly, intraperitoneally, orally, mucosally, by way of the urinary tract, by way of a genital tract, by way of the gastrointestinal tract, or by inhalation.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The bacteria of the present invention can be administered in a dose, or dosages, where each dose comprises at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU), the equivalent of CFU prior to psoralen treatment, or where the units are number of bacterial cells.

The bacteria of the present invention can be administered in a dose, or dosages, where each dose comprises between $10^7$ and $2 \times 10^{15}$ CFU per 70 kg body weight (or per 1.7 square meters surface area; or per 1.5 kg liver weight); between $10^7$ and $10^{11}$ CFU per 70 kg body weight (or per 1.7 square meters surface area; or per 1.5 kg liver weight); between $10^8$ and $10^{10}$ CFU per 70 kg body weight (or per 1.7 square meters surface area; or per 1.5 kg liver weight); between $10^7$ and $10^8$ CFU per 70 kg body weight (or per 1.7 square meters surface area; or per 1.5 kg liver weight); between $2 \times 10^7$ and $2 \times 10^8$ CFU per 70 kg body weight (or per 1.7 square meters surface area; or per 1.5 kg liver weight); between $5 \times 10^7$ and $5 \times 10^8$ CFU per 70 kg body weight (or per 1.7 square meters surface area; or per 1.5 kg liver weight); between $10^8$ and $10^9$ CFU per 70 kg body weight (or per 1.7 square meters surface area; or per 1.5 kg liver weight); between $2 \times 10^8$ and $2 \times 10^9$ CFU per 70 kg (or per 1.7 square meters surface area, or per 1.5 kg liver weight); between $5 \times 10^8$ to $5 \times 10^9$ CFU per 70 kg (or per 1.7 square meters surface area, or per 1.5 kg liver weight); between $10^9$ and $10^{10}$ CFU per 70 kg (or per 1.7 square meters surface area, or per 1.5 kg liver weight); between $2 \times 10^9$ and $2 \times 10^{10}$ CFU per 70 kg (or per 1.7 square meters surface area, or per 1.5 kg liver weight); between $5 \times 10^9$ and $5 \times 10^{10}$ CFU per 70 kg (or per 1.7 square meters surface area, or per 1.5 kg liver weight); between $10^{11}$ and $10^{12}$ CFU per 70 kg (or per 1.7 square meters surface area, or per 1.5 kg liver weight); between $2 \times 10^{11}$ and $2 \times 10^{12}$ CFU per 70 kg (or per 1.7 square meters surface area, or per 1.5 kg liver weight); between $5 \times 10^{11}$ and $5 \times 10^{12}$ CFU per 70 kg (or per 1.7 square meters surface area, or per 1.5 kg liver weight); between $10^{12}$ and $10^{13}$ CFU per 70 kg (or per 1.7 square meters surface area); between $2 \times 10^{12}$ and $2 \times 10^{13}$ CFU per 70 kg (or per 1.7 square meters surface area, or per 1.5 kg liver weight); between $5 \times 10^{12}$ and $5 \times 10^{13}$ CFU per 70 kg (or per 1.7 square meters surface area, or per 1.5 kg liver weight); between $10^{13}$ and $10^{14}$ CFU per 70 kg (or per 1.7 square meters surface area, or per 1.5 kg liver weight); between $2 \times 10^{13}$ and $2 \times 10^{14}$ CFU per 70 kg (or per 1.7 square meters surface area, or per 1.5 kg liver weight); $5 \times 10^{13}$ and $5 \times 10^{14}$ CFU per 70 kg (or per 1.7 square meters surface area, or per 1.5 kg liver weight); between $10^{14}$ and $10^{15}$ CFU per 70 kg (or per 1.7 square meters surface area, or per 1.5 kg liver weight); between $2 \times 10^{14}$ and $2 \times 10^{15}$ CFU per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering bacteria, e.g. *Listeria* that is oral. Also provided is a method of administering *Listeria* that is intravenous. Moreover, what is provided is a method of administering *Listeria* that is oral, intramuscular, intravenous, intradermal and/or subcutaneous. The invention supplies a *Listeria* bacterium, or culture or suspension of *Listeria* bacteria, prepared by growing in a medium that is meat based, or that contains polypeptides derived from a meat or animal product. Also supplied by the present invention is a *Listeria* bacterium, or culture or suspension of *Listeria* bacteria, prepared by growing in a medium that does not contain meat or animal products, prepared by growing on a medium that contains vegetable polypeptides, prepared by growing on a medium that is not based on yeast products, or prepared by growing on a medium that contains yeast polypeptides.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Additional agents that are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response that preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide that is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

In an embodiment of the invention, a bacteria of the invention is administered in association with one or more additional pharmaceutically active components selected from the group consisting of an immune checkpoint inhibitor (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MEDI4736, or avelumab); a TLR agonist (e.g. CpG or monophosphoryl lipid A); an inactivated or attenuated bacteria that induce innate immunity (e.g., inactivated or attenuated *Listeria monocytogenes*); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent. In some embodiments, the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist. In some embodiments, the immune checkpoint inhibitor is an anti-PD-1 antibody, an anti-PD-L1 antibody, an anti-CTLA-4 antibody, an anti-TIM-3 antibody, an anti-BTLA antibody, an anti-B7-H3 antibody, an anti-CD70 antibody, an anti-CD40 antibody, an anti-CD137 antibody, an anti-GITR antibody, an anti-OX40 antibody, an anti-KIR antibody or an anti-LAG-3 antibody. In some embodiments, the immune checkpoint inhibitor is selected from the group consisting of nivolumab, pembrolizumab, pidilizumab, PDR001, MEDI0680, REGN2810, AMP-224, ipilimumab, BMS-936559, MPDL3280A, MEDI4736, and avelumab. In some embodiments, the TLR agonist is CpG or monophosphoryl lipid A.

In an embodiment of the invention, a bacteria of the invention is administered in association with a STING agonist. This administration may be separate, or may be preferably as part of a single pharmaceutical composition. The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells that activates the TANK binding kinase (TBK1)-IRF3 and the NF-κB signaling axis, resulting in the induction of IFN-β and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific CD4+ and CD8+ T cells as well as pathogen-specific antibodies. Examples of cyclic purine dinucleotides are described in some detail in, for example: U.S. Pat. Nos. 7,709,458 and 7,592,326; PCT Publication Nos. WO2007/054279, WO2014/093936, WO2014/179335, WO2014/189805, WO2015/185565, WO2016/096174, WO2016/145102, WO2017/027645, WO2017/027646, and WO2017/075477; and Yan et al., Bioorg. Med. Chem Lett. 18:5631-4, 2008.

In an embodiment of the invention, a bacteria of the invention is administered in association with one or more immune checkpoint inhibitors selected from the group consisting of an anti-PD-1 antibody, an anti-PD-L$_1$ antibody, an anti-CTLA-4 antibody, an anti-TIM-3 antibody, an anti-BTLA antibody, an anti-B7-H3 antibody, an anti-CD70 antibody, an anti-CD40 antibody, an anti-CD137 antibody, an anti-GITR antibody, an anti-OX40 antibody, an anti-KIR antibody or an anti-LAG-3 antibody. In some embodiments, the bacteria of the invention is administered in association with an anti-CTLA-4 antibody and/or an anti-PD-1 antibody.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available. See, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) ActA Clin. Belg. 56:209-219; Greiner, et al. (2002) Cancer Res. 62:6944-6951; Smith, et al. (2003) J. Med. Virol. 70: Suppl. 1: S38-541; Sepulveda-Amor, et al. (2002) Vaccine 20:2790-2795).

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

"Vaccine" encompasses preventative vaccines. Vaccine also encompasses therapeutic vaccines, e.g., a vaccine administered to a mammal that comprises a condition or disorder associated with the antigen or epitope provided by the vaccine. A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. See, e.g., WO04/006837; WO04/084936; WO04/110481; WO05/037233; WO05/092372; WO06/036550; WO08/109155; WO08/130551; WO08/140812; WO09/143085; WO09/143167; WO10/040135; WO11/060260; WO07/103225; WO07/117371; and WO14/074635, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, *L. monocytogenes* provides a preferred vaccine platform for expression of the antigens of the present invention.

5. Preferred Embodiments

The following are preferred embodiments of the present invention, and are exemplary in nature.

Embodiment 1

A nucleic acid molecule that encodes a fusion protein, wherein said fusion protein comprises (i) a first amino acid sequence comprising one or more copies of an enhancer amino acid sequence, each enhancer amino acid sequence independently selected from the group consisting of SEQ ID NO: 1 or a sequence having 1-5 conservative amino acid substitutions thereof and SEQ ID NO: 37 or a sequence having 1-5 conservative amino acid substitutions thereof, and (ii) a second amino acid sequence encoding a polypeptide of interest linked to the amino terminus or carboxyl terminus of the first amino acid sequence.

Embodiment 2

The nucleic acid molecule according to embodiment 1, further comprising one or more regulatory elements that mediate expression, and optionally secretion, of the fusion protein in a host cell.

Embodiment 3

The nucleic acid molecule according to embodiment 2, wherein the regulatory elements comprise a *Listeria monocytogenes* actA promoter.

Embodiment 4

The nucleic acid molecule according to embodiment 1, wherein the polypeptide of interest comprises a tumor antigen.

Embodiment 5

The nucleic acid molecule according to embodiment 1, wherein the first amino acid sequence comprises one or more cleaver amino acid sequences, wherein each cleaver amino acid sequence is independently selected and linked to at least one of the one or more enhancer amino acid sequences.

Embodiment 6

The nucleic acid molecule according to embodiment 5, wherein each enhancer amino acid sequence is linked to an independently selected cleaver amino acid sequence at its amino terminus and an independently selected cleaver amino acid sequence at its carboxy terminus.

Embodiment 7

The nucleic acid molecule according to embodiment 6 wherein the first amino acid sequence comprises 1, 2, 3, 4 or 5 copies of SEQ ID NO: 1 or 1, 2, 3, 4 or 5 copies of SEQ ID NO: 37.

Embodiment 8

The nucleic acid molecule according to embodiment 7, wherein each cleaver amino acid sequence linked to an enhancer amino acid sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

Embodiment 9

The nucleic acid molecule according to embodiment 1, wherein the first amino acid sequence is selected from the group consisting of SEQ ID NO: 31, SEQ ID NO: 29, SEQ ID NO: 69, SEQ ID NO: 70, SEQ ID NO: 71, SEQ ID NO: 72, SEQ ID NO: 73, SEQ ID NO: 74, SEQ ID NO: 35, and SEQ ID NO: 33.

Embodiment 10

The nucleic acid molecule according to embodiment 1, wherein the first amino acid sequence is SEQ ID NO: 35.

Embodiment 11

The nucleic acid molecule according to one of embodiments 1-10, wherein the second amino acid sequence comprises one or more independent antigenic sequences.

Embodiment 12

The nucleic acid molecule according to embodiment 11, wherein the second amino acid sequence comprises one or more cleaver amino acid sequences, wherein each cleaver amino acid sequence is independently selected and linked to at least one of the one or more antigenic sequences.

Embodiment 13

The nucleic acid molecule according to embodiment 12, wherein each independent antigenic sequence is linked to an independently selected cleaver amino acid sequence at its amino terminus and an independently selected cleaver amino acid sequence at its carboxy terminus.

Embodiment 14

The nucleic acid molecule according to embodiment 13, wherein each cleaver amino acid sequence linked to an antigenic sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

Embodiment 15

The nucleic acid molecule according to one of embodiments 1-14, wherein the fusion protein comprises a secretory signal sequence.

Embodiment 16

The nucleic acid molecule according to embodiment 15, wherein the carboxy terminus of said secretory signal sequence is linked to the amino terminus of the first amino acid sequence, and the carboxy terminus of the first amino acid sequence is linked to the amino terminus of the second amino acid sequence.

Embodiment 17

The nucleic acid molecule according to embodiment 15, wherein the carboxy terminus of said secretory signal sequence is linked to the amino terminus of the second amino acid sequence, and the carboxy terminus of the second amino acid sequence is linked to the amino terminus of the first amino acid sequence.

Embodiment 18

The nucleic acid molecule according to one of embodiments 16 or 17, wherein the secretory signal sequence is a *Listeria monocytogenes* secretory signal sequence.

Embodiment 19

The nucleic acid molecule according to embodiment 18, wherein the secretory signal sequence is an ActA or LLO secretory signal sequence.

Embodiment 20

The nucleic acid molecule according to embodiment 19, wherein the ActA signal sequence is encoded by a sequence selected from the group consisting of SEQ ID NO: 25, SEQ ID NO: 26, SEQ ID NO: 27, and SEQ ID NO: 28, or an amino acid sequence having at least 90% sequence identity thereto, or the LLO signal sequence is encoded by a sequence selected from the group consisting of SEQ ID NO: 40, SEQ ID NO: 40 from which the sequence SEQ ID NO: 67 is deleted, and SEQ ID NO: 40 in which the sequence SEQ ID NO: 67 is replaced with KE, or an amino acid sequence having at least 90% sequence identity thereto.

Embodiment 21

The nucleic acid molecule according to embodiment 19, wherein the secretory signal sequence is SEQ ID NO:28, or an amino acid sequence having at least 90% sequence identity thereto.

Embodiment 22

A host cell comprising the nucleic acid molecule of one of embodiments 1-21 integrated into the genome of the host cell, wherein the host cell expresses the fusion protein.

Embodiment 23

The host cell of embodiment 22, wherein the host cell is a bacterium.

Embodiment 24

The host cell of embodiment 23, wherein the bacterium is *Listeria monocytogenes*.

Embodiment 25

The host cell of embodiment 24, wherein the nucleic acid molecule is integrated into a virulence gene of *Listeria monocytogenes*, wherein the integration of said nucleic acid molecule disrupts expression of the virulence gene or disrupts a coding sequence of the virulence gene.

Embodiment 26

The host cell of embodiment 25, wherein the virulence gene is actA or inlB.

Embodiment 27

A composition comprising the host cell according to one of embodiments 22-26 and a pharmaceutically acceptable excipient.

Embodiment 28

A method of expressing a polypeptide of interest from a host cell, comprising:
introducing into the host cell an expression construct comprising the nucleic acid molecule according to one of embodiments 1-21, wherein the fusion protein is operably linked to one or more regulatory elements which mediate expression, and optionally secretion, of the fusion protein in the host cell.

Embodiment 29

The method according to embodiment 28, wherein the host cell is a bacterium.

Embodiment 30

The method according to embodiment 29, wherein the host cell is a *Listeria monocytogenes* bacterium.

Embodiment 31

The method according to embodiment 30, wherein the expression construct is integrated into the genome of the *Listeria monocytogenes*.

Embodiment 32

The method according to embodiment 31, wherein the expression construct is integrated into a virulence gene of the *Listeria monocytogenes*, and the integration of said nucleic acid molecule disrupts expression of the virulence gene or disrupts a coding sequence of the virulence gene.

Embodiment 33

A method according to embodiment 32, wherein the virulence gene is *Listeria monocytogenes* actA or inlB.

Embodiment 34

A fusion protein comprising:
a first amino acid sequence comprising one or more copies of an enhancer amino acid sequence, each enhancer amino acid sequence independently selected from the group consisting of SEQ ID NO: 1 or a sequence having 1-5 conservative amino acid substitutions thereof and SEQ ID NO: 37 or a sequence having 1-5 conservative amino acid substitutions thereof, and (ii) a second amino acid sequence encoding a polypeptide of interest linked to the amino terminus or carboxyl terminus of the first amino acid sequence.

Embodiment 35

The fusion protein according to embodiment 34, wherein the polypeptide of interest comprises a tumor antigen.

Embodiment 36

The fusion protein according to embodiment 34, wherein the first amino acid sequence comprises one or more cleaver amino acid sequences, wherein each cleaver amino acid sequence is independently selected and linked to at least one of the one or more enhancer amino acid sequences.

Embodiment 37

The fusion protein according to embodiment 36, wherein each enhancer amino acid sequence is linked to an independently selected cleaver amino acid sequence at its amino terminus and an independently selected cleaver amino acid sequence at its carboxy terminus.

Embodiment 38

The fusion protein according to embodiment 37, wherein the first amino acid sequence comprises 1, 2, 3, 4 or 5 copies of SEQ ID NO: 1 or 1, 2, 3, 4 or 5 copies of SEQ ID NO: 37.

Embodiment 39

The fusion protein according to embodiment 38, wherein each cleaver amino acid sequence linked to an enhancer amino acid sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

Embodiment 40

The fusion protein according to embodiment 34, wherein the first amino acid sequence is selected from the group consisting of SEQ ID NO: 31, SEQ ID NO: 29, SEQ ID NO: 69, SEQ ID NO: 70, SEQ ID NO: 71, SEQ ID NO: 72, SEQ ID NO: 73, SEQ ID NO: 74, SEQ ID NO: 35, and SEQ ID NO: 33.

Embodiment 41

The fusion protein according to embodiment 34, wherein the first amino acid sequence is SEQ ID NO: 35.

Embodiment 42

The fusion protein according to one of embodiments 34-41, wherein the second amino acid sequence comprises one or more independent antigenic sequences.

Embodiment 43

The fusion protein according to embodiment 42, wherein the second amino acid sequence comprises one or more cleaver amino acid sequences, wherein each cleaver amino acid sequence is independently selected and linked to at least one of the one or more antigenic sequences.

Embodiment 44

The fusion protein according to embodiment 43, wherein each independent antigenic sequence is linked to an independently selected cleaver amino acid sequence at its amino terminus and an independently selected cleaver amino acid sequence at its carboxy terminus.

Embodiment 45

The fusion protein according to embodiment 44, wherein each cleaver amino acid sequence linked to an antigenic sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

Embodiment 46

The fusion protein according to one of embodiments 34-45, wherein the fusion protein comprises a secretory signal sequence.

Embodiment 47

The fusion protein according to embodiment 46, wherein the carboxy terminus of said secretory signal sequence is linked to the amino terminus of the first amino acid sequence, and the carboxy terminus of the first amino acid sequence is linked to the amino terminus of the second amino acid sequence.

Embodiment 48

The fusion protein according to embodiment 46, wherein the carboxy terminus of said secretory signal sequence is linked to the amino terminus of the second amino acid sequence, and the carboxy terminus of the second amino acid sequence is linked to the amino terminus of the first amino acid sequence.

Embodiment 49

The fusion protein according to one of embodiments 47 or 48, wherein the secretory signal sequence is a *Listeria monocytogenes* secretory signal sequence.

Embodiment 50

The fusion protein according to embodiment 49, wherein the secretory signal sequence is an ActA or LLO secretory signal sequence.

Embodiment 51

The fusion protein according to embodiment 50, wherein the ActA signal sequence is encoded by a sequence selected from the group consisting of SEQ ID NO: 25, SEQ ID NO: 26, SEQ ID NO: 27, and SEQ ID NO: 28, or an amino acid sequence having at least 90% sequence identity thereto, or the LLO signal sequence is encoded by a sequence selected from the group consisting of SEQ ID NO: 40, SEQ ID NO: 40 from which the sequence SEQ ID NO: 67 is deleted, and SEQ ID NO: 40 in which the sequence SEQ ID NO: 67 is replaced with KE, or an amino acid sequence having at least 90% sequence identity thereto.

Embodiment 52

The fusion protein according to embodiment 50, wherein the secretory signal sequence is SEQ ID NO:28, or an amino acid sequence having at least 90% sequence identity thereto.

Embodiment 53

A method of treating cancer or a viral disease in an individual in need thereof, comprising:
expressing a fusion protein according to one of embodiments 34-52 within the individual, wherein the polypeptide of interest comprises one or more independent antigenic sequences present on cancer cells or virally infected cells present in the individual.

Embodiment 54

The method according to embodiment 53, wherein the fusion protein is expressed from a host cell comprising a nucleic acid molecule of one of claims 1-21.

Embodiment 55

The method according to embodiment 54, wherein the host cell is a host cell of one of claims 22-26.

EXAMPLES

The following examples serve to illustrate the present invention. These examples are in no way intended to limit the scope of the invention.

Example 1: General Methods Used Throughout the Examples

All synthetic expression/secretion enhancers were engineered as translational fusions downstream of the modified amino terminal domain of the *Listeria* protein ActA termed ActAN100* and under the control of the ActA promoter. These full length (five copy) promoter-enhancer sequences were synthesized and codon optimized for expression in *Listeria* by DNA2.0 (Menlo Park, Calif.). These full length leader sequences were subcloned into a derivative of the pPL2 shuttle vector using standard restriction enzyme-based cloning methods as translational fusions to a set of previously sequence-confirmed antigens; Ig1C, PAP (33-386), mesothelin (35-622), mesothelin (35-609), and the fusion of two HBV antigens, Pol (1-300) and X-Ag. Initial cloning steps were performed in $XL_1$-Blue cells (Agilent, Santa Clara, Calif.) using T4 DNA ligase (NEB, Ipswich, Mass.). The pINT vector allows conjugation from the *E. coli* strain SM10 (competent cells prepped in house, Zymo Research, Irvine Calif.) into *Listeria* and facilitates site specific integration at the $tRNA^{Arg}$ locus. All enhancers were assessed in the *Listeria* vaccine strain Lm11 (ΔactAΔinlB). For enhancers with fewer copies, PCR was used to amplify the appropriate length product (Phusion polymerase, NEB, Ipswich Mass.). PCR products were cleaned up through purification columns (Qiagen, Germantown, Md.), cloned using restriction enzymes and sequence confirmed. All strains assessed for expression/secretion and immunogenicity are shown in Table 1.

Western Blots

Overnight cultures (1 ml) of *Listeria* strains inoculated from glycerol stocks were grown without shaking in Brain Heart Infusion broth (BD) at 30° C. DC2.4 cells were stored in 10% DMSO in fetal bovine serum (FBS) in liquid nitrogen. One day prior to infection, DC2.4 cells ($4 \times 10^6$ cells per vial) were thawed, rinsed once with complete RPMI media (RPMI, 10% FBS, non-essential amino acids, L-glutamine, sodium pyruvate, HEPES buffer and 2-mercaptoethanol) without antibiotics, resuspended in the same media, seeded at $1.5 \times 10^5$ cells per well in 24 well plates and incubated at 37° C. (5% $CO_2$) overnight.

The overnight bacterial cultures described above were diluted 1:200 (5 µl in 1 ml) in complete RPMI media without antibiotics and mixed well by repeated pipetting. Media from DC2.4 cells plated the previous day was aspirated, and overnight culture dilutions (300 µl; $3 \times 10^6$ bacteria) were used to infect individual wells containing DC2.4 cells (multiplicity of infection of 20). Infections were allowed to proceed at 37° C. (5% $CO_2$) for 1 hour, supernatants were removed by aspiration, wells were rinsed one time with PBS (2 ml) and complete RPMI media containing 50 µg/ml gentamycin was added (2 ml). Infections were incubated seven additional hours at 37° C. (5% $CO_2$).

For Western blotting, used in the examples below unless otherwise indicated, media was removed by aspiration and cells were washed with PBS (1 ml) and collected by the addition of lysis buffer (100 µl 1×LDS buffer with reducing agent; Life Technologies) and physical disruption. Lysates were transferred to 1.5 ml tubes, incubated at 95° C. for 10 min, vortexed and stored at −20° C. For broth-based Western blot analysis, as indicated in the examples below, overnight cultures (1 ml) of *Listeria* strains were grown in yeast media (YNG) broth at 37° C. shaking ~200 rpm overnight. The culture media was then isolated by centrifugation of the bacteria. An aliquot of media (50 µl) was transferred to a separate tube and 4× loading dye (20 µl; Novex) and 10× reducing agent (8 µl; Novex) were added. Samples were incubated at 95° C. for 10 min, vortexed and stored at −20° C.

Aliquots (20 µl) were run on 4-12% Bis-Tris PAGE gels in 1×MES buffer (Invitrogen) and transferred to 0.45 µm nitrocellulose membranes for detection. Membranes were blocked for 1 hour at room temperature in Odyssey blocking buffer (Li-Cor). Heterologous antigens were detected using the A18K polyclonal rabbit antibody (1:4,000 dilution) that recognizes the mature 18 amino acid amino terminus of the ActA protein, which is fused to the N-terminus of each antigen. The constitutively expressed *Listeria* p60 protein was used as a control for the number of bacteria loaded per sample and was detected using a mouse monoclonal p60 antibody (1:4,000; AdipoGen Life Sciences). Differentially labeled goat anti-mouse and goat anti-rabbit (IRDyes 800CW and 680RD, respectively; Odyssey) secondary antibodies were used at 1:10,000 dilutions. All antibodies were diluted in Odyssey blocking buffer with 0.2% Tween. Membranes were incubated with both primary antibodies overnight at 4° C., washed three times for five minutes each wash with PBS containing 0.1% Tween, then incubated with secondary antibodies for 1 hour at room temperature. Membranes were washed a further four times, the last wash with PBS only, then scanned using a Li-Cor Odyssey system.

Western blots were quantitated with Li-Cor Image Studio software. Individual antigen or p60 bands were boxed on images representing the appropriate signal (i.e., 680 nm or 800 nm wavelength scans for ActAN100* or p60, respectively), and the total intensity within each box was determined. Intensity measurements were exported to Excel where the ratio of ActAN100* intensity to p60 intensity was calculated.

Immunogenicity Experiments

Bacterial cultures were grown in YNG media overnight shaking at 37° C. to stationary phase. The following day, cultures were diluted in sterile HBSS to an approximate concentration of 2.5×10$^7$ CFU/mL. 6-8 week old Balb/c mice (n=5) received approximate dose as indicated in the examples below (e.g. 5×10$^6$ CFU) by intravenous injection with 200 μL volume in the lateral tail vein. Seven days post immunization, spleens were harvested and single cell suspensions were prepared for T-cell analysis by IFNγ ELISpot analysis. 4×10$^5$ splenocytes per well were stimulated overnight with a PAP peptide pool composed of 94 15mer peptides overlapping by 11 amino acids or with media only (unstimulated control). The following day, PAP-specific T-cell responses were quantified by IFNγ ELISpot and statistical significance was determined using GraphPad Prism to perform two-tailed unpaired t test analysis where P<0.05. A similar assay was used to assess immunogenicity of HBV Pol$_{1-300}$-HBxAg expressing strains, where stimulation with HBV-Pol$_{140-148}$ to assess HBV-Pol$_{140-148}$ specific T-cell responses by IFNγ ELISpot.

Sequences Used

Single repeat units of an EGFRvIII sequence, and synthetic syn1, syn2, and syn18 modifications thereof were used in the following examples. Underlined is a complete EGFRvIII repeat unit used as a control sequence in the EGFRvIII sequence and the remaining portions in syn1, syn2 and syn18. The EGFRvIII neo-antigen HLA-A2 restricted T cell epitope is shown in bold. Syn1 alters 13 of 21 amino acids in the repeat unit that span the entire EGFRvIII T cell epitope. Syn2 deletes the same 13 amino acids (depicted as dashes) from the basic repeat. Syn18 alters 15 of 21 amino acids in the repeat unit. The variants were designed to avoid significant homology to any proteins in the human genome, as determined by BLASTp searches. Included in these sequences are amino terminal (ASKVL) (SEQ ID NO: 5) and carboxy terminal (ADGSVK) (SEQ ID NO: 2) proteasome cleavage sequences (italics).

```
                                         (SEQ ID NO: 17)
EGFRvIII    ASKVLPASRALEEKKGNYVVTDHGSCADGSVK (SEQ ID NO: 29)
syn1        ASKVLPASRAVDDHHAQFLLSEKGSCADGSVK (SEQ ID NO: 30)
syn2        ASKVLPASRA-------------GSCADGSVK (SEQ ID NO: 31)
syn18       ASKVLESNQSVEDKHNEFMLTEYGSCADGSVK
```

Alignment of "5 copy" Syn1 (SEQ ID NO: 33), Syn 2 (SEQ ID NO: 34) and Syn18 (SEQ ID NO: 35) sequence to a 5 copy EGFRvIII construct (SEQ ID NO: 32):

Example 2: Effect on PAP Expression by EGFRvIII, Syn1, Syn2, and Syn18 Expression Enhancer Sequences As shown in the following example, expression of the cancer antigen prosthetic acid phosphatase (PAP) is dramatically enhanced when fused to EGFRvIII, syn1, and syn18 expression enhancer sequences.

The following constructs were tested. As shown in FIG. 1, ActAN100* (SEQ ID NO: 28, shown in black) was fused in-frame to five copies of four different repeats, followed by residues 33-386 of human PAP.
BH2869: No enhancer sequence
BH4703: 5× EGFRvIII (brick pattern)
BH5144: 5× syn1 (diagonal cross hatch)
BH5150: 5× syn2 (horizontal cross hatch),
BH5337: 5× syn18 (checker pattern).

PAP$_{33-386}$ nucleic acid sequence (SEQ ID NO: 51):

```
aaagaactaaagtttgtaacgttagtctttagacatggtgatcgtagtcc tattgatacctttcctacagatccaatcaaagagagtagttggccacaag gcttcggacaacttacacaattaggaatggaacaacattatgaattaggt gaatacattcgcaaacgttatcgcaaattccttaatgaatcgtacaaaca cgaacaagtgtatatccgttccactgacgttgatagaacactaatgtcag ctatgacaaatctagctgcattagtgccaccagaaggcgttagcatttgg aatcctatcttactttggcagccaatacctgtacatacggttccgttatc tgaagatcaattactttatcttccatttcgcaactgcccacgattccaag aattagaatccgaaacattgaaaagcgaagaatttcagaaaagattacat ccatacaaagactttatcgcaaccttaggcaaattgtcagggttacacgg acaggatctatttggaatttggtcgaaagtttatgatcctttgtactgtg aatctgtacataactttacattacctagtcgcgccacggaagatactatg acgaaactacgtgaactttccgaactttctttactatcgttgtatggtat tcataaacaaaaagaaaagagcagattgcaaggtggtgttttagtaaatg aaatcttaaaccatatgaaaagagctacacaaattccgtcttacaagaaa ttgattatgtatagtgctcatgatacgacagtatctgggcttcaaatggc gttagatgtctataacggcttacttccaccgtatgcgtcatgtcaccttta cggaactttactttgagaaaggtgagtactttgttgagatgtactatcgc
```

```
            1                                                           60
EGFRvIII    ASKVLPASRALEEKKGNYVVTDHGSCADGSVKTSASKVAPASRALEEKKCNYVVTDHGSC
Syn1        ASKVLPASRAVDDHHAQFLLSEKGSCADGSVKTSASKVAPASRAVDDHHAQFLLSEKGSC
syn2        ASKVLPASRA-------------GSCADGSVKTSASKVAPASRA-------------GSC
syn18       ASKVLESNQSVEDKHNEFMLTEYGSCADGSVKTSASKVAESNQSVEDKHNEFMLTEYGSC 61                                                          120
EGFRvIII    GDGSIKLSKVLPASRALEEKKGNYVVTDHGSCADGSVKASKVAPASRALEEKKGNYVVTD
syn1        GDGSIKLSKVLPASRAVDDHHAQFLLSEKGSCADGSVKASKVAPASRAVDDHHAQFLLSE
syn2        GDGSIKLSKVLPASRA-------------GSCADGSVKASKVAPASRA------------
syn18       GDGSIKLSKVLESNQSVEDKHNEFMLTEYGSCADGSVKASKVAESNQSVEDKHNEFMLTE 121                          162
EGFRvIII    HGSCGDGSIKLSKVLPASRALEEKKGNYVVTDHGSCADGSVK
syn1        KGSCGDGSIKLSKVLPASRAVDDHHAQFLLSEKGSCADGSVK
syn2        -GSCGDGSIKLSKVLPASRA-------------GSCADGSVK
syn18       YGSCGDGSIKLSKVLESNQSVEDKHNEFMLTEYGSCADGSVK
```

-continued
```
aatgaaacccaacatgaaccatatccgttgatgttaccaggttgtagtcc atcttgcccgttagaacgatttgcggaattagtgggtccagtgataccac aagactggtctactgagtgtatgactactaatagccaccaagggactgaa gattcaacagat
```

PAP$_{33-386}$ protein sequence (SEQ ID NO: 52):

KELKFVTLVFRHGDRSPIDTFPTDPIKESSWPQGFGQLTQLGMEQHYELG

EYIRKRYRKFLNESYKHEQVYIRSTDVDRTLMSAMTNLAALVPPEGVSIW

NPILLWQPIPVHTVPLSEDQLLYLPFRNCPRFQELESETLKSEEFQKRLH

PYKDFIATLGKLSGLHGQDLFGIWSKVYDPLYCESVHNFTLPSRATEDTM

TKLRELSELSLLSLYGIHKQKEKSRLQGGVLVNEILNHMKRATQIPSYKK

LIMYSAHDTTVSGLQMALDVYNGLLPPYASCHLTELYFEKGEYFVEMYYR

NETQHEPYPLMLPGCSPSCPLERFAELVGPVIPQDWSTECMTTNSHQGTE

DSTD

The mouse dendritic cell line DC2.4 was infected with Lm ΔactA/ΔinlB in which the fusion protein was inserted into the chromosomal tRNA$^{Arg}$ locus. Seven hours later, cells were washed, lysed, run on SDS-PAGE, and transferred to nitrocellulose. The Western blot was probed with a rabbit polyclonal antibody raised to the amino terminus of the ActA protein and expression level was normalized to the *Listeria* P60 protein, which correlates with bacterial counts in infected cells. High levels of the fusion construct were expressed by both the research and clinical strains. Expression was normalized using P60 expression, which correlates with bacterial counts in infected cells. Relative expression is set arbitrarily at 1 for the lowest expressing construct; n.a.: not applicable; n.d.: not detected.

Figure 2:
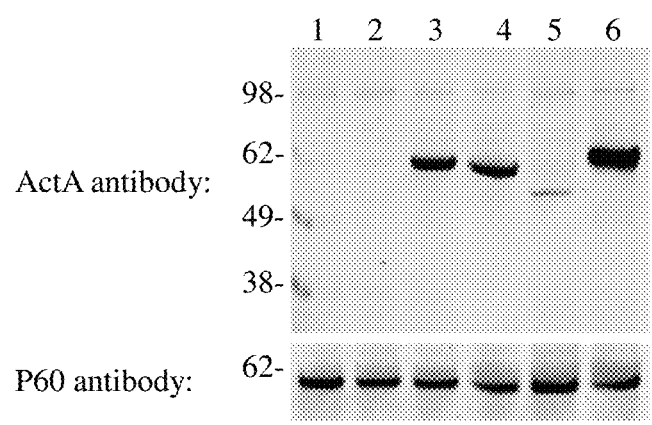
FIG. 2 depicts intracellular Western blot results for fusion protein expression by *Listeria monocytogenes* strains BH2869, BH4703, BH5144, BH5150, and BH5337.

FIG. 2 shows intracellular Western blot results for the fusion protein expression. Efficient augmentation of fusion protein expression was improved with the complete repeat unit, and was not dramatically enhanced due to the spacer (cleaver) sequences (see lane 5, construct that uses syn2). The fusion protein composed of ActAN100*-syn18-PAP$_{33-386}$ resulted in the highest protein expression (lane 6, strain BH5337). Relative expression based on the ActA/p60 ratio is set arbitrarily at 1 for the lowest expressing construct; n.a.: not applicable; n.d.: not detected. This is summarized in the following table:

| Lane | Strain | Expression cassette | Predicted kDa | Relative expression |
| --- | --- | --- | --- | --- |
| 1 | Lm11 | none | n.a. | n.a. |
| 2 | BH2869 | ActAN100-PAP$_{33-386}$ | 48.3 | n.d. |
| 3 | BH4703 | ActAN100*-EGFRvIII-PAP$_{33-386}$ | 66.5 | 14.2 |
| 4 | BH5144 | ActAN100*-Syn1-PAP$_{33-386}$ | 66.5 | 19.1 |
| 5 | BH5150 | ActAN100*-Syn2-PAP$_{33-386}$ | 57.8 | 1.0 |
| 6 | BH5337 | ActAN100*-Syn18-PAP$_{33-386}$ | 66.5 | 30.6 |

Example 3: Effect on IgIC Expression by EGFRvIII, Syn1, Syn2, and Syn18 Enhancer Sequences As shown in the following example, expression of the infectious disease antigen Ig1C from *Francisella tularensis* is also enhanced when fused to EGFRvIII, syn1, and syn18 expression enhancer sequences.

The PAP sequence used in Example 2 does not normally express well in the ActAN100* fusion system. This example was carried out as in Example 2; however, Ig1C replaced PAP as a test of the expression enhancement with an antigen that normally expresses well in the ActAN100* fusion system.

Ig1C Nucleic Acid Sequence (SEQ ID NO: 49):

```
atgagtgagatgataacaagacaacaggtaacaagtggcgagaccattca tgtgagaactgatcctactgcatgtataggatctcatcctaattgtagat tatttattgattctttaactatagctggggagaaacttgataaaaatatc gttgctatagatggtggagaggatgtcacgaaagctgattcggctacagc tgctgctagtgtaatacgtttatctataacgccaggctctataaatccaa caataagtattactcttggtgttctaattaaatcaaatgttagaactaaa attgaagagaaagtttcgagtatattacaagcaagtgctacagatatgaa aattaagttaggtaattctaataaaaaacaagagtataaaactgatgaag catggggtattatgatagatctatctaatttagagttatatccaataagt gctaaggcttttagtattagtatagagccaacagaacttatgggtgtttc aaaagatggaatgagatatcatattatatctatagatggtcttacaacat ctcaaggaagtttgccagtatgttgcgcagctagcacagataaaggagtt gctaaaataggatatattgcagctgca
```

Ig1C Protein Sequence (SEQ ID NO: 50):

MSEMITRQQVTSGETIHVRTDPTACIGSHPNCRLFIDSLTIAGEKLDKNI

VAIDGGEDVTKADSATAAASVIRLSITPGSINPTISITLGVLIKSNVRTK

IEEKVSSILQASATDMKIKLGNSNKKQEYKTDEAWGIMIDLSNLELYPIS

AKAFSISIEPTELMGVSKDGMRYHIISIDGLTTSQGSLPVCCAASTDKGV

AKIGYIAAA

Figure 3:
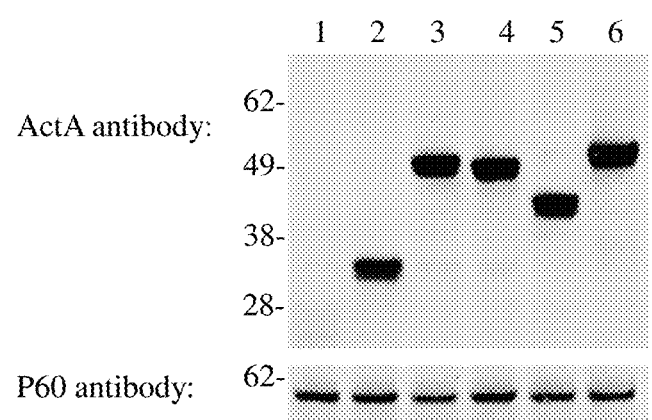
FIG. 3 depicts intracellular Western blot results for fusion protein expression by *Listeria monocytogenes* strains BH4203, BH4215, BH5128, BH5132, and BH5333.

ActAN100* was fused in-frame to five copies of four different repeats including EGFRvIII, syn1, syn2, syn18, and the infectious disease antigen Ig1C from *Francisella tularensis*. FIG. 3 depicts the intracellular Western blot of fusion protein expression. Again, the fusion protein composed of ActAN100*-syn18-Ig1C resulted in the highest protein expression (lane 6, strain BH5333). Relative expression based on the ActA/p60 ratio is set arbitrarily at 1 for the lowest expressing construct; n.a.: not applicable; n.d.: not detected. This is summarized in the following table:

| Lane | Strain | Antigen expression cassette | Predicted kDa | relative expression |
| --- | --- | --- | --- | --- |
| 1 | Lm11 | none | n.a. | n.a. |
| 2 | BH4203 | ActAN100*-iglC | 34.2 | 1.0 |
| 3 | BH4215 | ActAN100*-EGFRvIIIx5-iglC | 50.8 | 5.7 |
| 4 | BH5128 | ActAN100*-Syn1x5-iglC | 50.8 | 3.2 |
| 5 | BH5132 | ActAN100*-Syn2x5-iglC | 43.7 | 2.1 |
| 6 | BH5333 | ActAN100*-Syn18x5-iglC | 50.8 | 7.1 |

Example 4: Effect of Enhancer Sequence Copy Number on PAP Expression by Syn1

Figure 4:
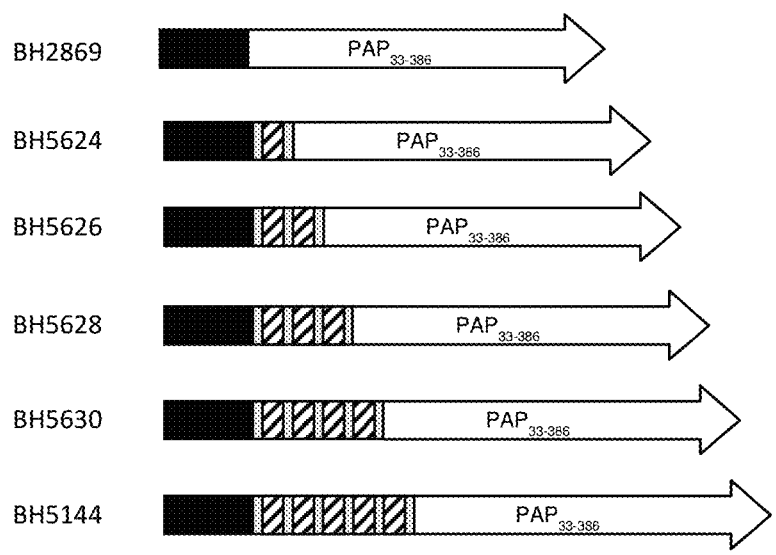
FIG. 4 depicts schematically the fusion protein constructs of *Listeria monocytogenes* strains BH2869, BH5624, BH5626, BH5628, BH5630, and BH5144.

Increasing the copy number of the syn1 repeat results in step-wise increases in the level when fused to PAP. This example was carried out as in Example 2; however, the number of copies of the syn1 enhancer sequence was varied from 0 to 5. FIG. 4 shows schematically the molecular constructs used in this example. ActAN100* (black) was fused in-frame to zero, one, two, three, four, or five copies of syn1 (diagonal cross hatch) and the tumor antigen $PAP_{33-386}$.

Figure 5:
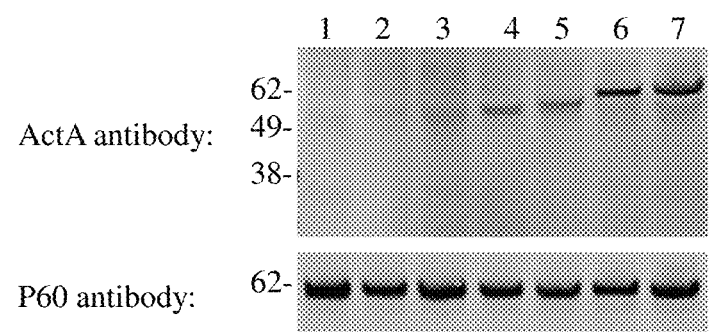
FIG. 5 depicts intracellular Western blot results for fusion protein expression by *Listeria monocytogenes* strains BH2869, BH5624, BH5626, BH5628, BH5630, and BH5144.

FIG. 5 depicts the intracellular Western blot of fusion protein expression. The PAP fusion protein was not detected without the addition of any copies of the syn1 repeat (lane 2). A 40-fold increase in expression was observed between the constructs with a single syn1 repeat (BH5624, lane 3) and the construct with 5 copies of the repeat unit (BH5144, lane 7). Relative expression based on the ActA/p60 ratio is set arbitrarily at 1 for the lowest expressing construct; n.a.: not applicable; n.d.: not detected. This is summarized in the following table:

| Lane | Strain | Antigen expression cassette | Predicted kDa | Relative expression |
|------|--------|-----------------------------|---------------|---------------------|
| 1 | Lm11 | none | n.a. | n.a. |
| 2 | BH2869 | ActAN100-hPAP$_{33-386}$ | 48.3 | n.d. |
| 3 | BH5624 | ActAN100*-Syn1x1-PAP$_{33-386}$ | 52.3 | 1 |
| 4 | BH5626 | ActAN100*-Syn1x2-PAP$_{33-386}$ | 56 | 2.1 |
| 5 | BH5628 | ActAN100*-Syn1x3-PAP$_{33-386}$ | 59.5 | 17.3 |
| 6 | BH5630 | ActAN100*-Syn1x4-PAP$_{33-386}$ | 63 | 26.7 |
| 7 | BH5144 | ActAN100*-Syn1x5-PAP$_{33-386}$ | 66.5 | 40.5 |

Example 5: Effect of Enhancer Sequence Copy Number on PAP Expression by Syn18

Figure 6:
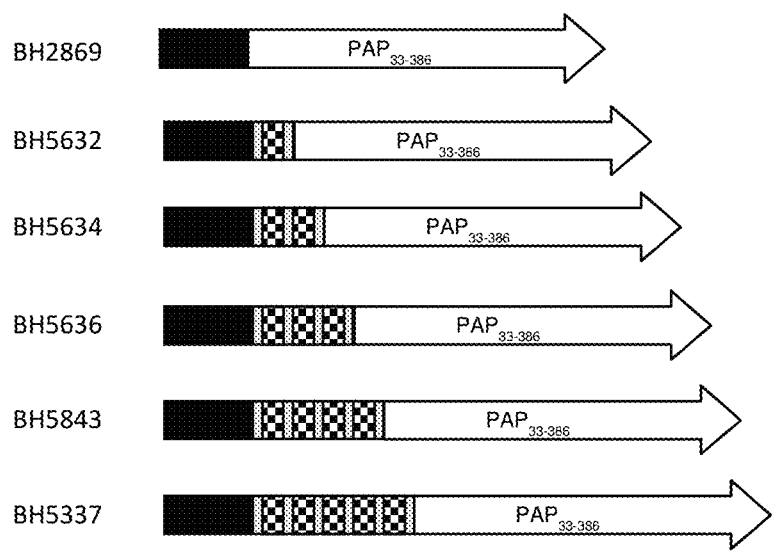
FIG. 6 depicts schematically the fusion protein constructs of *Listeria monocytogenes* strains BH2869, BH5632, BH5634, BH5636, BH5843, and BH5337.

Increasing the copy number of the syn18 repeat results in step-wise increases in the level when fused to PAP. This example was carried out as in Example 2; however, the number of copies of the syn18 enhancer sequence was varied from 0 to 5. FIG. 6 shows schematically the molecular constructs used in this example. ActAN100* (black) was fused in-frame to zero, one, two, three, four, or five copies of syn18 (checkerboard pattern) and the tumor antigen $PAP_{33-386}$.

Figure 7:
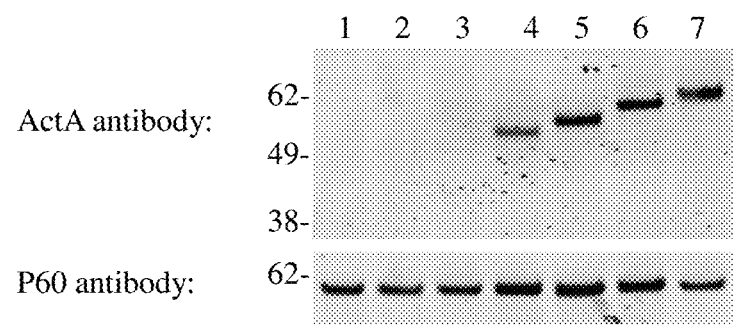
FIG. 7 depicts intracellular Western blot results for fusion protein expression by *Listeria monocytogenes* strains BH2869, BH5632, BH5634, BH5636, BH5843, and BH5337.

FIG. 7 depicts the intracellular Western blot of fusion protein expression. The PAP fusion protein was detected at a low level without the addition of the syn18 repeat (lane 2). An 82-fold increase in expression was observed between the constructs with no syn 18 repeats (BH2869, lane 2) and the construct with 5 copies of the repeat unit (BH5337, lane 7). A 51-fold increase in expression was observed between the construct with a single syn18 repeat (BH5632, lane 3) and five copies of the repeat unit (BH5337, lane 7). Relative expression based on the ActA/p60 ratio is set arbitrarily at 1 for the lowest expressing construct; n.a.: not applicable; n.d.: not detected. This is summarized in the following table:

| Lane | Strain | Antigen Expression Cassette | Predicted kDa | Relative expression |
|------|--------|-----------------------------|---------------|---------------------|
| 1 | Lm11 |  |  | n.a. |
| 2 | BH2869 | ActAN100-hPAP$_{33-386}$ | 48.3 | 1 |
| 3 | BH5632 | ActAN100*-Syn18x1-PAP$_{33-386}$ | 52.2 | 1.6 |
| 4 | BH5634 | ActAN100*-Syn18x2-PAP$_{33-386}$ | 56 | 23.8 |
| 5 | BH5636 | ActAN100*-Syn18x3-PAP$_{33-386}$ | 59.5 | 44.2 |
| 6 | BH5843 | ActAN100*-Syn18x4-PAP$_{33-386}$ | 63 | 84.5 |
| 7 | BH5337 | ActAN100*-Syn18x5-PAP$_{33-386}$ | 66.5 | 82.1 |

Example 6: Effect of Enhancer Sequence Copy Number on HBV Polymerase-HBxAg Dual Antigen Fusion Expression by Syn 1 and Syn18

Figure 8:
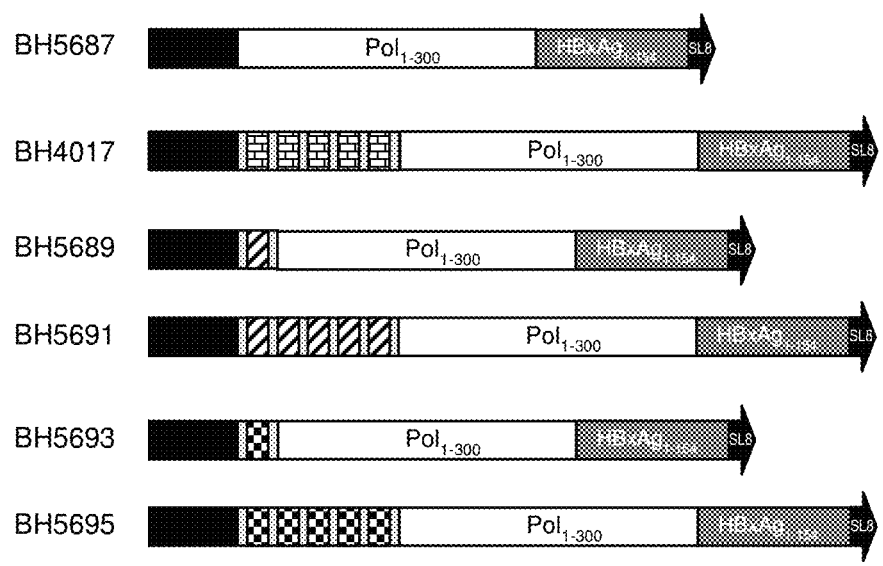
FIG. 8 depicts schematically the fusion protein constructs of *Listeria monocytogenes* strains BH5687, BH4017, BH5689, BH5691, BH5693, and BH5695.

Increasing the copy number of the syn1 repeat results in step-wise increases in the level when fused to PAP. This example was carried out as in Example 2. FIG. 8 shows schematically the molecular constructs used in this example. ActAN100* (black) was fused in-frame to five copies of EGFRvIII (brick pattern) and to zero, one, or five copies of syn1 (diagonal cross hatch pattern) or syn18 (checkerboard pattern) and the HBV Polymerase-HBxAg dual antigen, each from hepatitis B virus.

HBV $Pol_{1-300}$-HBxAg dual antigen with C-terminal SL8 peptide nucleic acid sequence (SEQ ID NO: 53):

ctgccacttagttatcaacattttcgcaaacttttgttgctcgacgatgg tactgaagctgggccactagaagaagagctaccacgtcttgcggatgcag acctcaatagacgtgtggccgaagatttgaacttaggcaatctaaacgta agtattccgtggacacataaagttggcaatttcactggtctgtattcaag tacggttccaatattcaatccagaatggcaaacccatcgtttcctaaaa tccatttacaagaagatattattaatcgctgccaacagttcgtcgggcca ttaacagtcaatgaaaagcgtcgcttgaaattgattatgcctgcgcgttt ctatccaactcatacaaaatacttgccgctagataaaggcattaaacctt actatccagatcaagtggtgaatcactattttcaaacccgccattatctt catacactctggaaagctggtatcttgtataaacgagagactacgcgatc cgccagttttgtggatcaccatatagctgggaacaagaacttcaacatg gtagacttgtgattaagacatcacaaagacatggagatgagagcttctgt tctcaaccgtcgggtatattgagtcgaagtagcgtcggtccatgtattcg tagccaacttaaacaatctcgtctaggccttcaaccacaccaagggccac ttgcatccagccaaccaggtagatcaggctcgatcagagcaagagcccac ccgtctacgcgacgatactttggtgtagaaccgtccggcagcggtcatat cgaccactccgttaacaatagcagttcttgtctacaccagtcagccgttc gtaaagcagcatactcacacctatctacttcaaaaagacaatcttcatcg actagtatggccgctcgtttatactgccaactagacccaagtcgggatgt gctatgtttgcgtccagttggtgccgagagccgtggtagaccattatccg gacctttaggaacgttaagttctccatcaccgtccgctgtaccagctgat catgggcacatttatcattacgcggtttaccagtttgcgcatttttcttc ggctggaccatgcgcacttcgctttacctcagcgcgatgtatggaaacga cagttaacgcgcatcaaatccttccgaaagttttgcacaaacgtacatta ggccttccagctatgagcactacagatttagaagcatatttcaaagattg -continued

```
tgtgtttaaagactgggaagaattgggtgaagaaattagacttaaagtct ttgtactagggggctgtagacataagttagtatgcgcacctgcgccttgt aatttctttacatctgcacaattgggtgacggtagtattaaacttagcaa agtattacaattagaaagtattattaattttgaaaaattagctgatggtt cagttaaa
```

HBV Pol$_{1-300}$-HBxAg dual antigen with C-terminal SL8 peptide protein sequence (SEQ ID NO: 54):

```
MPLSYQHFRKLLLLDDGTEAGPLEEELPRLADADLNRRVAEDLNLGNLNV

SIPWTHKVGNFTGLYSSTVPIFNPEWQTPSFPKIHLQEDIINRCQQFVGP

LTVNEKRRLKLIMPARFYPTHTKYLPLDKGIKPYYPDQVVNHYFQTRHYL

HTLWKAGILYKRETTRSASFCGSPYSWEQELQHGRLVIKTSQRHGDESFC

SQPSGILSRSSVGPCIRSQLKQSRLGLQPHQGPLASSQPGRSGSIRARAH

PSTRRYFGVEPSGSGHIDHSVNNSSSCLHQSAVRKAAYSHLSTSKRQSSS

TSMAARLYCQLDPSRDVLCLRPVGAESRGRPLSGPLGTLSSPSPSAVPAD

HGAHLSLRGLPVCAFSSAGPCALRFTSARCMETTVNAHQILPKVLHKRTL

GLPAMSTTDLEAYFKDCVFKDWEELGEEIRLKVFVLGGCRHKLVCAPAPC

NFFTSAQLGDGSIKLSKVLQLESIINFEKLADGSVK
```

Figure 9:
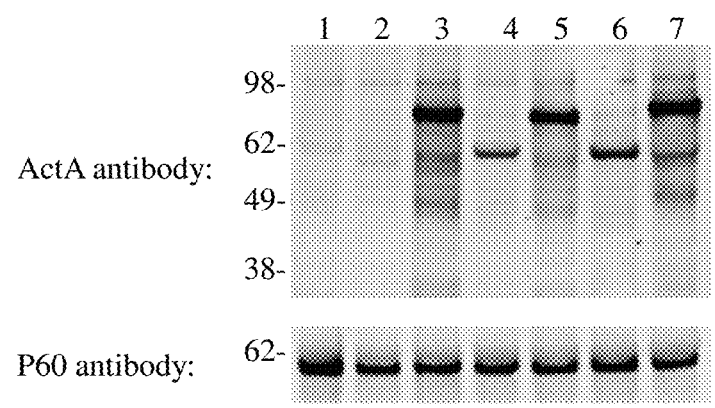
FIG. 9 depicts intracellular Western blot results for fusion protein expression by *Listeria monocytogenes* strains BH5687, BH4017, BH5689, BH5691, BH5693, and BH5695.
Figure 10:
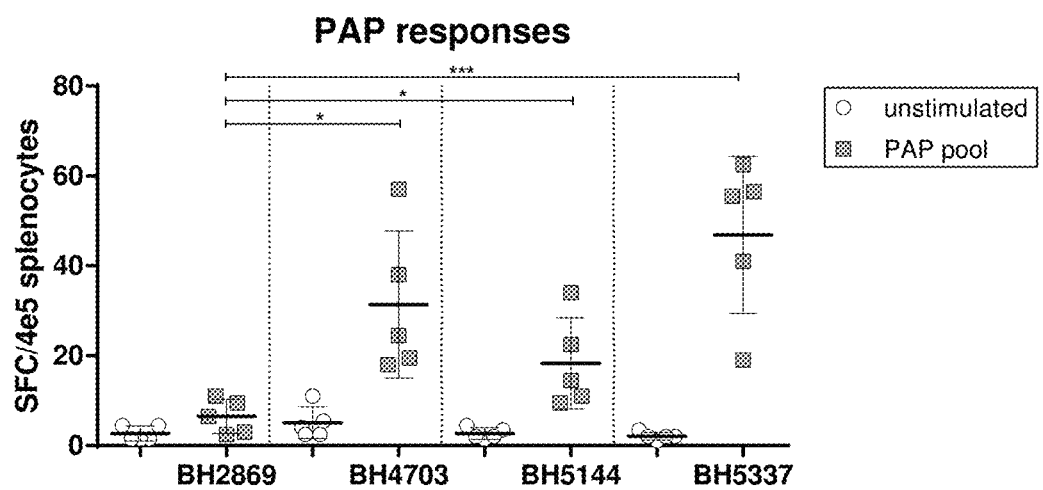
FIG. 10 depicts ELISPOT cytokine staining results for PAP-specific CD8+ T cells following immunization with BH2869 (ActAN100-PAP only), BH4703 (ActAN100*-EGFRvIII-PAP), BH5144 (ActAN100*-Syn1-PAP), and BH5337 (ActAN100*-Syn18-PAP).
Figure 11:
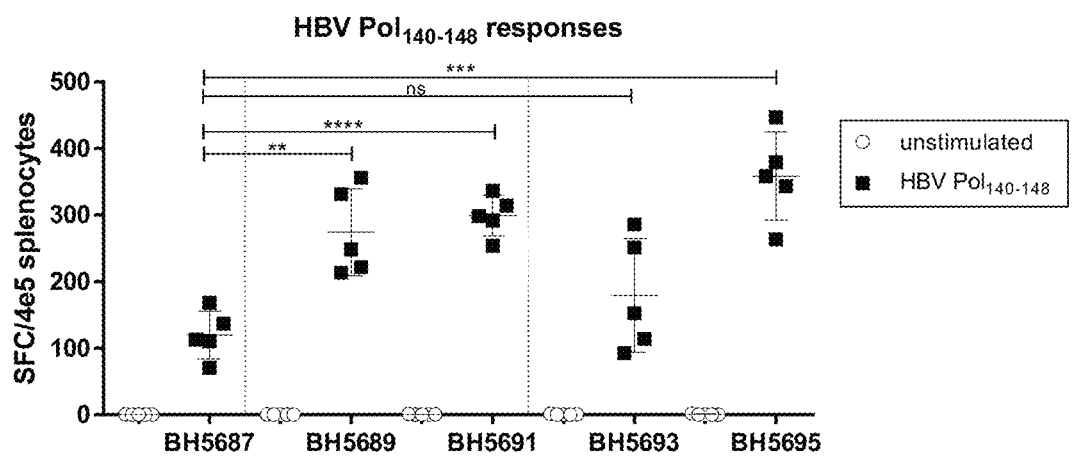
FIG. 11 depicts ELISPOT cytokine staining results for HBV-Pol specific CD8+ T cells following immunization with BH5687 (ActAN100*-HBV Pol$_{1-300}$-HBxAg), BH5689 (ActAN100*-syn1×1-HBV Pol$_{1-300}$-HBxAg), BH5691 (ActAN100*-syn1×5-HBV Pol$_{1-300}$-HBxAg), BH5693 (ActAN100*-syn18×1-HBV Pol$_{1-300}$-HBxAg), and BH5695 (ActAN100*-syn18×5-HBV Pol$_{1-300}$-HBxAg).
Figure 12:
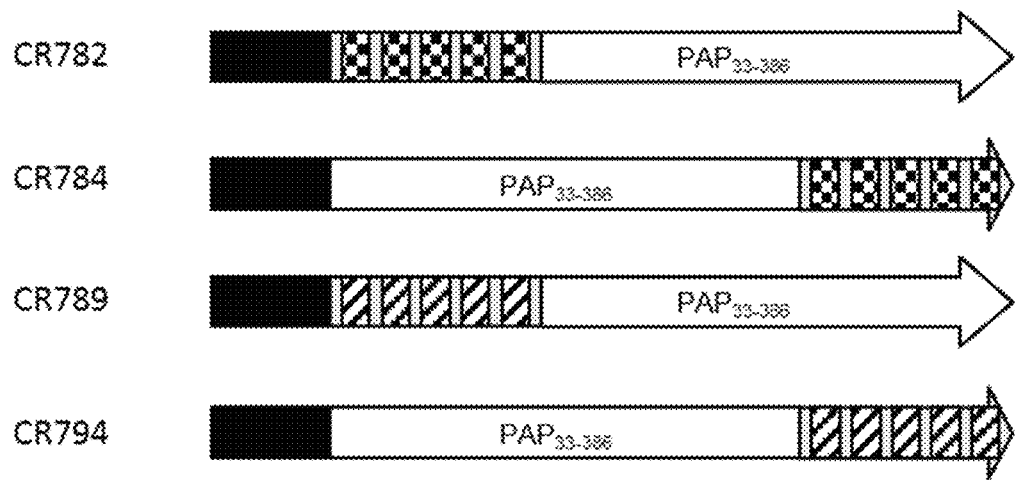
FIG. 12 depicts schematically the fusion protein constructs of *Listeria monocytogenes* strains CR782, CR784, CR789, and CR794.
Figure 13:
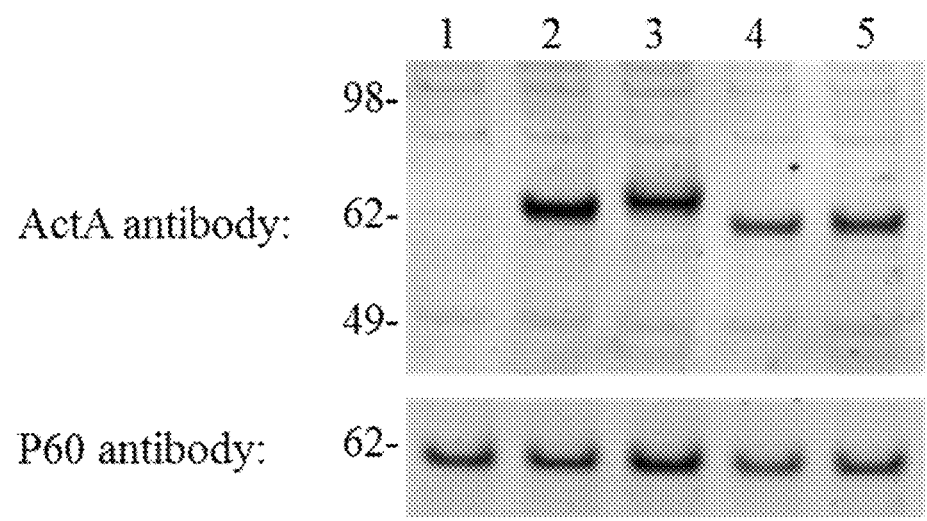
FIG. 13 depicts intracellular Western blot results for fusion protein expression by *Listeria monocytogenes* strains CR782, CR784, CR789, and CR794.
Figure 14:
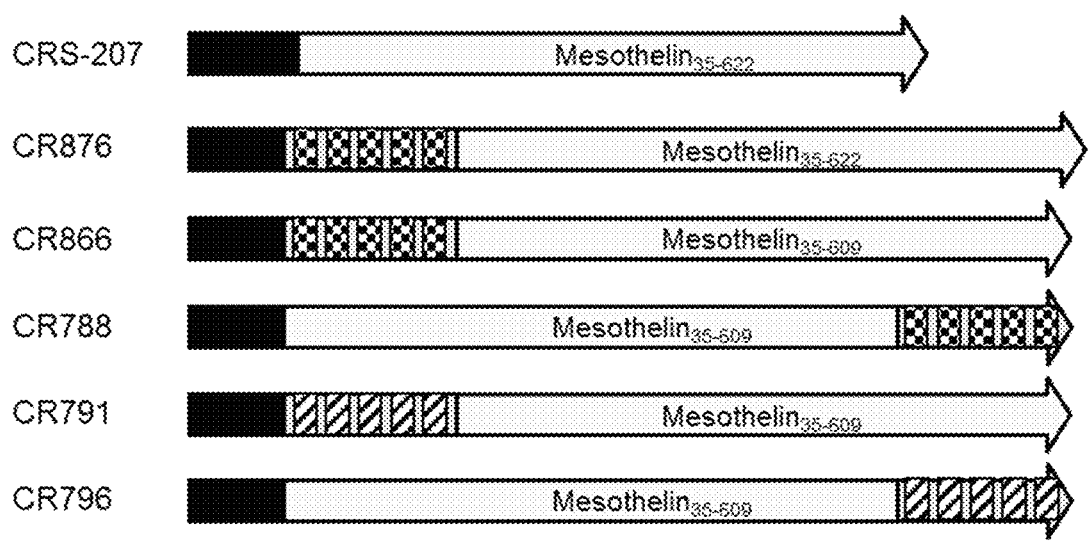
FIG. 14 depicts schematically the fusion protein constructs of *Listeria monocytogenes* strains CRS-207, CR876, CR866, CR788, CR791, and CR796.

FIG. 9 depicts the intracellular Western blot of fusion protein expression. The fusion protein composed of ActAN100*-Syn18x5-Pol-HBxAg resulted in a nearly 500-fold increase in expression compared to no synthetic expression enhancer (lane 7, strain BH5695). Relative expression based on the ActA/p60 ratio is set arbitrarily at 1 for the lowest expressing construct; n.a.: not applicable; n.d.: not detected. This is summarized in the following table:

| Lane | Strain | Antigen Expression Cassette | Predicted kDa | relative expression |
|---|---|---|---|---|
| 1 | Lm11 | none | n.a. | 0 |
| 2 | BH5687 | ActAN100*-HBV $Pol_{1-300}$-HBxAg-SL8 | 64.5 | 1 |
| 3 | BH4017 | ActAN100*-EGFRvIII-HBV $Pol_{1-300}$-HBxAg-SL8 | 81.1 | 359 |
| 4 | BH5689 | ActAN100*-Syn1x1-HBV $Pol_{1-300}$-HBxAg-SL8 | 68 | 24 |
| 5 | BH5691 | ActAN100*-Syn1x5-HBV $Pol_{1-300}$-HBxAg-SL8 | 81.1 | 198 |
| 6 | BH5693 | ActAN100*-Syn18x1-HBV $Pol_{1-300}$-HBxAg-SL8 | 68 | 44 |
| 7 | BH5695 | ActAN100*-Syn18x5-HBV $Pol_{1-300}$-HBxAg-SL8 | 81.1 | 483 |

Example 7: Effect of Enhancer Sequence Copy Number on PAP Immunogenicity

Female B10.Br mice (n=5 per group) were vaccinated intravenously with $5\times10^6$ cfu of BH2869 (ActAN100-PAP only), BH4703 (ActAN100*-EGFRvIII×5-PAP), BH5144 (ActAN100*-Syn1×5-PAP), and BH5337 (ActAN100*-Syn18×5-PAP) (per schematics in FIG. 1). PAP-specific T cell responses were determined by intracellular cytokine staining (ELISPOT) 7 days later, and are depicted in FIG. 10 as absolute number of IFN-γ positive PAP-specific CD8+ T cells per spleen. Results are expressed as mean spot-forming cells (SFC) per $4\times10^5$ cells. The highest PAP-specific immunogenicity was induced by the strain with the highest expression, with BH5337 inducing the highest PAP-specific immune response.

Example 8: Effect of Enhancer Sequence Copy Number on HBV-Pol Immunogenicity

Female mice (n=5 per group) were vaccinated intravenously with $1\times10^6$ cfu of BH5687 (ActAN100*-HBV $Pol_{1-300}$-HBxAg), BH5689 (ActAN100*-syn1×1-HBV $Pol_{1-300}$-HBxAg), BH5691 (ActAN100*-syn1×5-HBV $Pol_{1-300}$-HBxAg), BH5693 (ActAN100*-syn18×1-HBV $Pol_{1-300}$-HBxAg), and BH5695 (ActAN100*-syn18×5-HBV $Pol_{1-300}$-HBxAg) (per schematics in FIG. 8). HBV-Pol-specific T cell responses were determined by intracellular cytokine staining (ELISPOT) 7 days later, and are depicted in FIG. 11 as absolute number of IFN-γ positive PAP-specific CD8+ T cells per spleen. Results are expressed as mean spot-forming cells (SFC) per $4\times10^5$ cells. BH5689, BH5691 and BH5695 induced statistically higher immune responses (and BH5693 trended higher) when compared to BH5687.

Example 9: Effect of Enhancer Sequence Orientation on PAP Expression by Syn18 and Syn1

The syn18×5 or syn1×5 sequence enhances expression whether it is linked to the amino terminus or the carboxy terminus of the antigen. This example was carried out as in Example 2; however, the syn18×5 or syn1×5 enhancer sequence was linked to either the amino terminus or the carboxy terminus of the $PAP_{33-386}$ antigen sequence. FIG. 12 shows schematically the molecular constructs used in this example. ActAN100* (black) was fused in-frame to five copies of syn18 (checkerboard pattern) or syn1 (diagonal cross hatch pattern) linked to the amino terminus or the carboxy terminus of the tumor antigen $PAP_{33-386}$.

FIG. 13 depicts the intracellular Western blot of fusion protein expression. The PAP fusion protein was detected at comparable levels for both the syn18×5 and the syn1×5, whether these were linked to the amino terminus of the PAP antigen (lanes 2 and 4, CR782 and CR789) or to the carboxy terminus of the PAP antigen (lanes 3 and 5, CR784 and CR794). Relative expression based on the ActA/p60 ratio is set arbitrarily at 1 for the lowest expressing construct; n.a.: not applicable; n.d.: not detected. This is summarized in the following table:

| Lane | Strain | Antigen Expression Cassette | Predicted kDa | Relative expression |
|---|---|---|---|---|
| 1 | Lm11 | | | n.a. |
| 2 | CR782 | ActAN100*-Syn18x5-$PAP_{33-386}$ | 65.5 | 2.3 |
| 3 | CR784 | ActAN100*-$PAP_{33-386}$-Syn18x5 | 65.5 | 1.6 |
| 4 | CR789 | ActAN100*-Syn1x5-$PAP_{33-386}$ | 64.6 | 1 |
| 5 | CR794 | ActAN100*-$PAP_{33-386}$-Syn1x5 | 64.6 | 1.4 |

Example 10: Effect of Enhancer Sequence on Mesothelin Antigen Fusion Expression by Syn1×5 and Syn18×5

Mesothelin antigen is increased with syn18×5 linked to the amino terminus or carboxy terminus of $mesothelin_{35-609}$, and with syn1×5 linked to the amino terminus of $mesothelin_{35-609}$. This example was carried out as in Example 2. FIG. 14 shows schematically the molecular constructs used in this example. ActAN100* (black) was fused in-frame to mesothelin$_{35-622}$ antigen, five copies of syn18 (checkerboard pattern) linked to the amino terminus of mesothelin$_{35-622}$ antigen, or five copies of syn1 (diagonal cross hatch pattern) or syn18 linked to the amino terminus or the carboxy terminus of the tumor antigen mesothelin$_{35-609}$.

Mesothelin$_{35-622}$ Nucleic Acid Sequence (SEQ ID NO: 55):

```
cgtacattagcaggtgaaacaggtcaagaagcagcaccacttgacggtgt
attaacgaatccaccaaatatatcaagtttaagtccacgtcaattattag
gttttccatgtgcagaagtttcaggtttaagtacagaacgtgtccgtgag
ttagcagttgcattagcacaaaaaaacgttaaattatctacagaacagtt
acgttgtttagcccatagattaagcgaaccaccagaagacttagatgcac
ttcctttagaccttcttttattcttaaatccagatgcattttcaggacca
caagcatgtacacgttttttagtcgaattacaaaagccaatgttgattt
attacctcgtggggctcctgaaagacaacgtttattacctgctgcattag
catgctgggtgttcgcggtagcttattaagtgaagccgatgttcgtgct
ttagggggtttagcatgtgatttacctggtcgtttcgttgcagaatcagc
agaagtgttattaccgagattagtttcatgcccaggacctttagatcaag
atcaacaagaggcagctagagcagctcttcaaggaggagcccaccatat
ggcccaccaagtacatggagtgtttctacaatggatgcgttaagaggttt
attaccggttttaggacaaccaattattcgtagtattccacaaggcattg
tagcagcatggcgtcaacgtagttctcgtgatccgtcttggcgacaacca
gaacgtacaattctacgtccaagatttcgtagagaagtagaaaaaacggc
gtgtcctagtggcaaaaaagcacgtgaaattgatgaaagtttaattttt
ataaaaaatgggaattagaagcatgtgtcgatgcagcattactagctaca
caaatggatcgtgttaatgctattccattcacatatgaacaattagatgt
tttaaagcataaattagacgaattatatccacaaggttatccagaatcag
ttattcaacatttaggttacttatttttaaaaatgagtccagaagacata
cgcaaatggaatgttacaagtttagaaacattaaaagcgcttttagaagt
taacaaaggtcatgaaatgagtccacaagttgctacgttaattgatagat
tcgttaaaggccgtggtcaattagataaagatactttagatacattaaca
gcatttatcctggctacttatgcagtttatcaccagaagaattaagttc
cgttccaccgagtagtatctgggcagttcgtccgcaagatttagatacat
gcgacccacgtcaattagatgttttatatccaaaagcaagattagctttc
caaaatatgaacggtagtgaatatttcgtaaaaattcaatccttttttagg
tggtgcaccaactgaagatctaaaagcattaagccaacaaatgtaagta
tggatttagctacgtttatgaaattacgtacagatgcagttctaccatta
acagttgcagaagttcaaaaattattaggtccacacgtagaaggattaaa
agcagaagaacgtcaccgtccagttcgcgattggattttacgtcaacgtc
aagatgatttagatacattaggtttaggtttacaaggcggtattccgaat
ggatatttagtgttagatttatcggttcaagaagcattaagtggtacacc
```

Mesothelin$_{35-622}$ Protein Sequence (SEQ ID NO: 56):

RTLAGETGQEAAPLDGVLTNPPNISSLSPRQLLGFPCAEVSGLSTERVRE
LAVALAQKNVKLSTEQLRCLAHRLSEPPEDLDALPLDLLLFLNPDAFSGP
QACTRFFSRITKANVDLLPRGAPERQRLLPAALACWGVRGSLLSEADVRA
LGGLACDLPGRFVAESAEVLLPRLVSCPGPLDQDQQEAARAALQGGGPPY
GPPSTWSVSTMDALRGLLPVLGQPIIRSIPQGIVAAWRQRSSRDPSWRQP
ERTILRPRFRREVEKTACPSGKKAREIDESLIFYKKWELEACVDAALLAT
QMDRVNAIPFTYEQLDVLKHKLDELYPQGYPESVIQHLGYLFLKMSPEDI
RKWNVTSLETLKALLEVNKGHEMSPQVATLIDRFVKGRGQLDKDTLDTLT
AFYPGYLCSLSPEELSSVPPSSIWAVRPQDLDTCDPRQLDVLYPKARLAF
QNMNGSEYFVKIQSFLGGAPTEDLKALSQQNVSMDLATFMKLRTDAVLPL
TVAEVQKLLGPHVEGLKAEERHRPVRDWILRQRQDDLDTLGLGLQGGIPN
GYLVLDLSVQEALSGTPCLLGPGPVLTVLALLLASTLA

Mesothelin$_{35-609}$ Nucleic Acid Sequence (SEQ ID NO: 57):

```
cgtacattagcaggtgaaacaggtcaagaagcagcaccacttgacggtgt
attaacgaatccaccaaatatatcaagtttaagtccacgtcaattattag
gttttccatgtgcagaagtttcaggtttaagtacagaacgtgtccgtgag
ttagcagttgcattagcacaaaaaaacgttaaattatctacagaacagtt
acgttgtttagcccatagattaagcgaaccaccagaagacttagatgcac
ttcctttagaccttcttttattcttaaatccagatgcattttcaggacca
caagcatgtacacgttttttagtcgaattacaaaagccaatgttgattt
attacctcgtggggctcctgaaagacaacgtttattacctgctgcattag
catgctgggtgttcgcggtagcttattaagtgaagccgatgttcgtgct
ttagggggtttagcatgtgatttacctggtcgtttcgttgcagaatcagc
agaagtgttattaccgagattagtttcatgcccaggacctttagatcaag
atcaacaagaggcagctagagcagctcttcaaggaggagcccaccatat
ggcccaccaagtacatggagtgtttctacaatggatgcgttaagaggttt
attaccggttttaggacaaccaattattcgtagtattccacaaggcattg
tagcagcatggcgtcaacgtagttctcgtgatccgtcttggcgacaacca
gaacgtacaattctacgtccaagatttcgtagagaagtagaaaaaacggc
gtgtcctagtggcaaaaaagcacgtgaaattgatgaaagtttaattttt
ataaaaaatgggaattagaagcatgtgtcgatgcagcattactagctaca
caaatggatcgtgttaatgctattccattcacatatgaacaattagatgt
tttaaagcataaattagacgaattatatccacaaggttatccagaatcag
ttattcaacatttaggttacttatttttaaaaatgagtccagaagacata
cgcaaatggaatgttacaagtttagaaacattaaaagcgcttttagaagt
taacaaaggtcatgaaatgagtccacaagttgctacgttaattgatagat
gtgtttattaggtccaggtccagttttaacagtgttagcattattattag
ccagtacattagct
```

```
tcgttaaaggccgtggtcaattagataaagatactttagatacattaaca gcattttatcctggctacttatgcagtttatcaccagaagaattaagttc cgttccaccgagtagtatctgggcagttcgtccgcaagatttagatacat gcgacccacgtcaattagatgttttatatccaaaagcaagattagcttc caaaatatgaacggtagtgaatatttcgtaaaaattcaatccttttagg tggtgcaccaactgaagatctaaaagcattaagccaacaaaatgtaagta tggatttagctacgtttatgaaattacgtacagatgcagttctaccatta acagttgcagaagttcaaaaattattaggtccacacgtagaaggattaaa agcagaagaacgtcaccgtccagttcgcgattggattttacgtcaacgtc aagatgatttagatacattaggtttaggtttacaaggcggtattccgaat ggatatttagtgttagatttatcggttcaagaagcattaagtggtacacc gtgtttattaggtccaggtccagtt
```

Mesothelin$_{35-609}$ Protein Sequence (SEQ ID NO: 58):

```
RTLAGETGQEAAPLDGVLTNPPNISSLSPRQLLGFPCAEVSGLSTERVRE

LAVALAQKNVKLSTEQLRCLAHRLSEPPEDLDALPLDLLLFLNPDAFSGP

QACTRFFSRITKANVDLLPRGAPERQRLLPAALACWGVRGSLLSEADVRA

LGGLACDLPGRFVAESAEVLLPRLVSCPGPLDQDQQEAARAALQGGGPPY

GPPSTWSVSTMDALRGLLPVLGQPIIRSIPQGIVAAWRQRSSRDPSWRQP

ERTILRPRFRREVEKTACPSGKKAREIDESLIFYKKWELEACVDAALLAT

QMDRVNAIPFTYEQLDVLKHKLDELYPQGYPESVIQHLGYLFLKMSPEDI

RKWNVTSLETLKALLEVNKGHEMSPQVATLIDRFVKGRGQLDKDTLDTLT

AFYPGYLCSLSPEELSSVPPSSIWAVRPQDLDTCDPRQLDVLYPKARLAF

QNMNGSEYFVKIQSFLGGAPTEDLKALSQQNVSMDLATFMKLRTDAVLPL

TVAEVQKLLGPHVEGLKAEERHRPVRDWILRQRQDDLDTLGLGLQGGIPN

GYLVLDLSVQEALSGTPCLLGPGPV
```

Figure 15:
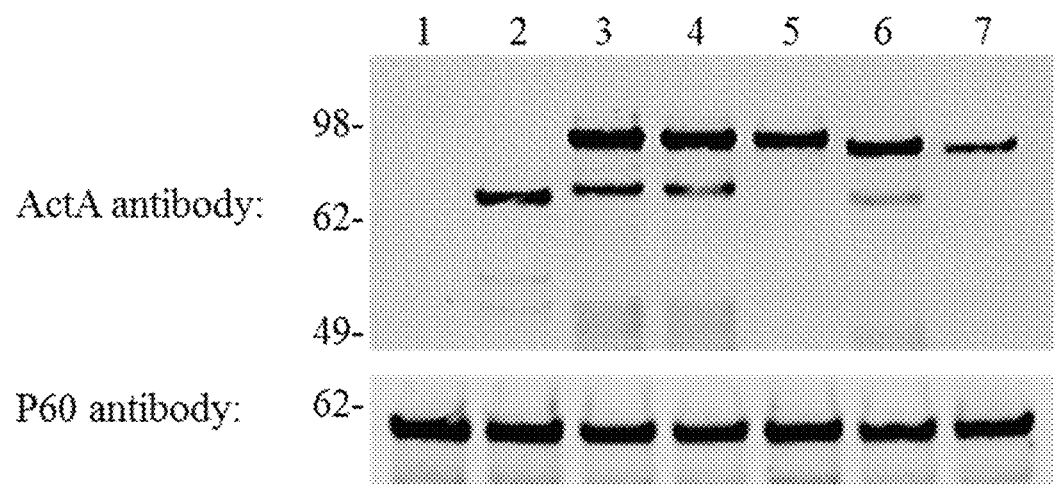
FIG. 15 depicts the broth culture Western blot results for fusion protein expression by *Listeria monocytogenes* strains CRS-207, CR876, CR866, CR788, CR791, and CR796.

FIG. 15 depicts the broth culture Western blot of fusion protein expression. The fusion protein composed of ActAN100*-Syn18x5-mesothelin$_{35-622}$ expressed higher levels of fusion protein than the CRS-207 control construct. The fusion protein composed of ActAN100*-Syn18x5-mesothelin$_{35-622}$, ActAN100*-mesothelin$_{35-622}$-Syn18x5 or ActAN100*-Syn1x5-mesothelin$_{35-609}$ also expressed higher levels than the CRS-207 control. Relative expression based on the ActA/p60 ratio is set arbitrarily at 1 for the lowest expressing construct; n.a.: not applicable; n.d.: not detected. This is summarized in the following table:

| Lane | Strain | Antigen Expression Cassette | Predicted kDa | relative expression |
|---|---|---|---|---|
| 1 | Lm11 | none | n.a. | 0 |
| 2 | CRS-207 | ActAN100-mesothelin$_{35-622}$ | 72.7 | 1.7 |
| 3 | CR876 | ActAN100*-Syn18x5-mesothelin$_{35-622}$ | 89 | 21.5 |
| 4 | CR866 | ActAN100*-Syn18x5-mesothelin$_{35-609}$ | 87.7 | 17.7 |
| 5 | CR788 | ActAN100*-mesothelin$_{35-609}$-Syn18x5 | 87.7 | 7.3 |
| 6 | CR791 | ActAN100*-Syn1x5-mesothelin$_{35-609}$ | 86.8 | 7.7 |
| 7 | CR796 | ActAN100*-mesothelin$_{35-609}$-Syn1x5 | 86.8 | 1 |

Example 11: Effect of Enhancer Sequence on Expression of FopC Antigen in E. Coli Plasmids encoding recombinant proteins with or without tags were transformed into T7 Express competent E. coli (NEB). Proteins included FopC tagged with 6xHis at the carboxy terminus, without an amino terminal fusion partner, or with a SUMO tag or syn18x5 tag at the amino terminus. Resulting colonies were used to inoculate LB broth (1 ml) with antibiotic, and cultures were incubated with shaking at 37° C. until they reached an OD$_{600}$ of ~0.5. Uninduced samples were collected by centrifuging an aliquot (100 µl) of the culture. Isopropyl β-D-1-thiogalactopyranoside (IPTG) was added (0.5 mM), and the cultures were incubated with shaking at 37° C. for an additional two hours. Induced samples were collected by centrifuging an aliquot (50 µl) of the culture. Both uninduced and induced samples were resuspended in lysis buffer (100 µl 1xLDS buffer with reducing agent; Novex), incubated at 95° C. for 10 min, vortexed and stored at −20° C.

Aliquots (5 µl) were run on 4-12% Bis-Tris PAGE gels in 1xMES buffer (Invitrogen) and transferred to a 0.45 µm nitrocellulose membrane for detection. Following transfer, membrane was rinsed briefly in water, incubated with REVERT Total Protein Stain for 5 min (5 ml; Li-Cor), rinsed briefly two times with Wash Solution then scanned using a Li-Cor Odyssey system. Following imaging, the membrane was rinsed briefly with water then blocked for 1 hour at room temperature in Odyssey blocking buffer (Li-Cor). 6xHis-tagged recombinant proteins were detected using a polyclonal anti-polyHis antibody (1:4,000 dilution; Sigma #H1029). Goat anti-mouse (IRDye 680RD; Odyssey) secondary antibody was used at a 1:10,000 dilution. All antibodies were diluted in Odyssey blocking buffer with 0.2% Tween. Membranes were incubated with primary antibody overnight at 4° C., washed three times for five minutes each wash with PBS containing 0.1% Tween, then incubated with secondary antibody(s) for 1 hour at room temperature. Membranes were washed a further four times, the last wash with PBS only, then scanned using a Li-Cor Odyssey system.

Western blots were quantitated with Li-Cor Image Studio software. Individual His-containing bands were boxed on images representing the 800 nm signal, and the total intensity within each box was determined. Untagged fopC-6xHis nucleic acid sequence (SEQ ID NO: 59):

```
atggaagatagtccacaagttgtatctcaaggcggaccacttggagcaac ttcgattggagatcaaaatctcggacaacctgatccaaacgcaagtggtg ccagtagcacaacacaaacaacgggatcgaatttgaatgatcgggaattg ctactaaaacttcaacaacaagtgcaacaattacagggacaattacaaca actcaaagcgcaaggtaacggcggtggtttgcaaaatacgtataatggat catctcaatttactacatattctagtaaagtagatggaaacaaaaatcct
```

-continued cgaacattaggtggaaatggggaatcgaaagacctttcgcaagcactaat
tggcggccaaacaagttctgatatcatgggcaacgtgaatgcatctaact
cgattatcaatttagctagtgaaccattaggggg tgttttcaatcaaaaa
ggtggaattgatgttggtggtgctccagccattacgacacaaggccaagt
tacatacttaggatcatattccggaaataacagtattccgatcggccaga
ttagcagcaatcttt ttgcgtctactt tattgggacaacgtgagaaattt
gatgactatagtgtattcttcggtgggtttatcgaagcagatgcgcaagc
atgggtttgggagtgctgtaactaaagtccaaaacgcaggtcaactttcat
caaatggacagaatatctacttaacatccgcaaacttatactttctatca
aatcttggccattatgtaactgctcaatttgattttgatacgaatgaatc
tggttcattcagcaacctagatatttctccattctttgttacggcaggtc
gtaataagttatcagttggctcctatgggggtggtggcacatggactagc
gggattaccaaatttctatcaccaaatcaggtaactaacgtcagtataga
ctataaggatcaagtctggaacgcgaatattgcagttttt ggaagtgatg
atcgtcgcgctaacttttccaccggtttattctatgcggactcatggact
ccgaatctggcagctggattcaatgttggctatgattcaacattgctgga
gcgggtaattcaagcatagctaattcacttgctaatctaaatagaagctc
tgacaacgtaggtgcgcttaatgttgacggaaatcttacttatgccatat
gggatggttttctaaatctgggagctgggtgggcttccaccactacaaaa
gaggatttcaataacaacggtggtagtgtattagcaggcgcgtggtatgg
agcattgaactatagcgcaatcttaggtggtagaaatacaaatttcgggg
tgacatatggtcaatcatataacgcagctgctattcccatggaaacggcg
aatgcgagtcctacatttggtcagacagcaagcggcattaaacaacaact
tatctttagtgcgcaaagagcttactttgatgacaatgttctctttgggc
cggaatacgcttaccagcgcttatacacgggtgaacacatgaatacgatt
actcttgatatgtctgtgtatgttactagtcatcatcatcatcatcacta
a Untagged fopC-6×his Protein Sequence (SEQ ID NO: 60):

MEDSPQVVSQGGPLGATSIGDQNLGQPDPNASGASSTTQTTGSNLNDREL
LLKLQQQVQQLQGQLQQLKAQGNGGGLQNTYNGSSQFTTYSSKVDGNKNP
RTLGGNGESKDLSQALIGGQTSSDIMGNVNASNSIINLASEPLGGVFNQK
GGIDVGGAPAITTQGQVTYLGSYSGNNSIPIGQISSNLFASTLLGQREKF
DDYSVFFGGFIEADAQAWFGSAVTKVQNAGQLSSNGQNIYLTSANLYFLS
NLGHYVTAQFDFDTNESGSFSNLDISPFFVTAGRNKLSVGSYGGGGTWTS
GITKFLSPNQVTNVSIDYKDQVWNANIAVFGSDDRRANFSTGLFYADSWT
PNLAAGFNVGYVFNIAGAGNSSIANSLANLNRSSDNVGALNVDGNLTYAI
WDGFLNLGAGWASTTTKEDFNNNGGSVLAGAWYGALNYSAILGGRNTNFG
VTYGQSYNAAAIPMETANASPTFGQTASGIKQQLIFSAQRAYFDDNVLFG
PEYAYQRLYTGEHMNTITLDMSVYVTSHHHHHH

SUMO fopC-6×his Nucleic Acid Sequence (SEQ ID NO: 61):

atgggcagcagccatcatcatcatcatcacggcagcggcctggtgccgcg
cggcagcgctagcatgtcggactcagaagtcaatcaagaagctaagccag
aggtcaagccagaagtcaagcctgagactcacatcaatttaaaggtgtcc
gatggatcttcagagatcttcttcaagatcaaaaagaccactcctttaag
aaggctgatggaagcgttcgctaaaagacagggtaaggaaatggactcct
taagattcttgtacgacggtattgaattcaagctgatcagacccctgaa
gatttggacatggaggataacgatattattgaggctcacagagaacagac
cggtggatccgaagatagtccacaagttgtatctcaaggcggaccacttg
gagcaacttcgattggagatcaaaatctcggacaacctgatccaaacgca
agtggtgccagtagcacaacacaaacaacgggatcgaatttgaatgatcg
ggaattgctactaaaacttcaacaacaagtgcaacaattacagggacaat
tacaacaactcaaagcgcaaggtaacggcggtggtttgcaaaatacgtat
aatggatcatctcaatttactacatattctagtaaagtagatggaaacaa
aaatcctcgaacattaggtggaaatggggaatcgaaagacctttcgcaag
cactaattggcggccaaacaagttctgatatcatgggcaacgtgaatgca
tctaactcgattatcaatttagctagtgaaccattaggggg tgttttcaa
tcaaaaaggtggaattgatgttggtggtgctccagccattacgacacaag
gccaagttacatacttaggatcatattccggaaataacagtattccgatc
ggccagattagcagcaatcttt ttgcgtctactt tattgggacaacgtga
gaaatttgatgactatagtgtattcttcggtgggtttatcgaagcagatg
cgcaagcatgggtttgggagtgctgtaactaaagtccaaaacgcaggtcaa
cttt catcaaatggacagaatatctacttaacatccgcaaacttatactt
tctatcaaatcttggccattatgtaactgctcaatttgattttgatacga
atgaatctggttcattcagcaacctagatatttctccattctttgttacg
gcaggtcgtaataagttatcagttggctcctatgggggtggtggcacatg
gactagcgggattaccaaatttctatcaccaaatcaggtaactaacgtca
gtatagactataaggatcaagtctggaacgcgaatattgcagttttt gga
agtgatgatcgtcgcgctaacttttccaccggtttattctatgcggactc
atggactccgaatctggcagctggattcaatgttggctatgttttcaaca
ttgctggagcgggtaattcaagcatagctaattcacttgctaatctaaat
agaagctctgacaacgtaggtgcgcttaatgttgacggaaatcttactta
tgccatatgggatggttttctaaatctgggagctgggtgggcttccacca
ctacaaaagaggatttcaataacaacggtggtagtgtattagcaggcgcg
tggtatggagcattgaactatagcgcaatcttaggtggtagaaatacaaa
tttcggggtgacatatggtcaatcatataacgcagctgctattcccatgg
aaacggcgaatgcgagtcctacatttggtcagacagcaagcggcattaaa
caacaacttatctttagtgcgcaaagagcttactttgatgacaatgttct
ctttgggccggaatacgcttaccagcgcttatacacgggtgaacacatga SUMO fopC-6×his Protein Sequence (SEQ ID NO: 62):

MGSSHHHHHHGSGLVPRGSASMSDSEVNQEAKPEVKPEVKPETHINLKVS
DGSSEIFFKIKKTTPLRRLMEAFAKRQGKEMDSLRFLYDGIRIQADQTPE
DLDMEDNDIIEAHREQTGGSEDSPQVVSQGGPLGATSIGDQNLGQPDPNA
SGASSTTQTTGSNLNDRELLLKLQQQVQQLQGQLQQLKAQGNGGGLQNTY
NGSSQFTTYSSKVDGNKNPRTLGGNGESKDLSQALIGGQTSSDIMGNVNA
SNSIINLASEPLGGVFNQKGGIDVGGAPAITTQGQVTYLGSYSGNNSIPI
GQISSNLFASTLLGQREKFDDYSVFFGGFIEADAQAWFGSAVTKVQNAGQ
LSSNGQNIYLTSANLYFLSNLGHYVTAQFDFDTNESGSFSNLDISPFFVT
AGRNKLSVGSYGGGGTWTSGITKFLSPNQVTNVSIDYKDQVWNANIAVFG
SDDRRANFSTGLFYADSWTPNLAAGFNVGYVFNIAGAGNSSIANSLANLN
RSSDNVGALNVDGNLTYAIWDGFLNLGAGWASTTTKEDFNNNGGSVLAGA
WYGALNYSAILGGRNTNFGVTYGQSYNAAAIPMETANASPTFGQTASGIK
QQLIFSAQRAYFDDNVLFGPEYAYQRLYTGEHMNTITLDMSVYVTSHHHH
HH

Syn18×5 fopC-6×his Nucleic Acid Sequence (SEQ ID NO: 63):

atgggcagcagccatcatcatcatcatcacggcagcggcctggtgccgcg
cggcagcgctagcgcaagcaaagtattggaatctaatcaaagcgtagagg
acaagcacaatgagttcatgttgacggagtacggttcatgtgccgatggc
tcagtaaagactagcgcgagcaaagtggccgagtcaaatcagtctgttga
ggacaaacataatgagttcatgttaacggagtatggtagctgtggagatg
gttcaattaaattatcaaaagtcttagaatctaatcagagcgttgaggac
aagcataatgagttcatgttgacggagtacggttcatgtgctgacggaag
tgttaaagcgtcgaaagtagctgaatcaaatcaatctgtagaggacaaac
acaatgaatttatgctaacagaatacggcagctgcggtgatggctcgatc
aaattgtcaaaagttttagaatctaaccagagcgttgaagataagcacaa
cgaatttatgttaacggagtacggttcatgcgcggatggttccgttaaag
gatccgaagatagtccacaagttgtatctcaaggcggaccacttggagca
acttcgattggagatcaaaatctcggacaacctgatccaaacgcaagtgg
tgccagtagcacaacacaaacaacgggatcgaatttgaatgatcgggaat
tgctactaaaacttcaacaacaagtgcaacaattacagggacaattacaa
caactcaaagcgcaaggtaacggcggtggtttgcaaaatacgtataatgg
atcatctcaatttactacatattctagtaaagtagatggaaacaaaaatc
ctcgaacattaggtggaaatgggaatcgaaagacctttcgcaagcacta
attggcggccaaacaagttctgatatcatgggcaacgtgaatgcatctaa
ctcgattatcaatttagctagtgaaccattagggggtgttttcaatcaaa
aaggtggaattgatgttggtggtgctccagccattacgacacaaggccaa gttacatacttaggatcatattccggaaataacagtattccgatcggcca
gattagcagcaatcttttttgcgtctactttattgggacaacgtgagaaat
ttgatgactatagtgtattcttcggtgggtttatcgaagcagatgcgcaa
gcatggtttgggagtgctgtaactaaagtccaaaacgcaggtcaactttc
atcaaatggacagaatatctacttaacatccgcaaacttatactttctat
caaatcttggccattatgtaactgctcaatttgattttgatacgaatgaa
tctggttcattcagcaacctagatatttctccattcttttgttacggcagg
tcgtaataagttatcagttggctcctatgggggtggtggcacatggacta
gcgggattaccaaatttctatcaccaaatcaggtaactaacgtcagtata
gactataaggatcaagtctggaacgcgaatattgcagtttttggaagtga
tgatcgtcgcgctaacttttccaccggttttattctatgcggactcatgga
ctccgaatctggcagctggattcaatgttggctatgttttcaacattgct
ggagcgggtaattcaagcatagctaattcacttgctaatctaaatagaag
ctctgacaacgtaggtgcgcttaatgttgacggaaatcttacttatgcca
tatgggatggttttctaaatctgggagctgggtgggcttccaccactaca
aaagaggatttcaataacaacggtggtagtgtattagcaggcgcgtggta
tggagcattgaactatagcgcaatcttaggtggtagaaatacaaatttcg
gggtgacatatggtcaatcatataacgcagctgctattcccatggaaacg
gcgaatgcgagtcctacatttggtcagacagcaagcggcattaaacaaca
acttatctttagtgcgcaaagagcttactttgatgacaatgttctctttg
ggccggaatacgcttaccagcgcttatacacgggtgaacacatgaatacg
attactcttgatatgtctgtgtatgttactagtcatcatcatcatcatca
ctaa Syn18×5 fopC-6×his Protein Sequence (SEQ ID NO: 64):

MGSSHHHHHHGSGLVPRGSASASKVLESNQSVEDKHNEFMLTEYGSCADG
SVKTSASKVAESNQSVEDKHNEFMLTEYGSCGDGSIKLSKVLESNQSVED
KHNEFMLTEYGSCADGSVKASKVAESNQSVEDKHNEFMLTEYGSCGDGSI
KLSKVLESNQSVEDKHNEFMLTEYGSCADGSVKGSEDSPQVVSQGGPLGA
TSIGDQNLGQPDPNASGASSTTQTTGSNLNDRELLLKLQQQVQQLQGQLQ
QLKAQGNGGGLQNTYNGSSQFTTYSSKVDGNKNPRTLGGNGESKDLSQAL
IGGQTSSDIMGNVNASNSIINLASEPLGGVFNQKGGIDVGGAPAITTQGQ
VTYLGSYSGNNSIPIGQISSNLFASTLLGQREKFDDYSVFFGGFIEADAQ
AWFGSAVTKVQNAGQLSSNGQNIYLTSANLYFLSNLGHYVTAQFDFDTNE
SGSFSNLDISPFFVTAGRNKLSVGSYGGGGTWTSGITKFLSPNQVTNVSI
DYKDQVWNANIAVFGSDDRRANFSTGLFYADSWTPNLAAGFNVGYVFNIA
GAGNSSIANSLANLNRSSDNVGALNVDGNLTYAIWDGFLNLGAGWASTTT
KEDFNNNGGSVLAGAWYGALNYSAILGGRNTNFGVTYGQSYNAAAIPMET
ANASPTFGQTASGIKQQLIFSAQRAYFDDNVLFGPEYAYQRLYTGEHMNT
ITLDMSVYVTSHHHHHH

Figure 16:
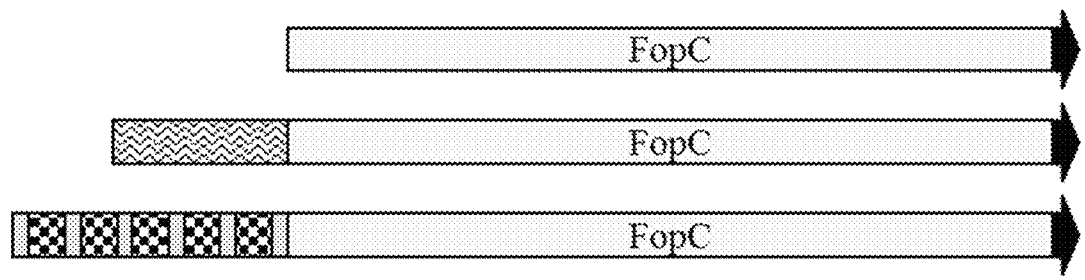
FIG. 16 depicts schematically the fusion protein constructs of *Escherichia coli* strains expressing 6×His tagged FopC, 6×His tagged FopC fused to SUMO and 6×His tagged FopC fused to syn18×5.

The syn18×5 sequence enhances expression of FopC antigen in E. coli. FIG. 16 shows schematically the molecular constructs used in this example. FopC was tagged at the carboxy terminus with a 6×His tag (black), and either expressed without an amino terminal fusion partner, or fused in-frame with SUMO (wavy lines), or with syn18 (checkerboard pattern).

Figure 17:
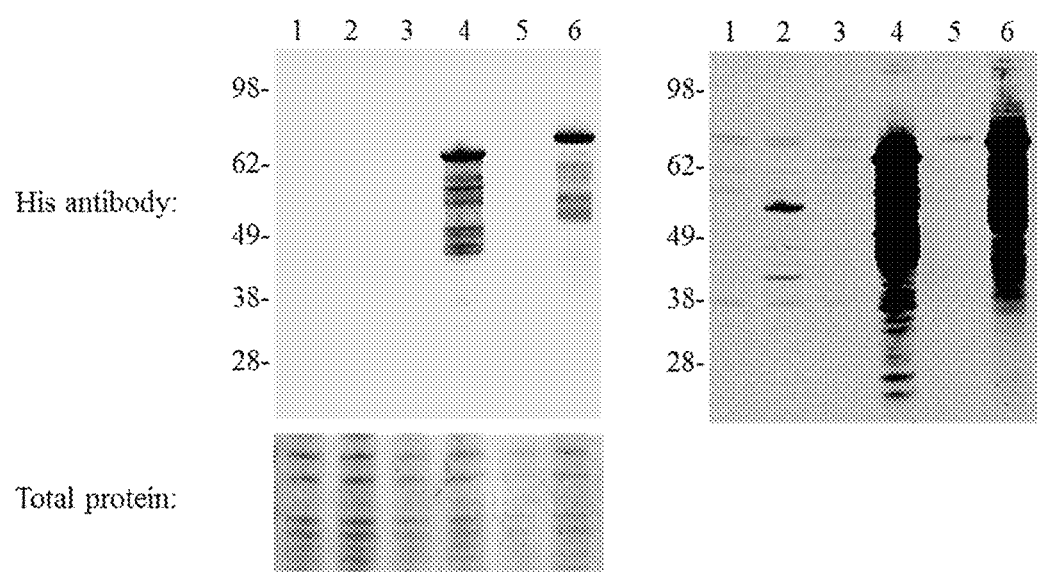
FIG. 17 depicts intracellular Western blot results for fusion protein expression of 6×His tagged FopC, 6×His tagged FopC fused to SUMO and 6×His tagged FopC fused to syn18×5 by *Escherichia coli*.

FIG. 17 depicts the intracellular Western blot of fusion protein expression, where the second copy of the blot to the right has been adjusted to allow visualization of the untagged FopC protein in lane 2. Expression level was normalized to matched bands on the total protein blot (bottom blot). The expression of Syn18×5 fused to FopC was greater than that of the SUMO fused FopC. This is summarized in the following table:

| Lane | Strain | Predicted kDa | condition | Normalized FopC level |
|---|---|---|---|---|
| 1 | FopC | 56.5 | Uninduced | 0 |
| 2 | FopC | 56.5 | Induced | 0.13 |
| 3 | SUMO-FopC | 69.8 | Uninduced | 0 |
| 4 | SUMO-FopC | 69.8 | Induced | 72.6 |
| 5 | Syn18x5-FopC | 76.3 | Uninduced | 0.1 |
| 6 | Syn18x5-FopC | 76.3 | Induced | 92 |

Figure 18:
FIG. 18 depicts schematically the fusion protein constructs of nine independent neoantigenic sequences with or without syn18×5.

Example 12: Expression of Multiple Neoantigenic Sequences Linked to the Carboxy or Amino Terminus of the Enhancer Sequence in Listeria This example was carried out similarly as described in Example 2. Constructs were prepared for expression in Listeria, where the fusion protein comprises ActAN100*, a polypeptide comprising 9 separate predicted neoantigenic sequences from a subject, and with or without the syn18×5 enhancer sequence. These constructs are shown in FIG. 18, wherein, when present, the syn18×5 sequence is between the ActAN100* sequence and the sequence comprising 9 antigenic sequences. Each neoantigenic sequence is numbered 1-9, and the cleaver sequences flanking each neoantigen is represented as A (SEQ ID NO: 7), B (SEQ ID NO: 14), C (SEQ ID NO: 76), C2 (SEQ ID NO: 15) or D (SEQ ID NO: 4). In BH5998 and BH6000, each predicted neoantigenic sequence is a minimal peptide, while in the other four strains, each neoantigenic sequence is 25 amino acids comprising each minimal peptide sequence. Strains BH5990 and BH6002 include the cleaver sequences, while BH5992 and BH6008 lack the cleaver sequences between each neoantigen sequence. Within each construct pair (with and without Syn18×5) the Syn18×5 shows higher expression than the strain without the enhancer sequence. The strains containing cleaver sequences flanking each neoantigen sequence show higher expression than those without the cleaver sequence. Relative expression based on the ActA/p60 ratio is set arbitrarily at 1 for the lowest expressing construct; n.a.: not applicable; n.c.: not calculated (denominator 0). This is summarized in the following table:

| Strain | Antigen Expression Cassette | Predicted kDa | Relative expression | Fold increase with Syn18 |
|---|---|---|---|---|
| BH5988 | ActAN100*-12-036-001A | 33.2 | 1 | — |
| BH6000 | ActAN100*-syn18-12-036-001A | 51 | 69 | 69x |
| BH5990 | ActAN100*-12-036-001B | 40.6 | 8 | — |
| BH6002 | ActAN100*-syn18-12-036-001B | 58.3 | 233 | 30x |
| BH5992 | ActAN100*-12-036-001C | 30.9 | 0 | — |
| BH6008 | ActAN100*-syn18-12-036-001C | 48.6 | 31 | n.c. |

Figure 19:
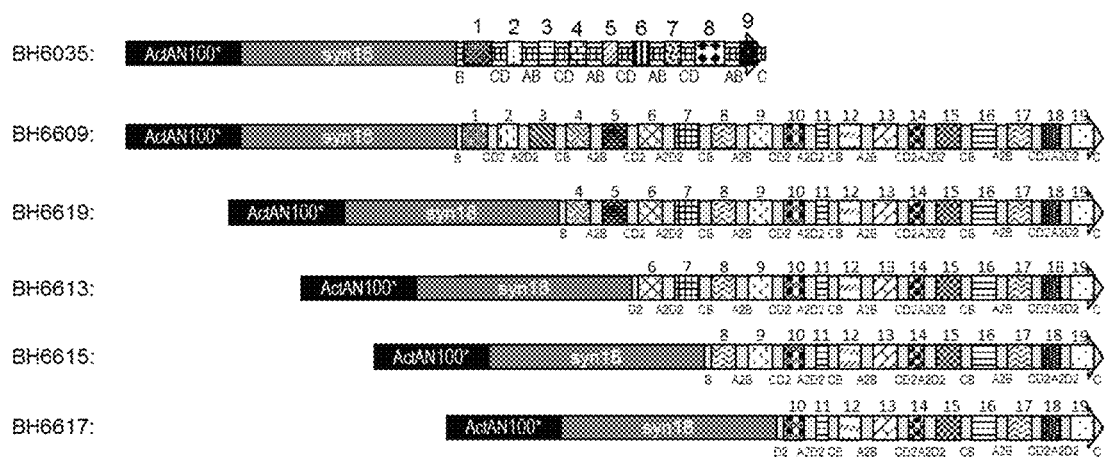
FIG. 19 depicts schematically the fusion protein constructs with varying number of independent neoantigenic sequences with syn18×5.

Additional constructs were prepared for expression in Listeria, where the fusion protein comprises ActAN100* linked to the syn18×5 enhancer sequence, which is linked to a polypeptide comprising up to 19 separate predicted neoantigenic sequences from one subject (BH6609-19 neoantigens, BH6619-16 neoantigens, BH6613-14 neoantigens, BH6615-12 neoantigens and BH6617-10 neoantigens), and 9 separate predicted neoantigenic sequences from another subject (BH6035). These constructs are shown in FIG. 19, wherein each neoantigenic sequence is numbered 1-19 or 1-9, with a cleaver sequence flanking each neoantigen, where the cleaver sequence is represented as A (SEQ ID NO: 7), B (SEQ ID NO: 14), C (SEQ ID NO: 76), D (SEQ ID NO: 4), A2 (SEQ ID NO: 2) or D2 (SEQ ID NO: 75). Each neoantigenic sequence is a predicted neoantigen with a subject mutational sequence wherein the mutation is in the middle of a 25 amino acid sequence. The Expression is compared to the Listeria strain without the fusion protein construct, and demonstrates that the polypeptide comprising multiple antigenic sequences expresses the fusion protein. Relative expression based on the ActA/p60 ratio is set arbitrarily at 1 for the lowest expressing construct; n.a.: not applicable. This is summarized in the following table:

| Strain | Antigen Expression Cassette | Predicted kDa | Relative expression |
|---|---|---|---|
| Lm11 | None | n.a. | 0 |
| BH6035 | ActAN100*-syn18-12-036-001D | 59.7 | 11.6 |
| BH6609 | ActAN100*-syn18-12-036-002 (1-19) | 94.6 | 1.2 |
| BH6619 | ActAN100*-syn18-12-036-002 (4-19) | 83.2 | 1.0 |
| BH6613 | ActAN100*-syn18-12-036-002 (6-19) | 75.6 | 2.9 |
| BH6615 | ActAN100*-syn18-12-036-002 (8-19) | 67.5 | 6.4 |
| BH6617 | ActAN100*-syn18-12-036-002 (10-19) | 59.4 | 11.6 |

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations that is not specifically disclosed herein. Thus, for example, in each instance herein any of the terms "comprising", "consisting essentially of" and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A nucleic acid molecule that encodes a fusion protein, wherein said fusion protein comprises (i) a first amino acid sequence comprising one or more copies of an enhancer amino acid sequence, wherein each enhancer amino acid sequence present in the fusion protein is independently selected from the group consisting of SEQ ID NO: 1 or a sequence having 1-5 conservative amino acid substitutions thereof and SEQ ID NO: 37 or a sequence having 1-5 conservative amino acid substitutions thereof, and (ii) a second amino acid sequence encoding a polypeptide of interest linked to the amino terminus or carboxyl terminus of the first amino acid sequence.

2. The nucleic acid molecule according to claim 1, further comprising one or more regulatory elements that mediate expression of the fusion protein in a host cell.

3. The nucleic acid molecule according to claim 2, wherein the regulatory elements comprise a *Listeria monocytogenes* actA promoter.

4. The nucleic acid molecule according to claim 1, wherein the polypeptide of interest comprises a tumor antigen.

5. The nucleic acid molecule according to claim 1, wherein the first amino acid sequence comprises one or more cleaver amino acid sequences, wherein each cleaver amino acid sequence is linked to at least one of the one or more enhancer amino acid sequences.

6. The nucleic acid molecule according to claim 5, wherein each enhancer amino acid sequence is linked to one of the cleaver amino acid sequences at its amino terminus and another of the cleaver amino acid sequences at its carboxy terminus.

7. The nucleic acid molecule according to claim 6 wherein the first amino acid sequence comprises 1, 2, 3, 4 or 5 copies of SEQ ID NO: 1 or 1, 2, 3, 4 or 5 copies of SEQ ID NO: 37.

8. The nucleic acid molecule according to claim 7, wherein each cleaver amino acid sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

9. The nucleic acid molecule according to claim 1, wherein the first amino acid sequence is selected from the group consisting of SEQ ID NO: 31, SEQ ID NO: 29, SEQ ID NO: 69, SEQ ID NO: 70, SEQ ID NO: 71, SEQ ID NO: 72, SEQ ID NO: 73, SEQ ID NO: 74, SEQ ID NO: 35, and SEQ ID NO: 33.

10. The nucleic acid molecule according to claim 1, wherein the first amino acid sequence is SEQ ID NO: 35.

11. The nucleic acid molecule according to claim 1, wherein the second amino acid sequence comprises one or more antigenic sequences.

12. The nucleic acid molecule according to claim 11, wherein the second amino acid sequence comprises one or more cleaver amino acid sequences, wherein each cleaver amino acid sequence is linked to at least one of the one or more antigenic sequences.

13. The nucleic acid molecule according to claim 12, wherein each antigenic sequence is linked to one of the cleaver amino acid sequence at its amino terminus and another of the cleaver amino acid sequence at its carboxy terminus.

14. The nucleic acid molecule according to claim 13, wherein each cleaver amino acid sequence is independently selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 75, and SEQ ID NO: 76.

15. The nucleic acid molecule according to claim 1, wherein the fusion protein comprises a secretory signal sequence.

16. The nucleic acid molecule according to claim 15, wherein the carboxy terminus of said secretory signal sequence is linked to the amino terminus of the first amino acid sequence, and the carboxy terminus of the first amino acid sequence is linked to the amino terminus of the second amino acid sequence.

17. The nucleic acid molecule according to claim 15, wherein the carboxy terminus of said secretory signal sequence is linked to the amino terminus of the second amino acid sequence, and the carboxy terminus of the second amino acid sequence is linked to the amino terminus of the first amino acid sequence.

18. The nucleic acid molecule according to claim 16, wherein the secretory signal sequence is a *Listeria monocytogenes* secretory signal sequence.

19. The nucleic acid molecule according to claim 18, wherein the secretory signal sequence is an actin assembly-inducing protein (ActA) or listeriolysin O (LLO) secretory signal sequence.

20. The nucleic acid molecule according to claim 19, wherein the ActA signal sequence is encoded by a sequence selected from the group consisting of SEQ ID NO: 25, SEQ ID NO: 26, SEQ ID NO: 27, and SEQ ID NO: 28, or the LLO signal sequence is encoded by a sequence selected from the group consisting of SEQ ID NO: 40, SEQ ID NO: 40 from which the sequence SEQ ID NO: 67 is deleted, and SEQ ID NO: 40 in which the sequence SEQ ID NO: 67 is replaced with the dipeptide Lys-Glu (KE).

21. The nucleic acid molecule according to claim 19, wherein the secretory signal sequence is SEQ ID NO:28.

22. A host cell comprising the nucleic acid molecule of claim 1 integrated into the genome of the host cell, wherein the host cell expresses the fusion protein.

23. A composition comprising the host cell according to claim 22 and a pharmaceutically acceptable excipient.

24. A method of expressing a polypeptide of interest from a host cell, comprising:
introducing into the host cell an expression construct comprising the nucleic acid molecule according to claim 1, wherein the fusion protein is operably linked to one or more regulatory elements which mediate expression, and optionally secretion, of the fusion protein in the host cell, wherein the host cell is optionally a bacterium, and wherein the bacterium is optionally *Listeria monocytogenes*.

25. A fusion protein comprising:
a first amino acid sequence comprising one or more copies of an enhancer amino acid sequence, each enhancer amino acid sequence independently selected from the group consisting of SEQ ID NO: 1 or a sequence having 1-5 conservative amino acid substitutions thereof and SEQ ID NO: 37 or a sequence having 1-5 conservative amino acid substitutions thereof, and (ii) a second amino acid sequence encoding a polypeptide of interest linked to the amino terminus or carboxyl terminus of the first amino acid sequence.

26. A method of treating cancer or a viral disease in an individual in need thereof, comprising:
expressing a fusion protein according to claim 25 within the individual, wherein the polypeptide of interest comprises one or more antigenic sequences present on cancer cells or virally infected cells present in the individual.

* * * * *

```
                        SEQUENCE LISTING

<160> NUMBER OF SEQ ID NOS: 77

<210> SEQ ID NO 1
    <211> LENGTH: 18
    <212> TYPE: PRT
    <213> ORGANISM: Artificial Sequence
    <220> FEATURE:
    <223> OTHER INFORMATION: Synthetic

<400> SEQUENCE: 1

Glu Ser Asn Gln Ser Val Glu Asp Lys His Asn Glu Phe Met Leu Thr
    1               5                   10                  15

Glu Tyr

<210> SEQ ID NO 2
    <211> LENGTH: 6
    <212> TYPE: PRT
    <213> ORGANISM: Artificial Sequence
    <220> FEATURE:
    <223> OTHER INFORMATION: Synthetic

<400> SEQUENCE: 2

Ala Asp Gly Ser Val Lys
    1               5

<210> SEQ ID NO 3
    <211> LENGTH: 5
    <212> TYPE: PRT
    <213> ORGANISM: Artificial Sequence
    <220> FEATURE:
    <223> OTHER INFORMATION: Synthetic

<400> SEQUENCE: 3

Ala Ser Lys Val Ala
    1               5

<210> SEQ ID NO 4
    <211> LENGTH: 5
    <212> TYPE: PRT
    <213> ORGANISM: Artificial Sequence
    <220> FEATURE:
    <223> OTHER INFORMATION: Synthetic

<400> SEQUENCE: 4

Leu Ser Lys Val Leu
    1               5

<210> SEQ ID NO 5
    <211> LENGTH: 5
    <212> TYPE: PRT
    <213> ORGANISM: Artificial Sequence
    <220> FEATURE:
    <223> OTHER INFORMATION: Synthetic

<400> SEQUENCE: 5
```

Ala Ser Lys Val Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gly Asp Gly Ser Ile Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Ala Asp Gly Ser Val
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Leu Ala Lys Ser Leu
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Ala Asp Leu Ala Val Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Ala Ser Val Val Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Gly Ile Gly Ser Ile Ala

```
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Gly Val Glu Lys Ile
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Asn Ala Ala Asn Lys Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Asp Gly Ser Lys Lys Ala
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Gly Asp Gly Asn Lys Lys
1               5

<210> SEQ ID NO 16

<400> SEQUENCE: 16

000

<210> SEQ ID NO 17
<211> LENGTH: 32
<212> TYPE: PRT
<213> ORGANISM: Artificial Sequence
<220> FEATURE:
<223> OTHER INFORMATION: Synthetic

<400> SEQUENCE: 17

Ala Ser Lys Val Leu Pro Ala Ser Arg Ala Leu Glu Glu Lys Lys Gly
1               5                   10                  15

Asn Tyr Val Val Thr Asp His Gly Ser Cys Ala Asp Gly Ser Val Lys
            20                  25                  30

<210> SEQ ID NO 18
```

```
<211> LENGTH: 5
<212> TYPE: PRT
<213> ORGANISM: Listeria monocytogenes

<400> SEQUENCE: 18

Thr Glu Ala Lys Asp
1               5

<210> SEQ ID NO 19
<211> LENGTH: 5
<212> TYPE: PRT
<213> ORGANISM: Lactococcus lactis

<400> SEQUENCE: 19

Val Tyr Ala Asp Thr
1               5

<210> SEQ ID NO 20
<211> LENGTH: 5
<212> TYPE: PRT
<213> ORGANISM: Bacillus anthracis

<400> SEQUENCE: 20

Ile Gln Ala Glu Val
1               5

<210> SEQ ID NO 21
<211> LENGTH: 5
<212> TYPE: PRT
<213> ORGANISM: Listeria monocytogenes

<400> SEQUENCE: 21

Ala Ser Ala Ser Thr
1               5

<210> SEQ ID NO 22
<211> LENGTH: 5
<212> TYPE: PRT
<213> ORGANISM: Listeria monocytogenes

<400> SEQUENCE: 22

Val Gly Ala Phe Gly
1               5

<210> SEQ ID NO 23
<211> LENGTH: 5
<212> TYPE: PRT
<213> ORGANISM: Bacillus anthracis

<400> SEQUENCE: 23

Ala Phe Ala Glu Asp
1               5

<210> SEQ ID NO 24
<211> LENGTH: 5
<212> TYPE: PRT
<213> ORGANISM: Staphylococcus aureus

<400> SEQUENCE: 24

Val Gln Ala Ala Glu
1               5

<210> SEQ ID NO 25
<211> LENGTH: 100
<212> TYPE: PRT
```

<213> ORGANISM: Artificial Sequence
<220> FEATURE:
<223> OTHER INFORMATION: Synthetic

<400> SEQUENCE: 25

```
Val Gly Leu Asn Arg Phe Met Arg Ala Met Met Val Val Phe Ile Thr
1               5                   10                  15
Ala Asn Cys Ile Thr Ile Asn Pro Asp Ile Ile Phe Ala Ala Thr Asp
            20                  25                  30
Ser Glu Asp Ser Ser Leu Asn Thr Asp Glu Trp Glu Glu Lys Thr
        35                  40                  45
Glu Glu Gln Pro Ser Glu Val Asn Thr Gly Pro Arg Tyr Glu Thr Ala
    50                  55                  60
Arg Glu Val Ser Ser Arg Asp Ile Glu Glu Leu Glu Lys Ser Asn Lys
65                  70                  75                  80
Val Lys Asn Thr Asn Lys Ala Asp Leu Ile Ala Met Leu Lys Ala Lys
                85                  90                  95
Ala Glu Lys Gly
            100
```

<210> SEQ ID NO 26
<211> LENGTH: 102
<212> TYPE: PRT
<213> ORGANISM: Artificial Sequence
<220> FEATURE:
<223> OTHER INFORMATION: Synthetic

<400> SEQUENCE: 26

```
Val Gly Leu Asn Arg Phe Met Arg Ala Met Met Val Val Phe Ile Thr
1               5                   10                  15
Ala Asn Cys Ile Thr Ile Asn Pro Asp Ile Ile Phe Ala Ala Thr Asp
            20                  25                  30
Ser Glu Asp Ser Ser Leu Asn Thr Asp Glu Trp Glu Glu Lys Thr
        35                  40                  45
Glu Glu Gln Pro Ser Glu Val Asn Thr Gly Pro Arg Tyr Glu Thr Ala
    50                  55                  60
Arg Glu Val Ser Ser Arg Asp Ile Glu Glu Leu Glu Lys Ser Asn Lys
65                  70                  75                  80
Val Lys Asn Thr Asn Lys Ala Asp Leu Ile Ala Met Leu Lys Ala Lys
                85                  90                  95
Ala Glu Lys Gly Gly Ser
            100
```

<210> SEQ ID NO 27
<211> LENGTH: 86
<212> TYPE: PRT
<213> ORGANISM: Artificial Sequence
<220> FEATURE:
<223> OTHER INFORMATION: Synthetic

<400> SEQUENCE: 27

```
Val Gly Leu Asn Arg Phe Met Arg Ala Met Met Val Val Phe Ile Thr
1               5                   10                  15
Ala Asn Cys Ile Thr Ile Asn Pro Asp Ile Ile Phe Ala Ala Thr Asp
            20                  25                  30
Ser Glu Asp Ser Ser Leu Asn Thr Asp Glu Trp Glu Glu Tyr Glu
        35                  40                  45
Thr Ala Arg Glu Val Ser Ser Arg Asp Ile Glu Glu Leu Glu Lys Ser
    50                  55                  60
```

```
Asn Lys Val Lys Asn Thr Asn Lys Ala Asp Gln Asp Asn Lys Arg Lys
 65                  70                  75                  80

Ala Lys Ala Glu Lys Gly
                85
```

<210> SEQ ID NO 28
<211> LENGTH: 86
<212> TYPE: PRT
<213> ORGANISM: Artificial Sequence
<220> FEATURE:
<223> OTHER INFORMATION: Synthetic

<400> SEQUENCE: 28

```
Met Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Tyr Glu
         35                  40                  45

Thr Ala Arg Glu Val Ser Ser Arg Asp Ile Glu Glu Leu Glu Lys Ser
     50                  55                  60

Asn Lys Val Lys Asn Thr Asn Lys Ala Asp Gln Asp Asn Lys Arg Lys
 65                  70                  75                  80

Ala Lys Ala Glu Lys Gly
                85
```

<210> SEQ ID NO 29
<211> LENGTH: 32
<212> TYPE: PRT
<213> ORGANISM: Artificial Sequence
<220> FEATURE:
<223> OTHER INFORMATION: Synthetic

<400> SEQUENCE: 29

```
Ala Ser Lys Val Leu Pro Ala Ser Arg Ala Val Asp Asp His His Ala
 1               5                  10                  15

Gln Phe Leu Leu Ser Glu Lys Gly Ser Cys Ala Asp Gly Ser Val Lys
                20                  25                  30
```

<210> SEQ ID NO 30
<211> LENGTH: 19
<212> TYPE: PRT
<213> ORGANISM: Artificial Sequence
<220> FEATURE:
<223> OTHER INFORMATION: Synthetic

<400> SEQUENCE: 30

```
Ala Ser Lys Val Leu Pro Ala Ser Arg Ala Gly Ser Cys Ala Asp Gly
 1               5                  10                  15

Ser Val Lys
```

<210> SEQ ID NO 31
<211> LENGTH: 32
<212> TYPE: PRT
<213> ORGANISM: Artificial Sequence
<220> FEATURE:
<223> OTHER INFORMATION: Synthetic

<400> SEQUENCE: 31

```
Ala Ser Lys Val Leu Glu Ser Asn Gln Ser Val Glu Asp Lys His Asn
 1               5                  10                  15
```

```
Glu Phe Met Leu Thr Glu Tyr Gly Ser Cys Ala Asp Gly Ser Val Lys
            20                  25                  30
```

<210> SEQ ID NO 32
<211> LENGTH: 162
<212> TYPE: PRT
<213> ORGANISM: Artificial Sequence
<220> FEATURE:
<223> OTHER INFORMATION: Synthetic

<400> SEQUENCE: 32

```
Ala Ser Lys Val Leu Pro Ala Ser Arg Ala Leu Glu Glu Lys Lys Gly
1               5                   10                  15
Asn Tyr Val Val Thr Asp His Gly Ser Cys Ala Asp Gly Ser Val Lys
            20                  25                  30
Thr Ser Ala Ser Lys Val Ala Pro Ala Ser Arg Ala Leu Glu Glu Lys
        35                  40                  45
Lys Gly Asn Tyr Val Val Thr Asp His Gly Ser Cys Gly Asp Gly Ser
    50                  55                  60
Ile Lys Leu Ser Lys Val Leu Pro Ala Ser Arg Ala Leu Glu Glu Lys
65                  70                  75                  80
Lys Gly Asn Tyr Val Val Thr Asp His Gly Ser Cys Ala Asp Gly Ser
                85                  90                  95
Val Lys Ala Ser Lys Val Ala Pro Ala Ser Arg Ala Leu Glu Glu Lys
            100                 105                 110
Lys Gly Asn Tyr Val Val Thr Asp His Gly Ser Cys Gly Asp Gly Ser
        115                 120                 125
Ile Lys Leu Ser Lys Val Leu Pro Ala Ser Arg Ala Leu Glu Glu Lys
    130                 135                 140
Lys Gly Asn Tyr Val Val Thr Asp His Gly Ser Cys Ala Asp Gly Ser
145                 150                 155                 160
Val Lys
```

<210> SEQ ID NO 33
<211> LENGTH: 162
<212> TYPE: PRT
<213> ORGANISM: Artificial Sequence
<220> FEATURE:
<223> OTHER INFORMATION: Synthetic

<400> SEQUENCE: 33

```
Ala Ser Lys Val Leu Pro Ala Ser Arg Ala Val Asp Asp His His Ala
1               5                   10                  15
Gln Phe Leu Leu Ser Glu Lys Gly Ser Cys Ala Asp Gly Ser Val Lys
            20                  25                  30
Thr Ser Ala Ser Lys Val Ala Pro Ala Ser Arg Ala Val Asp Asp His
        35                  40                  45
His Ala Gln Phe Leu Leu Ser Glu Lys Gly Ser Cys Gly Asp Gly Ser
    50                  55                  60
Ile Lys Leu Ser Lys Val Leu Pro Ala Ser Arg Ala Val Asp Asp His
65                  70                  75                  80
His Ala Gln Phe Leu Leu Ser Glu Lys Gly Ser Cys Ala Asp Gly Ser
                85                  90                  95
Val Lys Ala Ser Lys Val Ala Pro Ala Ser Arg Ala Val Asp Asp His
            100                 105                 110
His Ala Gln Phe Leu Leu Ser Glu Lys Gly Ser Cys Gly Asp Gly Ser
        115                 120                 125
```

```
Ile Lys Leu Ser Lys Val Leu Pro Ala Ser Arg Ala Val Asp Asp His
            130                 135                 140

His Ala Gln Phe Leu Leu Ser Glu Lys Gly Ser Cys Ala Asp Gly Ser
145                 150                 155                 160

Val Lys

<210> SEQ ID NO 34
<211> LENGTH: 97
<212> TYPE: PRT
<213> ORGANISM: Artificial Sequence
<220> FEATURE:
<223> OTHER INFORMATION: Synthetic

<400> SEQUENCE: 34

Ala Ser Lys Val Leu Pro Ala Ser Arg Ala Gly Ser Cys Ala Asp Gly
1               5                   10                  15

Ser Val Lys Thr Ser Ala Ser Lys Val Ala Pro Ala Ser Arg Ala Gly
            20                  25                  30

Ser Cys Gly Asp Gly Ser Ile Lys Leu Ser Lys Val Leu Pro Ala Ser
            35                  40                  45

Arg Ala Gly Ser Cys Ala Asp Gly Ser Val Lys Ala Ser Lys Val Ala
50                  55                  60

Pro Ala Ser Arg Ala Gly Ser Cys Gly Asp Gly Ser Ile Lys Leu Ser
65                  70                  75                  80

Lys Val Leu Pro Ala Ser Arg Ala Gly Ser Cys Ala Asp Gly Ser Val
                85                  90                  95

Lys

<210> SEQ ID NO 35
<211> LENGTH: 162
<212> TYPE: PRT
<213> ORGANISM: Artificial Sequence
<220> FEATURE:
<223> OTHER INFORMATION: Synthetic

<400> SEQUENCE: 35

Ala Ser Lys Val Leu Glu Ser Asn Gln Ser Val Glu Asp Lys His Asn
1               5                   10                  15

Glu Phe Met Leu Thr Glu Tyr Gly Ser Cys Ala Asp Gly Ser Val Lys
            20                  25                  30

Thr Ser Ala Ser Lys Val Ala Glu Ser Asn Gln Ser Val Glu Asp Lys
            35                  40                  45

His Asn Glu Phe Met Leu Thr Glu Tyr Gly Ser Cys Gly Asp Gly Ser
50                  55                  60

Ile Lys Leu Ser Lys Val Leu Glu Ser Asn Gln Ser Val Glu Asp Lys
65                  70                  75                  80

His Asn Glu Phe Met Leu Thr Glu Tyr Gly Ser Cys Ala Asp Gly Ser
                85                  90                  95

Val Lys Ala Ser Lys Val Ala Glu Ser Asn Gln Ser Val Glu Asp Lys
            100                 105                 110

His Asn Glu Phe Met Leu Thr Glu Tyr Gly Ser Cys Gly Asp Gly Ser
            115                 120                 125

Ile Lys Leu Ser Lys Val Leu Glu Ser Asn Gln Ser Val Glu Asp Lys
            130                 135                 140

His Asn Glu Phe Met Leu Thr Glu Tyr Gly Ser Cys Ala Asp Gly Ser
145                 150                 155                 160

Val Lys
```

<210> SEQ ID NO 36
<211> LENGTH: 485
<212> TYPE: DNA
<213> ORGANISM: Artificial Sequence
<220> FEATURE:
<223> OTHER INFORMATION: Synthetic

<400> SEQUENCE: 36

```
ggtaccggga agcagttggg gttaactgat taacaaatgt tagagaaaaa ttaattctcc     60
aagtgatatt cttaaaataa ttcatgaata ttttttctta tattagctaa ttaagaagat    120
aattaactgc taatccaatt tttaacggaa taaattagtg aaaatgaagg ccgaattttc    180
cttgttctaa aaaggttgta ttagcgtatc acgaggaggg agtataagtg ggattaaata    240
gatttatgcg tgcgatgatg gtagttttca ttactgccaa ctgcattacg attaaccccg    300
acataatatt tgcagcgaca gatagcgaag attccagtct aaacacagat gaatgggaag    360
aagaatacga aactgcacgt gaagtaagtt cacgtgatat tgaggaacta gaaaaatcga    420
ataaagtgaa aaatacgaac aaagcagacc aagataataa acgtaaagca aagcagaga    480
aaggt                                                                485
```

<210> SEQ ID NO 37
<211> LENGTH: 18
<212> TYPE: PRT
<213> ORGANISM: Artificial Sequence
<220> FEATURE:
<223> OTHER INFORMATION: Synthetic

<400> SEQUENCE: 37

Pro Ala Ser Arg Ala Val Asp Asp His His Ala Gln Phe Leu Leu Ser
1               5                   10                  15

Glu Lys

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ser Ile Ile Asn Phe Glu Lys Leu
1               5

<210> SEQ ID NO 39
<211> LENGTH: 25
<212> TYPE: PRT
<213> ORGANISM: Artificial Sequence
<220> FEATURE:
<223> OTHER INFORMATION: Synthetic

<400> SEQUENCE: 39

Met Lys Lys Ile Met Leu Val Phe Ile Thr Leu Ile Leu Val Ser Leu
1               5                   10                  15

Pro Ile Ala Gln Gln Thr Glu Ala Lys
            20                  25

<210> SEQ ID NO 40
<211> LENGTH: 441
<212> TYPE: PRT
<213> ORGANISM: Artificial Sequence
<220> FEATURE:

<223> OTHER INFORMATION: Synthetic

<400> SEQUENCE: 40

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400
```

```
Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
        420                 425                 430

Ile Ser Trp Asp Glu Val Asn Tyr Asp
        435                 440

<210> SEQ ID NO 41
<211> LENGTH: 29
<212> TYPE: PRT
<213> ORGANISM: Artificial Sequence
<220> FEATURE:
<223> OTHER INFORMATION: Synthetic

<400> SEQUENCE: 41

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Met Lys Lys Ile Met Leu Val Phe Ile Thr Leu Ile Leu Val Ser Leu
1               5                   10                  15

Pro Ile Ala Gln Gln Thr Glu
            20

<210> SEQ ID NO 43
<211> LENGTH: 971
<212> TYPE: DNA
<213> ORGANISM: Artificial Sequence
<220> FEATURE:
<223> OTHER INFORMATION: Synthetic

<400> SEQUENCE: 43
gggaagcagt tggggttaac tgattaacaa atgttagaga aaaattaatt ctccaagtga      60
tattcttaaa ataattcatg aatattttt cttatattag ctaattaaga agataattaa     120
ctgctaatcc aattttaac ggaataaatt agtgaaaatg aaggccgaat tttccttgtt     180 ctaaaaggt tgtattagcg tatcacgagg agggagtata agtgggatta aatagattta     240
tgcgtgcgat gatggtagtt ttcattactg ccaactgcat tacgattaac cccgacataa     300
tatttgcagc gacagatagc gaagattcca gtctaaacac agatgaatgg gaagaagaat     360
acgaaactgc acgtgaagta agttcacgtg atattgagga actagaaaaa tcgaataaag     420
tgaaaaatac gaacaaagca gaccaagata taaacgtaa agcaaaagca gagaaaggtg     480
gatctgcaag caaagtattg ccagctagtc gtgcagtgga tgatcatcac gcgcagtttc     540
tattatccga aaaaggatcg tgtgccgatg gctcagtaaa gactagcgcg agcaaagtgg     600
cccctgcatc acgagcagta gacgaccacc atgctcaatt cttactaagc gagaaaggta     660
gctgcggaga tggttcaatt aaattatcaa aagtcttacc agcatctaga gctgtggacg     720
atcaccacgc tcagttccta ctatccgaga aaggaagttg tgctgacgga agtgttaaag     780
cgtcgaaagt agctccagct tctcgcgcag tagatgacca tcatgcgcaa ttttattaa     840
```

| gcgaaaaagg tagttgtggt gatggctcga tcaaattgtc aaaagttcta ccggcttctc | 900 |
|---|---|
| gtgcggtgga tgatcaccat gctcagtttc tactaagcga gaaaggctct tgcgcggatg | 960 |
| gttccgttaa a | 971 |

<210> SEQ ID NO 44
<211> LENGTH: 250
<212> TYPE: PRT
<213> ORGANISM: Artificial Sequence
<220> FEATURE:
<223> OTHER INFORMATION: Synthetic

<400> SEQUENCE: 44

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Pro Ala Ser
                85                  90                  95

Arg Ala Val Asp Asp His His Ala Gln Phe Leu Leu Ser Glu Lys Gly
            100                 105                 110

Ser Cys Ala Asp Gly Ser Val Lys Thr Ser Ala Ser Lys Val Ala Pro
        115                 120                 125

Ala Ser Arg Ala Val Asp Asp His His Ala Gln Phe Leu Leu Ser Glu
    130                 135                 140

Lys Gly Ser Cys Gly Asp Gly Ser Ile Lys Leu Ser Lys Val Leu Pro
145                 150                 155                 160

Ala Ser Arg Ala Val Asp Asp His His Ala Gln Phe Leu Leu Ser Glu
                165                 170                 175

Lys Gly Ser Cys Ala Asp Gly Ser Val Lys Ala Ser Lys Val Ala Pro
            180                 185                 190

Ala Ser Arg Ala Val Asp Asp His His Ala Gln Phe Leu Leu Ser Glu
        195                 200                 205

Lys Gly Ser Cys Gly Asp Gly Ser Ile Lys Leu Ser Lys Val Leu Pro
    210                 215                 220

Ala Ser Arg Ala Val Asp Asp His His Ala Gln Phe Leu Leu Ser Glu
225                 230                 235                 240

Lys Gly Ser Cys Ala Asp Gly Ser Val Lys
                245                 250
```

<210> SEQ ID NO 45
<211> LENGTH: 776
<212> TYPE: DNA
<213> ORGANISM: Artificial Sequence
<220> FEATURE:
<223> OTHER INFORMATION: Synthetic

<400> SEQUENCE: 45

| gggaagcagt tggggttaac tgattaacaa atgttagaga aaaattaatt ctccaagtga | 60 |
|---|---|
| tattcttaaa ataattcatg aatatttttt cttatattag ctaattaaga agataattaa | 120 |
| ctgctaatcc aatttttaac ggaataaatt agtgaaaatg aaggccgaat tttccttgtt | 180 |

```
ctaaaaaggt tgtattagcg tatcacgagg agggagtata agtgggatta aatagattta    240
tgcgtgcgat gatggtagtt ttcattactg ccaactgcat tacgattaac cccgacataa    300
tatttgcagc gacagatagc gaagattcca gtctaaacac agatgaatgg gaagaagaat    360
acgaaactgc acgtgaagta agttcacgtg atattgagga actagaaaaa tcgaataaag    420
tgaaaaatac gaacaaagca gaccaagata ataaacgtaa agcaaaagca gagaaggtg     480 gatctgcaag caaagtattg ccagctagtc gtgcaggatc gtgtgccgat ggctcagtaa    540
agactagcgc gagcaaagtg gcccctgcat cacgagcagg tagctgcgga gatggttcaa    600
ttaaattatc aaaagtctta ccagcatcta gagctgaag  ttgtgctgac ggaagtgtta    660
aagcgtcgaa agtagctcca gcttctcgcg caggtagttg tggtgatggc tcgatcaaat    720
tgtcaaaagt ctaccggct ctcgtgcgg gctcttgcgc ggatggttcc gttaaa          776
```

<210> SEQ ID NO 46
<211> LENGTH: 185
<212> TYPE: PRT
<213> ORGANISM: Artificial Sequence
<220> FEATURE:
<223> OTHER INFORMATION: Synthetic

<400> SEQUENCE: 46

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Pro Ala Ser
                85                  90                  95

Arg Ala Gly Ser Cys Ala Asp Gly Ser Val Lys Thr Ser Ala Ser Lys
            100                 105                 110

Val Ala Pro Ala Ser Arg Ala Gly Ser Cys Gly Asp Gly Ser Ile Lys
        115                 120                 125

Leu Ser Lys Val Leu Pro Ala Ser Arg Ala Gly Ser Cys Ala Asp Gly
    130                 135                 140

Ser Val Lys Ala Ser Lys Val Ala Pro Ala Ser Arg Ala Gly Ser Cys
145                 150                 155                 160

Gly Asp Gly Ser Ile Lys Leu Ser Lys Val Leu Pro Ala Ser Arg Ala
                165                 170                 175

Gly Ser Cys Ala Asp Gly Ser Val Lys
            180                 185
```

<210> SEQ ID NO 47
<211> LENGTH: 971
<212> TYPE: DNA
<213> ORGANISM: Artificial Sequence
<220> FEATURE:
<223> OTHER INFORMATION: Synthetic

<400> SEQUENCE: 47

```
gggaagcagt tggggttaac tgattaacaa atgttagaga aaaattaatt ctccaagtga    60
```

| | | |
|---|---|---|
| tattcttaaa ataattcatg aatatttttt cttatattag ctaattaaga agataattaa | 120 | |
| ctgctaatcc aatttttaac ggaataaatt agtgaaaatg aaggccgaat tttccttgtt | 180 | |
| ctaaaaaggt tgtattagcg tatcacgagg agggagtata agtgggatta aatagattta | 240 | |
| tgcgtgcgat gatggtagtt ttcattactg ccaactgcat tacgattaac cccgacataa | 300 | |
| tatttgcagc gacagatagc gaagattcca gtctaaacac agatgaatgg gaagaagaat | 360 | |
| acgaaactgc acgtgaagta agttcacgtg atattgagga actagaaaaa tcgaataaag | 420 | |
| tgaaaaatac gaacaaagca gaccaagata ataaacgtaa agcaaaagca gagaaaggtg | 480 | |
| gatctgcaag caaagtattg gaatctaatc aaagcgtaga ggacaagcac aatgagttca | 540 | |
| tgttgacgga gtacggttca tgtgccgatg gctcagtaaa gactagcgcg agcaaagtgg | 600 | |
| ccgagtcaaa tcagtctgtt gaggacaaac ataatgagtt catgttaacg gagtatggta | 660 | |
| gctgtggaga tggttcaatt aaattatcaa aagtcttaga atctaatcag agcgttgagg | 720 | |
| acaagcataa tgagttcatg ttgacggagt acggttcatg tgctgacgga agtgttaaag | 780 | |
| cgtcgaaagt agctgaatca aatcaatctg tagaggacaa acacaatgaa tttatgctaa | 840 | |
| cagaatacgg cagctgcggt gatggctcga tcaaattgtc aaaagttta gaatctaacc | 900 | |
| agagcgttga agataagcac aacgaattta tgttaacgga gtacggttca tgcgcggatg | 960 | |
| gttccgttaa a | 971 | |

<210> SEQ ID NO 48
<211> LENGTH: 250
<212> TYPE: PRT
<213> ORGANISM: Artificial Sequence
<220> FEATURE:
<223> OTHER INFORMATION: Synthetic

<400> SEQUENCE: 48

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Tyr Glu
        35                  40                  45

Thr Ala Arg Glu Val Ser Ser Arg Asp Ile Glu Glu Leu Glu Lys Ser
    50                  55                  60

Asn Lys Val Lys Asn Thr Asn Lys Ala Asp Gln Asp Asn Lys Arg Lys
65                  70                  75                  80

Ala Lys Ala Glu Lys Gly Gly Ser Ala Ser Lys Val Leu Glu Ser Asn
                85                  90                  95

Gln Ser Val Glu Asp Lys His Asn Glu Phe Met Leu Thr Glu Tyr Gly
            100                 105                 110

Ser Cys Ala Asp Gly Ser Val Lys Thr Ser Ala Ser Lys Val Ala Glu
        115                 120                 125

Ser Asn Gln Ser Val Glu Asp Lys His Asn Glu Phe Met Leu Thr Glu
    130                 135                 140

Tyr Gly Ser Cys Gly Asp Gly Ser Ile Lys Leu Ser Lys Val Leu Glu
145                 150                 155                 160

Ser Asn Gln Ser Val Glu Asp Lys His Asn Glu Phe Met Leu Thr Glu
                165                 170                 175

Tyr Gly Ser Cys Ala Asp Gly Ser Val Lys Ala Ser Lys Val Ala Glu
            180                 185                 190

Ser Asn Gln Ser Val Glu Asp Lys His Asn Glu Phe Met Leu Thr Glu

```
                195                 200                 205
Tyr Gly Ser Cys Gly Asp Gly Ser Ile Lys Leu Ser Lys Val Leu Glu
    210                 215                 220

Ser Asn Gln Ser Val Glu Asp Lys His Asn Glu Phe Met Leu Thr Glu
225                 230                 235                 240

Tyr Gly Ser Cys Ala Asp Gly Ser Val Lys
                245                 250

<210> SEQ ID NO 49
<211> LENGTH: 627
<212> TYPE: DNA
<213> ORGANISM: Artificial Sequence
<220> FEATURE:
<223> OTHER INFORMATION: Synthetic

<400> SEQUENCE: 49
atgagtgaga tgataacaag acaacaggta acaagtggcg agaccattca tgtgagaact      60
gatcctactg catgtatagg atctcatcct aattgtagat tatttattga ttctttaact     120
atagctgggg agaaacttga taaaaatatc gttgctatag atggtggaga ggatgtcacg     180
aaagctgatt cggctacagc tgctgctagt gtaatacgtt tatctataac gccaggctct     240
ataaatccaa caataagtat tactcttggt gttctaatta aatcaaatgt tagaactaaa     300
attgaagaga agtttcgag tatattacaa gcagtgctta cagatatgaa aattaagtta      360
ggtaattcta ataaaaaaca agagtataaa actgatgaag catggggtat tatgatagat     420
ctatctaatt tagagttata tccaataagt gctaaggctt ttagtattag tatagagcca     480
acagaactta tgggtgtttc aaaagatgga atgagatatc atattatatc tatagatggt     540
cttacaacat ctcaaggaag tttgccagta tgttgcgcag ctagcacaga taaggagtt      600 gctaaaatag gatatattgc agctgca                                         627

<210> SEQ ID NO 50
<211> LENGTH: 209
<212> TYPE: PRT
<213> ORGANISM: Artificial Sequence
<220> FEATURE:
<223> OTHER INFORMATION: Synthetic

<400> SEQUENCE: 50

Met Ser Glu Met Ile Thr Arg Gln Gln Val Thr Ser Gly Glu Thr Ile
1               5                   10                  15

His Val Arg Thr Asp Pro Thr Ala Cys Ile Gly Ser His Pro Asn Cys
            20                  25                  30

Arg Leu Phe Ile Asp Ser Leu Thr Ile Ala Gly Glu Lys Leu Asp Lys
        35                  40                  45

Asn Ile Val Ala Ile Asp Gly Gly Glu Asp Val Thr Lys Ala Asp Ser
    50                  55                  60

Ala Thr Ala Ala Ala Ser Val Ile Arg Leu Ser Ile Thr Pro Gly Ser
65                  70                  75                  80

Ile Asn Pro Thr Ile Ser Ile Thr Leu Gly Val Leu Ile Lys Ser Asn
                85                  90                  95

Val Arg Thr Lys Ile Glu Glu Lys Val Ser Ser Ile Leu Gln Ala Ser
            100                 105                 110

Ala Thr Asp Met Lys Ile Lys Leu Gly Asn Ser Asn Lys Lys Gln Glu
        115                 120                 125

Tyr Lys Thr Asp Glu Ala Trp Gly Ile Met Ile Asp Leu Ser Asn Leu
    130                 135                 140
```

Glu Leu Tyr Pro Ile Ser Ala Lys Ala Phe Ser Ile Ser Ile Glu Pro
145                 150                 155                 160

Thr Glu Leu Met Gly Val Ser Lys Asp Gly Met Arg Tyr His Ile Ile
            165                 170                 175

Ser Ile Asp Gly Leu Thr Thr Ser Gln Gly Ser Leu Pro Val Cys Cys
        180                 185                 190

Ala Ala Ser Thr Asp Lys Gly Val Ala Lys Ile Gly Tyr Ile Ala Ala
        195                 200                 205

Ala

<210> SEQ ID NO 51
<211> LENGTH: 1062
<212> TYPE: DNA
<213> ORGANISM: Artificial Sequence
<220> FEATURE:
<223> OTHER INFORMATION: Synthetic

<400> SEQUENCE: 51

| | | | | | |
|---|---|---|---|---|---|
| aaagaactaa | agtttgtaac | gttagtcttt | agacatggtg | atcgtagtcc | tattgatacc | 60 |
| tttcctacag | atccaatcaa | agagagtagt | tggccacaag | gcttcggaca | acttacacaa | 120 |
| ttaggaatgg | aacaacatta | tgaattaggt | gaatacattc | gcaaacgtta | tcgcaaattc | 180 |
| cttaatgaat | cgtacaaaca | cgaacaagtg | tatatccgtt | ccactgacgt | tgatagaaca | 240 |
| ctaatgtcag | ctatgacaaa | tctagctgca | ttagtgccac | cagaaggcgt | tagcatttgg | 300 |
| aatcctatct | tactttggca | gccaatacct | gtacatacgg | ttccgttatc | tgaagatcaa | 360 |
| ttactttatc | ttccatttcg | caactgccca | cgattccaag | aattagaatc | cgaaacattg | 420 |
| aaaagcgaag | aatttcagaa | aagattacat | ccatacaaag | actttatcgc | aaccttaggc | 480 |
| aaattgtcag | ggttacacgg | acaggatcta | tttggaattt | ggtcgaaagt | ttatgatcct | 540 |
| ttgtactgtg | aatctgtaca | taactttaca | ttacctagtc | gcgccacgga | agatactatg | 600 |
| acgaaactac | gtgaactttc | cgaactttct | ttactatcgt | tgtatggtat | tcataaacaa | 660 |
| aaagaaaaga | gcagattgca | aggtggtgtt | ttagtaaatg | aaatcttaaa | ccatatgaaa | 720 |
| agagctacac | aaattccgtc | ttacaagaaa | ttgattatgt | atagtgctca | tgatacgaca | 780 |
| gtatctgggc | ttcaaatggc | gttagatgtc | tataacggct | tacttccacc | gtatgcgtca | 840 |
| tgtcaccta | cggaacttta | ctttgagaaa | ggtgagtact | tgttgagat | gtactatcgc | 900 |
| aatgaaaccc | aacatgaacc | atatccgttg | atgttaccag | gttgtagtcc | atcttgcccg | 960 |
| ttagaacgat | ttgcggaatt | agtgggtcca | gtgataccac | aagactggtc | tactgagtgt | 1020 |
| atgactacta | atagccacca | agggactgaa | gattcaacag | at | | 1062 |

<210> SEQ ID NO 52
<211> LENGTH: 354
<212> TYPE: PRT
<213> ORGANISM: Artificial Sequence
<220> FEATURE:
<223> OTHER INFORMATION: Synthetic

<400> SEQUENCE: 52

Lys Glu Leu Lys Phe Val Thr Leu Val Phe Arg His Gly Asp Arg Ser
1               5                   10                  15

Pro Ile Asp Thr Phe Pro Thr Asp Pro Ile Lys Glu Ser Ser Trp Pro
            20                  25                  30

Gln Gly Phe Gly Gln Leu Thr Gln Leu Gly Met Glu Gln His Tyr Glu
        35                  40                  45

```
Leu Gly Glu Tyr Ile Arg Lys Arg Tyr Arg Lys Phe Leu Asn Glu Ser
 50                  55                  60

Tyr Lys His Glu Gln Val Tyr Ile Arg Ser Thr Asp Val Asp Arg Thr
 65                  70                  75                  80

Leu Met Ser Ala Met Thr Asn Leu Ala Ala Leu Val Pro Pro Glu Gly
                 85                  90                  95

Val Ser Ile Trp Asn Pro Ile Leu Leu Trp Gln Pro Ile Pro Val His
                100                 105                 110

Thr Val Pro Leu Ser Glu Asp Gln Leu Leu Tyr Leu Pro Phe Arg Asn
            115                 120                 125

Cys Pro Arg Phe Gln Glu Leu Glu Ser Glu Thr Leu Lys Ser Glu Glu
            130                 135                 140

Phe Gln Lys Arg Leu His Pro Tyr Lys Asp Phe Ile Ala Thr Leu Gly
145                 150                 155                 160

Lys Leu Ser Gly Leu His Gly Gln Asp Leu Phe Gly Ile Trp Ser Lys
                165                 170                 175

Val Tyr Asp Pro Leu Tyr Cys Glu Ser Val His Asn Phe Thr Leu Pro
            180                 185                 190

Ser Arg Ala Thr Glu Asp Thr Met Thr Lys Leu Arg Glu Leu Ser Glu
            195                 200                 205

Leu Ser Leu Leu Ser Leu Tyr Gly Ile His Lys Gln Lys Glu Lys Ser
210                 215                 220

Arg Leu Gln Gly Gly Val Leu Val Asn Glu Ile Leu Asn His Met Lys
225                 230                 235                 240

Arg Ala Thr Gln Ile Pro Ser Tyr Lys Lys Leu Ile Met Tyr Ser Ala
                245                 250                 255

His Asp Thr Thr Val Ser Gly Leu Gln Met Ala Leu Asp Val Tyr Asn
            260                 265                 270

Gly Leu Leu Pro Pro Tyr Ala Ser Cys His Leu Thr Glu Leu Tyr Phe
            275                 280                 285

Glu Lys Gly Glu Tyr Phe Val Glu Met Tyr Tyr Arg Asn Glu Thr Gln
290                 295                 300

His Glu Pro Tyr Pro Leu Met Leu Pro Gly Cys Ser Pro Ser Cys Pro
305                 310                 315                 320

Leu Glu Arg Phe Ala Glu Leu Val Gly Pro Val Ile Pro Gln Asp Trp
                325                 330                 335

Ser Thr Glu Cys Met Thr Thr Asn Ser His Gln Gly Thr Glu Asp Ser
            340                 345                 350

Thr Asp

<210> SEQ ID NO 53
<211> LENGTH: 1458
<212> TYPE: DNA
<213> ORGANISM: Artificial Sequence
<220> FEATURE:
<223> OTHER INFORMATION: Synthetic

<400> SEQUENCE: 53
ctgccactta gttatcaaca ttttcgcaaa cttttgttgc tcgacgatgg tactgaagct     60
gggccactag aagaagagct accacgtctt gcggatgcag acctcaatag acgtgtggcc    120
gaagatttga acttaggcaa tctaaacgta agtattccgt ggacacataa agttggcaat    180
ttcactggtc tgtattcaag tacgttcca atattcaatc cagaatggca aaccccatcg    240
tttcctaaaa tccatttaca agaagatatt attaatcgct gccaacagtt cgtcgggcca    300
```

-continued

```
ttaacagtca atgaaaagcg tcgcttgaaa ttgattatgc ctgcgcgttt ctatccaact      360
catacaaaat acttgccgct agataaaggc attaaacctt actatccaga tcaagtggtg      420
aatcactatt tcaaacccg ccattatctt catacactct ggaaagctgg tatcttgtat       480
aaacgagaga ctacgcgatc cgccagtttt tgtggatcac catatagctg ggaacaagaa      540
cttcaacatg gtagacttgt gattaagaca tcacaaagac atggagatga gagcttctgt      600
tctcaaccgt cgggtatatt gagtcgaagt agcgtcggtc catgtattcg tagccaactt      660
aaacaatctc gtctaggcct tcaaccacac caagggccac ttgcatccag ccaaccaggt      720
agatcaggct cgatcagagc aagagcccac ccgtctacgc gacgatactt tggtgtagaa      780
ccgtccggca gcggtcatat cgaccactcc gttaacaata gcagttcttg tctacaccag      840
tcagccgttc gtaaagcagc atactcacac ctatctactt caaaaagaca atcttcatcg      900
actagtatgg ccgctcgttt atactgccaa ctagacccaa gtcgggatgt gctatgtttg      960
cgtccagttg gtgccgagag ccgtggtaga ccattatccg gacctttagg aacgttaagt     1020
tctccatcac cgtccgctgt accagctgat catggggcac atttatcatt acgcggttta     1080
ccagtttgcg catttctttc ggctggacca tgcgcacttc gctttacctc agcgcgatgt     1140
atggaaacga cagttaacgc gcatcaaatc cttccgaaag ttttgcacaa acgtacatta     1200
ggccttccag ctatgagcac tacagattta gaagcatatt tcaaagattg tgtgtttaaa     1260
gactgggaag aattgggtga agaaattaga cttaaagtct ttgtactagg gggctgtaga     1320
cataagttag tatgcgcacc tgcgccttgt aatttctta catctgcaca attgggtgac      1380
ggtagtatta aacttagcaa agtattacaa ttagaaagta ttattaattt tgaaaaatta     1440
gctgatggtt cagttaaa                                                   1458
```

<210> SEQ ID NO 54
<211> LENGTH: 486
<212> TYPE: PRT
<213> ORGANISM: Artificial Sequence
<220> FEATURE:
<223> OTHER INFORMATION: Synthetic

<400> SEQUENCE: 54

```
Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
            20                  25                  30

Ala Asp Leu Asn Arg Arg Val Ala Glu Asp Leu Asn Leu Gly Asn Leu
        35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
            100                 105                 110

Met Pro Ala Arg Phe Tyr Pro Thr His Thr Lys Tyr Leu Pro Leu Asp
        115                 120                 125

Lys Gly Ile Lys Pro Tyr Tyr Pro Asp Gln Val Val Asn His Tyr Phe
    130                 135                 140

Gln Thr Arg His Tyr Leu His Thr Leu Trp Lys Ala Gly Ile Leu Tyr
```

145                 150                 155                 160
Lys Arg Glu Thr Thr Arg Ser Ala Ser Phe Cys Gly Ser Pro Tyr Ser
                165                 170                 175

Trp Gln Glu Leu Gln His Gly Arg Leu Val Ile Lys Thr Ser Gln
            180                 185                 190

Arg His Gly Asp Glu Ser Phe Cys Ser Gln Pro Ser Gly Ile Leu Ser
                195                 200                 205

Arg Ser Ser Val Gly Pro Cys Ile Arg Ser Gln Leu Lys Gln Ser Arg
210                 215                 220

Leu Gly Leu Gln Pro His Gln Gly Pro Leu Ala Ser Ser Gln Pro Gly
225                 230                 235                 240

Arg Ser Gly Ser Ile Arg Ala Arg Ala His Pro Ser Thr Arg Arg Tyr
                245                 250                 255

Phe Gly Val Glu Pro Ser Gly Ser Gly His Ile Asp His Ser Val Asn
                260                 265                 270

Asn Ser Ser Ser Cys Leu His Gln Ser Ala Val Arg Lys Ala Ala Tyr
                275                 280                 285

Ser His Leu Ser Thr Ser Lys Arg Gln Ser Ser Ser Thr Ser Met Ala
            290                 295                 300

Ala Arg Leu Tyr Cys Gln Leu Asp Pro Ser Arg Asp Val Leu Cys Leu
305                 310                 315                 320

Arg Pro Val Gly Ala Glu Ser Arg Gly Arg Pro Leu Ser Gly Pro Leu
                325                 330                 335

Gly Thr Leu Ser Ser Pro Ser Pro Ser Ala Val Pro Ala Asp His Gly
                340                 345                 350

Ala His Leu Ser Leu Arg Gly Leu Pro Val Cys Ala Phe Ser Ser Ala
            355                 360                 365

Gly Pro Cys Ala Leu Arg Phe Thr Ser Ala Arg Cys Met Glu Thr Thr
            370                 375                 380

Val Asn Ala His Gln Ile Leu Pro Lys Val Leu His Lys Arg Thr Leu
385                 390                 395                 400

Gly Leu Pro Ala Met Ser Thr Thr Asp Leu Glu Ala Tyr Phe Lys Asp
                405                 410                 415

Cys Val Phe Lys Asp Trp Glu Glu Leu Gly Glu Glu Ile Arg Leu Lys
                420                 425                 430

Val Phe Val Leu Gly Gly Cys Arg His Lys Leu Val Cys Ala Pro Ala
                435                 440                 445

Pro Cys Asn Phe Phe Thr Ser Ala Gln Leu Gly Asp Gly Ser Ile Lys
            450                 455                 460

Leu Ser Lys Val Leu Gln Leu Glu Ser Ile Ile Asn Phe Glu Lys Leu
465                 470                 475                 480

Ala Asp Gly Ser Val Lys
                485

<210> SEQ ID NO 55
<211> LENGTH: 1764
<212> TYPE: DNA
<213> ORGANISM: Artificial Sequence
<220> FEATURE:
<223> OTHER INFORMATION: Synthetic

<400> SEQUENCE: 55
cgtacattag caggtgaaac aggtcaagaa gcagcaccac ttgacggtgt attaacgaat     60
ccaccaaata tatcaagttt aagtccacgt caattattag gttttccatg tgcagaagtt    120

```
tcaggtttaa gtacagaacg tgtccgtgag ttagcagttg cattagcaca aaaaaacgtt    180
aaattatcta cagaacagtt acgttgttta gcccatagat taagcgaacc accagaagac    240
ttagatgcac ttcctttaga ccttctttta ttcttaaatc cagatgcatt ttcaggacca    300
caagcatgta cacgttttt tagtcgaatt acaaaagcca atgttgattt attacctcgt    360
ggggctcctg aaagacaacg tttattacct gctgcattag catgctgggg tgttcgcggt    420
agcttattaa gtgaagccga tgttcgtgct ttaggggtt tagcatgtga tttacctggt    480
cgtttcgttg cagaatcagc agaagtgtta ttaccgagat tagtttcatg cccaggacct    540
ttagatcaag atcaacaaga ggcagctaga gcagctcttc aaggaggagg cccaccatat    600
ggcccaccaa gtacatggag tgtttctaca atggatgcgt taagaggttt attaccggtt    660
ttaggacaac caattattcg tagtattcca caaggcattg tagcagcatg gcgtcaacgt    720
agttctcgtg atccgtcttg gcgacaacca gaacgtacaa ttctacgtcc aagatttcgt    780
agagaagtag aaaaaacggc gtgtcctagt ggcaaaaaag cacgtgaaat tgatgaaagt    840
ttaattttt ataaaaaatg ggaattagaa gcatgtgtcg atgcagcatt actagctaca    900
caaatggatc gtgttaatgc tattccattc acatatgaac aattagatgt tttaaagcat    960
aaattagacg aattatatcc acaaggttat ccagaatcag ttattcaaca tttaggttac   1020
ttatttttaa aaatgagtcc agaagacata cgcaaatgga atgttacaag tttagaaaca   1080
ttaaaagcgc ttttagaagt taacaaaggt catgaaatga gtccacaagt tgctacgtta   1140
attgatagat tcgttaaagg ccgtggtcaa ttagataaag atactttaga tacattaaca   1200
gcattttatc ctggctactt atgcagttta tcaccagaag aattaagttc cgttccaccg   1260
agtagtatct gggcagttcg tccgcaagat ttagatacat gcgacccacg tcaattagat   1320
gttttatatc caaaagcaag attagctttc caaaatatga acggtagtga atatttcgta   1380
aaaattcaat ccttttttagg tggtgcacca actgaagatc taaaagcatt aagccaacaa   1440
aatgtaagta tggatttagc tacgtttatg aaattacgta cagatgcagt tctaccatta   1500
acagttgcag aagttcaaaa attattaggt ccacacgtag aaggattaaa agcagaagaa   1560
cgtcaccgtc cagttcgcga ttggatttta cgtcaacgtc aagatgattt agatacatta   1620
ggtttaggtt tacaaggcgg tattccgaat ggatatttag tgttagattt atcggttcaa   1680
gaagcattaa gtggtacacc gtgtttatta ggtccaggtc cagttttaac agtgttagca   1740
ttattattag ccagtacatt agct                                           1764
```

<210> SEQ ID NO 56
<211> LENGTH: 588
<212> TYPE: PRT
<213> ORGANISM: Artificial Sequence
<220> FEATURE:
<223> OTHER INFORMATION: Synthetic

<400> SEQUENCE: 56

Arg Thr Leu Ala Gly Glu Thr Gly Gln Glu Ala Pro Leu Asp Gly
1               5                   10                  15

Val Leu Thr Asn Pro Pro Asn Ile Ser Ser Leu Ser Pro Arg Gln Leu
            20                  25                  30

Leu Gly Phe Pro Cys Ala Glu Val Ser Gly Leu Ser Thr Glu Arg Val
        35                  40                  45

Arg Glu Leu Ala Val Ala Leu Ala Gln Lys Asn Val Lys Leu Ser Thr
    50                  55                  60

Glu Gln Leu Arg Cys Leu Ala His Arg Leu Ser Glu Pro Pro Glu Asp

```
                65                  70                  75                  80
Leu Asp Ala Leu Pro Leu Asp Leu Leu Phe Leu Asn Pro Asp Ala
                        85                  90                  95
Phe Ser Gly Pro Gln Ala Cys Thr Arg Phe Phe Ser Arg Ile Thr Lys
                        100                 105                 110
Ala Asn Val Asp Leu Leu Pro Arg Gly Ala Pro Glu Arg Gln Arg Leu
                        115                 120                 125
Leu Pro Ala Ala Leu Ala Cys Trp Gly Val Arg Gly Ser Leu Leu Ser
130                     135                 140
Glu Ala Asp Val Arg Ala Leu Gly Gly Leu Ala Cys Asp Leu Pro Gly
145                     150                 155                 160
Arg Phe Val Ala Glu Ser Ala Glu Val Leu Leu Pro Arg Leu Val Ser
                        165                 170                 175
Cys Pro Gly Pro Leu Asp Gln Asp Gln Gln Glu Ala Ala Arg Ala Ala
                        180                 185                 190
Leu Gln Gly Gly Gly Pro Pro Tyr Gly Pro Pro Ser Thr Trp Ser Val
                        195                 200                 205
Ser Thr Met Asp Ala Leu Arg Gly Leu Leu Pro Val Leu Gly Gln Pro
    210                 215                 220
Ile Ile Arg Ser Ile Pro Gln Gly Ile Val Ala Ala Trp Arg Gln Arg
225                     230                 235                 240
Ser Ser Arg Asp Pro Ser Trp Arg Gln Pro Glu Arg Thr Ile Leu Arg
                        245                 250                 255
Pro Arg Phe Arg Arg Glu Val Glu Lys Thr Ala Cys Pro Ser Gly Lys
                        260                 265                 270
Lys Ala Arg Glu Ile Asp Glu Ser Leu Ile Phe Tyr Lys Lys Trp Glu
                        275                 280                 285
Leu Glu Ala Cys Val Asp Ala Ala Leu Leu Ala Thr Gln Met Asp Arg
                        290                 295                 300
Val Asn Ala Ile Pro Phe Thr Tyr Glu Gln Leu Asp Val Leu Lys His
305                     310                 315                 320
Lys Leu Asp Glu Leu Tyr Pro Gln Gly Tyr Pro Glu Ser Val Ile Gln
                        325                 330                 335
His Leu Gly Tyr Leu Phe Leu Lys Met Ser Pro Glu Asp Ile Arg Lys
                        340                 345                 350
Trp Asn Val Thr Ser Leu Glu Thr Leu Lys Ala Leu Leu Glu Val Asn
                        355                 360                 365
Lys Gly His Glu Met Ser Pro Gln Val Ala Thr Leu Ile Asp Arg Phe
    370                 375                 380
Val Lys Gly Arg Gly Gln Leu Asp Lys Asp Thr Leu Asp Thr Leu Thr
385                     390                 395                 400
Ala Phe Tyr Pro Gly Tyr Leu Cys Ser Leu Ser Pro Glu Glu Leu Ser
                        405                 410                 415
Ser Val Pro Pro Ser Ser Ile Trp Ala Val Arg Pro Gln Asp Leu Asp
                        420                 425                 430
Thr Cys Asp Pro Arg Gln Leu Asp Val Leu Tyr Pro Lys Ala Arg Leu
                        435                 440                 445
Ala Phe Gln Asn Met Asn Gly Ser Glu Tyr Phe Val Lys Ile Gln Ser
                        450                 455                 460
Phe Leu Gly Gly Ala Pro Thr Glu Asp Leu Lys Ala Leu Ser Gln Gln
465                     470                 475                 480
Asn Val Ser Met Asp Leu Ala Thr Phe Met Lys Leu Arg Thr Asp Ala
                        485                 490                 495
```

```
Val Leu Pro Leu Thr Val Ala Glu Val Gln Lys Leu Leu Gly Pro His
            500                 505                 510

Val Glu Gly Leu Lys Ala Glu Glu Arg His Arg Pro Val Arg Asp Trp
            515                 520                 525

Ile Leu Arg Gln Arg Gln Asp Asp Leu Asp Thr Leu Gly Leu Gly Leu
            530                 535                 540

Gln Gly Gly Ile Pro Asn Gly Tyr Leu Val Leu Asp Leu Ser Val Gln
545                 550                 555                 560

Glu Ala Leu Ser Gly Thr Pro Cys Leu Leu Gly Pro Gly Pro Val Leu
                565                 570                 575

Thr Val Leu Ala Leu Leu Leu Ala Ser Thr Leu Ala
            580                 585
```

<210> SEQ ID NO 57
<211> LENGTH: 1725
<212> TYPE: DNA
<213> ORGANISM: Artificial Sequence
<220> FEATURE:
<223> OTHER INFORMATION: Synthetic

<400> SEQUENCE: 57

```
cgtacattag caggtgaaac aggtcaagaa gcagcaccac ttgacggtgt attaacgaat      60
ccaccaaata tatcaagttt aagtccacgt caattattag gttttccatg tgcagaagtt     120
tcaggtttaa gtacagaacg tgtccgtgag ttagcagttg cattagcaca aaaaaacgtt     180
aaattatcta cagaacagtt acgttgttta gcccatagat taagcgaacc accagaagac     240
ttagatgcac ttcctttaga ccttctttta ttcttaaatc cagatgcatt ttcaggacca     300
caagcatgta cacgtttttt tagtcgaatt acaaaagcca atgttgattt attacctcgt     360
ggggctcctg aaagacaacg tttattacct gctgcattag catgctgggg tgttcgcggt     420
agcttattaa gtgaagccga tgttcgtgct ttagggggtt tagcatgtga tttacctggt     480
cgtttcgttg cagaatcagc agaagtgtta ttaccgagat tagtttcatg cccaggacct     540
ttagatcaag atcaacaaga ggcagctaga gcagctcttc aaggaggagg cccaccatat     600
ggcccaccaa gtacatggag tgtttctaca atggatgcgt taagaggttt attaccggtt     660
ttaggacaac caattattcg tagtattcca caaggcattg tagcagcatg gcgtcaacgt     720
agttctcgtg atccgtcttg gcgacaacca gaacgtacaa ttctacgtcc aagatttcgt     780
agagaagtag aaaaaacggc gtgtcctagt ggcaaaaaag cacgtgaaat tgatgaaagt     840
ttaatttttt ataaaaaatg ggaattagaa gcatgtgtcg atgcagcatt actagctaca     900
caaatggatc gtgttaatgc tattccattc acatatgaac aattagatgt tttaaagcat     960
aaattagacg aattatatcc acaaggttat ccagaatcag ttattcaaca tttaggttac    1020
ttattttaa aaatgagtcc agaagacata cgcaaatgga atgttacaag tttagaaaca    1080
ttaaaagcgc ttttagaagt taacaaaggt catgaaatga gtccacaagt tgctacgtta    1140
attgatagat tcgttaaagg ccgtggtcaa ttagataaag atactttaga tacattaaca    1200
gcattttatc ctggctactt atgcagttta tcaccagaag aattaagttc cgttccaccg    1260
agtagtatct gggcagttcg tccgcaagat ttagatacat gcgacccacg tcaattagat    1320
gttttatatc aaaagcaag attagctttc aaaatatga acggtagtga atatttcgta    1380
aaaattcaat cctttttagg tggtgcacca actgaagatc taaaagcatt aagccaacaa    1440
aatgtaagta tggatttagc tacgtttatg aaattacgta cagatgcagt tctaccatta    1500
```

-continued

```
acagttgcag aagttcaaaa attattaggt ccacacgtag aaggattaaa agcagaagaa    1560
cgtcaccgtc cagttcgcga ttggatttta cgtcaacgtc aagatgattt agatacatta    1620
ggtttaggtt tacaaggcgg tattccgaat ggatatttag tgttagattt atcggttcaa    1680
gaagcattaa gtggtacacc gtgtttatta ggtccaggtc cagtt                    1725
```

<210> SEQ ID NO 58
<211> LENGTH: 575
<212> TYPE: PRT
<213> ORGANISM: Artificial Sequence
<220> FEATURE:
<223> OTHER INFORMATION: Synthetic

<400> SEQUENCE: 58

```
Arg Thr Leu Ala Gly Glu Thr Gly Gln Glu Ala Ala Pro Leu Asp Gly
1               5                   10                  15

Val Leu Thr Asn Pro Pro Asn Ile Ser Ser Leu Ser Pro Arg Gln Leu
            20                  25                  30

Leu Gly Phe Pro Cys Ala Glu Val Ser Gly Leu Ser Thr Glu Arg Val
        35                  40                  45

Arg Glu Leu Ala Val Ala Leu Ala Gln Lys Asn Val Lys Leu Ser Thr
    50                  55                  60

Glu Gln Leu Arg Cys Leu Ala His Arg Leu Ser Pro Pro Glu Asp
65                  70                  75                  80

Leu Asp Ala Leu Pro Leu Asp Leu Leu Leu Phe Leu Asn Pro Asp Ala
                85                  90                  95

Phe Ser Gly Pro Gln Ala Cys Thr Arg Phe Phe Ser Arg Ile Thr Lys
            100                 105                 110

Ala Asn Val Asp Leu Leu Pro Arg Gly Ala Pro Glu Arg Gln Arg Leu
        115                 120                 125

Leu Pro Ala Ala Leu Ala Cys Trp Gly Val Arg Gly Ser Leu Leu Ser
    130                 135                 140

Glu Ala Asp Val Arg Ala Leu Gly Gly Leu Ala Cys Asp Leu Pro Gly
145                 150                 155                 160

Arg Phe Val Ala Glu Ser Ala Glu Val Leu Leu Pro Arg Leu Val Ser
                165                 170                 175

Cys Pro Gly Pro Leu Asp Gln Asp Gln Gln Glu Ala Ala Arg Ala Ala
            180                 185                 190

Leu Gln Gly Gly Gly Pro Pro Tyr Gly Pro Pro Ser Thr Trp Ser Val
        195                 200                 205

Ser Thr Met Asp Ala Leu Arg Gly Leu Leu Pro Val Leu Gly Gln Pro
    210                 215                 220

Ile Ile Arg Ser Ile Pro Gln Gly Ile Val Ala Ala Trp Arg Gln Arg
225                 230                 235                 240

Ser Ser Arg Asp Pro Ser Trp Arg Gln Pro Glu Arg Thr Ile Leu Arg
                245                 250                 255

Pro Arg Phe Arg Arg Glu Val Glu Lys Thr Ala Cys Pro Ser Gly Lys
            260                 265                 270

Lys Ala Arg Glu Ile Asp Glu Ser Leu Ile Phe Tyr Lys Lys Trp Glu
        275                 280                 285

Leu Glu Ala Cys Val Asp Ala Ala Leu Leu Ala Thr Gln Met Asp Arg
    290                 295                 300

Val Asn Ala Ile Pro Phe Thr Tyr Glu Gln Leu Asp Val Leu Lys His
305                 310                 315                 320

Lys Leu Asp Glu Leu Tyr Pro Gln Gly Tyr Pro Glu Ser Val Ile Gln
```

```
                    325                 330                 335
His Leu Gly Tyr Leu Phe Leu Lys Met Ser Pro Glu Asp Ile Arg Lys
            340                 345                 350

Trp Asn Val Thr Ser Leu Glu Thr Leu Lys Ala Leu Leu Glu Val Asn
                355                 360                 365

Lys Gly His Glu Met Ser Pro Gln Val Ala Thr Leu Ile Asp Arg Phe
        370                 375                 380

Val Lys Gly Arg Gly Gln Leu Asp Lys Asp Thr Leu Asp Thr Leu Thr
385                 390                 395                 400

Ala Phe Tyr Pro Gly Tyr Leu Cys Ser Leu Ser Pro Glu Glu Leu Ser
                405                 410                 415

Ser Val Pro Pro Ser Ser Ile Trp Ala Val Arg Pro Gln Asp Leu Asp
                420                 425                 430

Thr Cys Asp Pro Arg Gln Leu Asp Val Leu Tyr Pro Lys Ala Arg Leu
            435                 440                 445

Ala Phe Gln Asn Met Asn Gly Ser Glu Tyr Phe Val Lys Ile Gln Ser
        450                 455                 460

Phe Leu Gly Gly Ala Pro Thr Glu Asp Leu Lys Ala Leu Ser Gln Gln
465                 470                 475                 480

Asn Val Ser Met Asp Leu Ala Thr Phe Met Lys Leu Arg Thr Asp Ala
                485                 490                 495

Val Leu Pro Leu Thr Val Ala Glu Val Gln Lys Leu Leu Gly Pro His
            500                 505                 510

Val Glu Gly Leu Lys Ala Glu Glu Arg His Arg Pro Val Arg Asp Trp
        515                 520                 525

Ile Leu Arg Gln Arg Gln Asp Asp Leu Asp Thr Leu Gly Leu Gly Leu
530                 535                 540

Gln Gly Gly Ile Pro Asn Gly Tyr Leu Val Leu Asp Leu Ser Val Gln
545                 550                 555                 560

Glu Ala Leu Ser Gly Thr Pro Cys Leu Leu Gly Pro Gly Pro Val
                565                 570                 575

<210> SEQ ID NO 59
<211> LENGTH: 1602
<212> TYPE: DNA
<213> ORGANISM: Artificial Sequence
<220> FEATURE:
<223> OTHER INFORMATION: Synthetic

<400> SEQUENCE: 59
atggaagata gtccacaagt tgtatctcaa ggcggaccac ttggagcaac ttcgattgga      60
gatcaaaatc tcggacaacc tgatccaaac gcaagtggtg ccagtagcac aacacaaaca     120
acgggatcga atttgaatga tcgggaattg ctactaaaac ttcaacaaca agtgcaacaa     180
ttacagggac aattacaaca actcaaagcg caaggtaacg gcggtggttt gcaaaatacg     240
tataatggat catctcaatt tactacatat tctagtaaag tagatggaaa caaaaatcct     300
cgaacattag gtgaaatggg gaatcgaaaa gacctttcgc aagcactaat tggcggccaa     360
acaagttctg atatcatggg caacgtgaat gcatctaact cgattatcaa tttagctagt     420
gaaccattag ggggtgtttt caatcaaaaa ggtggaattg atgttggtgg tgctccagcc     480
attacgacac aaggccaagt tacatactta ggatcatatt ccggaaataa cagtattccg     540
atcggccaga ttagcagcaa tcttttttgcg tctactttat tgggacaacg tgagaaattt     600
gatgactata gtgtattctt cggtgggttt atcgaagcag atgcgcaagc atggtttggg     660
```

```
agtgctgtaa ctaaagtcca aaacgcaggt caactttcat caaatggaca gaatatctac    720
ttaacatccg caaacttata ctttctatca aatcttggcc attatgtaac tgctcaattt    780
gattttgata cgaatgaatc tggttcattc agcaacctag atatttctcc attctttgtt    840
acggcaggtc gtaataagtt atcagttggc tcctatgggg gtggtggcac atggactagc    900
gggattacca aatttctatc accaaatcag gtaactaacg tcagtataga ctataaggat    960
caagtctgga cgcgaatat tgcagttttt ggaagtgatg atcgtcgcgc taacttttcc    1020
accggtttat tctatgcgga ctcatggact ccgaatctgg cagctggatt caatgttggc    1080
tatgttttca acattgctgg agcgggtaat tcaagcatag ctaattcact tgctaatcta    1140
aatagaagct ctgacaacgt aggtgcgctt aatgttgacg aaatcttac ttatgccata    1200 tgggatggtt ttctaaatct gggagctggg tgggcttcca ccactacaaa agaggatttc    1260
aataacaacg gtggtagtgt attagcaggc gcgtggtatg gagcattgaa ctatagcgca    1320
atcttaggtg gtagaaatac aaatttcggg gtgacatatg gtcaatcata taacgcagct    1380
gctattccca tggaaacggc gaatgcgagt cctacatttg gtcagacagc aagcggcatt    1440
aaacaacaac ttatctttag tgcgcaaaga gcttactttg atgacaatgt tctctttggg    1500
ccggaatacg cttaccagcg cttatacacg ggtgaacaca tgaatacgat tactcttgat    1560
atgtctgtgt atgttactag tcatcatcat catcatcact aa                       1602
```

<210> SEQ ID NO 60
<211> LENGTH: 533
<212> TYPE: PRT
<213> ORGANISM: Artificial Sequence
<220> FEATURE:
<223> OTHER INFORMATION: Synthetic

<400> SEQUENCE: 60

```
Met Glu Asp Ser Pro Gln Val Val Ser Gln Gly Gly Pro Leu Gly Ala
1               5                   10                  15

Thr Ser Ile Gly Asp Gln Asn Leu Gly Gln Pro Asp Pro Asn Ala Ser
            20                  25                  30

Gly Ala Ser Ser Thr Thr Gln Thr Thr Gly Ser Asn Leu Asn Asp Arg
        35                  40                  45

Glu Leu Leu Leu Lys Leu Gln Gln Val Gln Gln Leu Gln Gly Gln
    50                  55                  60

Leu Gln Gln Leu Lys Ala Gln Gly Asn Gly Gly Leu Gln Asn Thr
65                  70                  75                  80

Tyr Asn Gly Ser Ser Gln Phe Thr Thr Tyr Ser Ser Lys Val Asp Gly
                85                  90                  95

Asn Lys Asn Pro Arg Thr Leu Gly Gly Asn Gly Glu Ser Lys Asp Leu
            100                 105                 110

Ser Gln Ala Leu Ile Gly Gly Gln Thr Ser Ser Asp Ile Met Gly Asn
        115                 120                 125

Val Asn Ala Ser Asn Ser Ile Ile Asn Leu Ala Ser Glu Pro Leu Gly
    130                 135                 140

Gly Val Phe Asn Gln Lys Gly Gly Ile Asp Val Gly Gly Ala Pro Ala
145                 150                 155                 160

Ile Thr Thr Gln Gly Gln Val Thr Tyr Leu Gly Ser Tyr Ser Gly Asn
                165                 170                 175

Asn Ser Ile Pro Ile Gly Gln Ile Ser Ser Asn Leu Phe Ala Ser Thr
            180                 185                 190

Leu Leu Gly Gln Arg Glu Lys Phe Asp Asp Tyr Ser Val Phe Phe Gly
```

```
                195                 200                 205
Gly Phe Ile Glu Ala Asp Ala Gln Ala Trp Phe Gly Ser Ala Val Thr
210                 215                 220

Lys Val Gln Asn Ala Gly Gln Leu Ser Ser Asn Gly Gln Asn Ile Tyr
225                 230                 235                 240

Leu Thr Ser Ala Asn Leu Tyr Phe Leu Ser Asn Leu Gly His Tyr Val
                245                 250                 255

Thr Ala Gln Phe Asp Phe Asp Thr Asn Glu Ser Gly Ser Phe Ser Asn
            260                 265                 270

Leu Asp Ile Ser Pro Phe Phe Val Thr Ala Gly Arg Asn Lys Leu Ser
        275                 280                 285

Val Gly Ser Tyr Gly Gly Gly Thr Trp Thr Ser Gly Ile Thr Lys
290                 295                 300

Phe Leu Ser Pro Asn Gln Val Thr Asn Val Ser Ile Asp Tyr Lys Asp
305                 310                 315                 320

Gln Val Trp Asn Ala Asn Ile Ala Val Phe Gly Ser Asp Asp Arg Arg
                325                 330                 335

Ala Asn Phe Ser Thr Gly Leu Phe Tyr Ala Asp Ser Trp Thr Pro Asn
            340                 345                 350

Leu Ala Ala Gly Phe Asn Val Gly Tyr Val Phe Asn Ile Ala Gly Ala
        355                 360                 365

Gly Asn Ser Ser Ile Ala Asn Ser Leu Ala Asn Leu Asn Arg Ser Ser
370                 375                 380

Asp Asn Val Gly Ala Leu Asn Val Asp Gly Asn Leu Thr Tyr Ala Ile
385                 390                 395                 400

Trp Asp Gly Phe Leu Asn Leu Gly Ala Gly Trp Ala Ser Thr Thr Thr
                405                 410                 415

Lys Glu Asp Phe Asn Asn Asn Gly Gly Ser Val Leu Ala Gly Ala Trp
            420                 425                 430

Tyr Gly Ala Leu Asn Tyr Ser Ala Ile Leu Gly Gly Arg Asn Thr Asn
        435                 440                 445

Phe Gly Val Thr Tyr Gly Gln Ser Tyr Asn Ala Ala Ile Pro Met
450                 455                 460

Glu Thr Ala Asn Ala Ser Pro Thr Phe Gly Gln Thr Ala Ser Gly Ile
465                 470                 475                 480

Lys Gln Gln Leu Ile Phe Ser Ala Gln Arg Ala Tyr Phe Asp Asp Asn
                485                 490                 495

Val Leu Phe Gly Pro Glu Tyr Ala Tyr Gln Arg Leu Tyr Thr Gly Glu
            500                 505                 510

His Met Asn Thr Ile Thr Leu Asp Met Ser Val Tyr Val Thr Ser His
        515                 520                 525

His His His His
    530

<210> SEQ ID NO 61
<211> LENGTH: 1959
<212> TYPE: DNA
<213> ORGANISM: Artificial Sequence
<220> FEATURE:
<223> OTHER INFORMATION: Synthetic

<400> SEQUENCE: 61
atgggcagca gccatcatca tcatcatcac ggcagcggcc tggtgccgcg cggcagcgct      60
agcatgtcgg actcagaagt caatcaagaa gctaagccag aggtcaagcc agaagtcaag     120
```

```
cctgagactc acatcaattt aaaggtgtcc gatggatctt cagagatctt cttcaagatc      180
aaaaagacca ctcctttaag aaggctgatg gaagcgttcg ctaaaagaca gggtaaggaa      240
atggactcct taagattctt gtacgacggt attagaattc aagctgatca gaccccctgaa     300
gatttggaca tggaggataa cgatattatt gaggctcaca gagaacagac cggtggatcc      360
gaagatagtc cacaagttgt atctcaaggc ggaccacttg gagcaacttc gattggagat      420
caaaatctcg gacaacctga tccaaacgca agtggtgcca gtagcacaac acaaacaacg      480
ggatcgaatt tgaatgatcg ggaattgcta ctaaaacttc aacaacaagt gcaacaatta      540
cagggacaat tacaacaact caaagcgcaa ggtaacggcg gtggtttgca aaatacgtat      600
aatggatcat ctcaatttac tacatattct agtaaagtag atggaaacaa aaatcctcga      660
acattaggtg gaaatgggga atcgaaagac ctttcgcaag cactaattgg cggccaaaca      720
agttctgata tcatgggcaa cgtgaatgca tctaactcga ttatcaattt agctagtgaa      780
ccattagggg gtgttttcaa tcaaaaaggt ggaattgatg ttggtggtgc tccagccatt      840
acgacacaag gccaagttac atacttagga tcatattccg gaataacag tattccgatc        900
ggccagatta gcagcaatct ttttgcgtct actttattgg gacaacgtga gaaatttgat      960
gactatagtg tattcttcgg tgggtttatc gaagcagatg cgcaagcatg gtttgggagt     1020
gctgtaacta agtccaaaa cgcaggtcaa ctttcatcaa atggacagaa tatctactta      1080
acatccgcaa acttatactt tctatcaaat cttggccatt atgtaactgc tcaatttgat     1140
tttgatacga atgaatctgg ttcattcagc aacctagata tttctccatt ctttgttacg     1200
gcaggtcgta taagttatc agttggctcc tatgggggtg gtggcacatg gactagcggg       1260
attaccaaat ttctatcacc aaatcaggta actaacgtca gtatagacta aaggatcaa      1320
gtctggaacg cgaatattgc agtttttgga agtgatgatc gtcgcgctaa cttttccacc     1380
ggtttattct atgcggactc atggactccg aatctggcag ctggattcaa tgttggctat     1440
gttttcaaca ttgctggagc gggtaattca agcatagcta attcacttgc taatctaaat      1500
agaagctctg acaacgtagg tgcgcttaat gttgacggaa atcttactta tgccatatgg     1560
gatggttttc taaatctggg agctgggtgg gcttccacca ctacaaaaga ggatttcaat     1620
aacaacggtg gtagtgtatt agcaggcgcg tggtatggag cattgaacta tagcgcaatc      1680
ttaggtggta gaaatacaaa tttcggggtg acatatggtc aatcatataa cgcagctgct     1740
attcccatgg aaacggcgaa tgcgagtcct acatttggtc agacagcaag cggcattaaa     1800
caacaactta tctttagtgc gcaaagagct tactttgatg acaatgttct ctttgggccg     1860
gaatacgctt accagcgctt atacacgggt gaacacatga atacgattac tcttgatatg     1920
tctgtgtatg ttactagtca tcatcatcat catcactaa                            1959
```

<210> SEQ ID NO 62
<211> LENGTH: 652
<212> TYPE: PRT
<213> ORGANISM: Artificial Sequence
<220> FEATURE:
<223> OTHER INFORMATION: Synthetic

<400> SEQUENCE: 62

```
Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
```

```
              35                  40                  45
Val Ser Asp Gly Ser Ser Glu Ile Phe Phe Lys Ile Lys Lys Thr Thr
 50                  55                  60
Pro Leu Arg Arg Leu Met Glu Ala Phe Ala Lys Arg Gln Gly Lys Glu
 65                      70                  75                  80
Met Asp Ser Leu Arg Phe Leu Tyr Asp Gly Ile Arg Ile Gln Ala Asp
                     85                  90                  95
Gln Thr Pro Glu Asp Leu Asp Met Glu Asp Asn Asp Ile Ile Glu Ala
                100                 105                 110
His Arg Glu Gln Thr Gly Gly Ser Glu Asp Ser Pro Gln Val Val Ser
            115                 120                 125
Gln Gly Gly Pro Leu Gly Ala Thr Ser Ile Gly Asp Gln Asn Leu Gly
        130                 135                 140
Gln Pro Asp Pro Asn Ala Ser Gly Ala Ser Ser Thr Thr Gln Thr Thr
145                 150                 155                 160
Gly Ser Asn Leu Asn Asp Arg Glu Leu Leu Leu Lys Leu Gln Gln Gln
                165                 170                 175
Val Gln Gln Leu Gln Gly Gln Leu Gln Gln Leu Lys Ala Gln Gly Asn
                180                 185                 190
Gly Gly Gly Leu Gln Asn Thr Tyr Asn Gly Ser Ser Gln Phe Thr Thr
            195                 200                 205
Tyr Ser Ser Lys Val Asp Gly Asn Lys Asn Pro Arg Thr Leu Gly Gly
        210                 215                 220
Asn Gly Glu Ser Lys Asp Leu Ser Gln Ala Leu Ile Gly Gly Gln Thr
225                 230                 235                 240
Ser Ser Asp Ile Met Gly Asn Val Asn Ala Ser Asn Ser Ile Ile Asn
                245                 250                 255
Leu Ala Ser Glu Pro Leu Gly Gly Val Phe Asn Gln Lys Gly Gly Ile
                260                 265                 270
Asp Val Gly Gly Ala Pro Ala Ile Thr Thr Gln Gly Gln Val Thr Tyr
            275                 280                 285
Leu Gly Ser Tyr Ser Gly Asn Asn Ser Ile Pro Ile Gly Gln Ile Ser
        290                 295                 300
Ser Asn Leu Phe Ala Ser Thr Leu Leu Gly Gln Arg Glu Lys Phe Asp
305                 310                 315                 320
Asp Tyr Ser Val Phe Phe Gly Phe Ile Glu Ala Asp Ala Gln Ala
                325                 330                 335
Trp Phe Gly Ser Ala Val Thr Lys Val Gln Asn Ala Gly Gln Leu Ser
            340                 345                 350
Ser Asn Gly Gln Asn Ile Tyr Leu Thr Ser Ala Asn Leu Tyr Phe Leu
        355                 360                 365
Ser Asn Leu Gly His Tyr Val Thr Ala Gln Phe Asp Phe Asp Thr Asn
        370                 375                 380
Glu Ser Gly Ser Phe Ser Asn Leu Asp Ile Ser Pro Phe Phe Val Thr
385                 390                 395                 400
Ala Gly Arg Asn Lys Leu Ser Val Gly Ser Tyr Gly Gly Gly Thr
                405                 410                 415
Trp Thr Ser Gly Ile Thr Lys Phe Leu Ser Pro Asn Gln Val Thr Asn
            420                 425                 430
Val Ser Ile Asp Tyr Lys Asp Gln Val Trp Asn Ala Asn Ile Ala Val
        435                 440                 445
Phe Gly Ser Asp Asp Arg Arg Ala Asn Phe Ser Thr Gly Leu Phe Tyr
        450                 455                 460
```

Ala Asp Ser Trp Thr Pro Asn Leu Ala Ala Gly Phe Asn Val Gly Tyr
465                 470                 475                 480

Val Phe Asn Ile Ala Gly Ala Gly Asn Ser Ile Ala Asn Ser Leu
            485                 490                 495

Ala Asn Leu Asn Arg Ser Ser Asp Asn Val Gly Ala Leu Asn Val Asp
            500                 505                 510

Gly Asn Leu Thr Tyr Ala Ile Trp Asp Gly Phe Leu Asn Leu Gly Ala
            515                 520                 525

Gly Trp Ala Ser Thr Thr Lys Glu Asp Phe Asn Asn Asn Gly Gly
530                 535                 540

Ser Val Leu Ala Gly Ala Trp Tyr Gly Ala Leu Asn Tyr Ser Ala Ile
545                 550                 555                 560

Leu Gly Gly Arg Asn Thr Asn Phe Gly Val Thr Tyr Gly Gln Ser Tyr
            565                 570                 575

Asn Ala Ala Ala Ile Pro Met Glu Thr Ala Asn Ala Ser Pro Thr Phe
            580                 585                 590

Gly Gln Thr Ala Ser Gly Ile Lys Gln Gln Leu Ile Phe Ser Ala Gln
            595                 600                 605

Arg Ala Tyr Phe Asp Asp Asn Val Leu Phe Gly Pro Glu Tyr Ala Tyr
610                 615                 620

Gln Arg Leu Tyr Thr Gly Glu His Met Asn Thr Ile Thr Leu Asp Met
625                 630                 635                 640

Ser Val Tyr Val Thr Ser His His His His His
            645                 650

```
<210> SEQ ID NO 63
<211> LENGTH: 2154
<212> TYPE: DNA
<213> ORGANISM: Artificial Sequence
<220> FEATURE:
<223> OTHER INFORMATION: Synthetic

<400> SEQUENCE: 63
atgggcagca gccatcatca tcatcatcac ggcagcggcc tggtgccgcg cggcagcgct      60
agcgcaagca aagtattgga atctaatcaa agcgtagagg acaagcacaa tgagttcatg     120
ttgacggagt acggttcatg tgccgatggc tcagtaaaga ctagcgcgag caaagtggcc     180
gagtcaaatc agtctgttga ggacaaacat aatgagttca tgttaacgga gtatggtagc     240
tgtggagatg gttcaattaa attatcaaaa gtcttagaat ctaatcagag cgttgaggac     300
aagcataatg agttcatgtt gacggagtac ggttcatgtg ctgacggaag tgttaaagcg     360
tcgaaagtag ctgaatcaaa tcaatctgta gaggacaaac acaatgaatt tatgctaaca     420
gaatacggca gctgcggtga tggctcgatc aaattgtcaa aagttttaga atctaaccag     480
agcgttgaag ataagcacaa cgaatttatg ttaacggagt acggttcatg cgcggatggt     540
tccgttaaag gatccgaaga tagtccacaa gttgtatctc aaggcggacc acttggagca     600
acttcgattg gagatcaaaa tctcggacaa cctgatccaa acgcaagtgg tgccagtagc     660
acaacacaaa caacgggatc gaatttgaat gatcgggaat tgctactaaa acttcaacaa     720
caagtgcaac aattacaggg acaattacaa caactcaaag cgcaaggtaa cggcggtggt     780
ttgcaaaata cgtataatgg atcatctcaa tttactacat attctagtaa agtagatgga     840
aacaaaaatc ctcgaacatt aggtggaaat gggaatcga aagacctttc gcaagcacta     900
attggcggcc aaacaagttc tgatatcatg ggcaacgtga atgcatctaa ctcgattatc     960
```

```
aatttagcta gtgaaccatt aggggggtgtt ttcaatcaaa aaggtggaat tgatgttggt    1020
ggtgctccag ccattacgac acaaggccaa gttacatact taggatcata ttccggaaat    1080
aacagtattc cgatcggcca gattagcagc aatcttttg cgtctacttt attgggacaa     1140
cgtgagaaat ttgatgacta tagtgtattc ttcggtgggt ttatcgaagc agatgcgcaa    1200
gcatggtttg ggagtgctgt aactaaagtc caaaacgcag gtcaactttc atcaaatgga    1260
cagaatatct acttaacatc cgcaaactta tactttctat caaatcttgg ccattatgta    1320
actgctcaat tgattttga tacgaatgaa tctggttcat tcagcaacct agatatttct    1380
ccattctttg ttacggcagg tcgtaataag ttatcagttg gctcctatgg gggtggtggc    1440
acatggacta gcgggattac caaatttcta tcaccaaatc aggtaactaa cgtcagtata    1500
gactataagg atcaagtctg gaacgcgaat attgcagttt ttggaagtga tgatcgtcgc    1560
gctaactttt ccaccggttt attctatgcg gactcatgga ctccgaatct ggcagctgga    1620
ttcaatgttg gctatgtttt caacattgct ggagcgggta attcaagcat agctaattca    1680
cttgctaatc taaatagaag ctctgacaac gtaggtgcgc ttaatgttga cggaaatctt    1740
acttatgcca tatgggatgg ttttctaaat ctgggagctg gtgggcttc caccactaca     1800 aaagaggatt tcaataacaa cggtggtagt gtattagcag cgcgtggta tggagcattg     1860 aactatagcg caatcttagg tggtagaaat acaaatttcg gggtgacata tggtcaatca    1920
tataacgcag ctgctattcc catggaaacg gcgaatgcga gtcctacatt tggtcagaca    1980
gcaagcggca ttaaacaaca acttatcttt agtgcgcaaa gagcttactt tgatgacaat    2040
gttctctttg ggccggaata cgcttaccag cgcttataca cgggtgaaca catgaatacg    2100
attactcttg atatgtctgt gtatgttact agtcatcatc atcatcatca ctaa          2154
```

<210> SEQ ID NO 64
<211> LENGTH: 717
<212> TYPE: PRT
<213> ORGANISM: Artificial Sequence
<220> FEATURE:
<223> OTHER INFORMATION: Synthetic

<400> SEQUENCE: 64

```
Met Gly Ser Ser His His His His His Gly Ser Gly Leu Val Pro
1               5                   10                  15

Arg Gly Ser Ala Ser Ala Ser Lys Val Leu Glu Ser Asn Gln Ser Val
            20                  25                  30

Glu Asp Lys His Asn Glu Phe Met Leu Thr Glu Tyr Gly Ser Cys Ala
        35                  40                  45

Asp Gly Ser Val Lys Thr Ser Ala Ser Lys Val Ala Glu Ser Asn Gln
    50                  55                  60

Ser Val Glu Asp Lys His Asn Glu Phe Met Leu Thr Glu Tyr Gly Ser
65                  70                  75                  80

Cys Gly Asp Gly Ser Ile Lys Leu Ser Lys Val Leu Glu Ser Asn Gln
                85                  90                  95

Ser Val Glu Asp Lys His Asn Glu Phe Met Leu Thr Glu Tyr Gly Ser
            100                 105                 110

Cys Ala Asp Gly Ser Val Lys Ala Ser Lys Val Ala Glu Ser Asn Gln
        115                 120                 125

Ser Val Glu Asp Lys His Asn Glu Phe Met Leu Thr Glu Tyr Gly Ser
    130                 135                 140

Cys Gly Asp Gly Ser Ile Lys Leu Ser Lys Val Leu Glu Ser Asn Gln
145                 150                 155                 160
```

-continued

```
Ser Val Glu Asp Lys His Asn Glu Phe Met Leu Thr Glu Tyr Gly Ser
                165                 170                 175

Cys Ala Asp Gly Ser Val Lys Gly Ser Glu Asp Ser Pro Gln Val Val
            180                 185                 190

Ser Gln Gly Gly Pro Leu Gly Ala Thr Ser Ile Gly Asp Gln Asn Leu
        195                 200                 205

Gly Gln Pro Asp Pro Asn Ala Ser Gly Ala Ser Ser Thr Thr Gln Thr
    210                 215                 220

Thr Gly Ser Asn Leu Asn Asp Arg Glu Leu Leu Leu Lys Leu Gln Gln
225                 230                 235                 240

Gln Val Gln Gln Leu Gln Gly Gln Leu Gln Gln Leu Lys Ala Gln Gly
                245                 250                 255

Asn Gly Gly Gly Leu Gln Asn Thr Tyr Asn Gly Ser Ser Gln Phe Thr
            260                 265                 270

Thr Tyr Ser Ser Lys Val Asp Gly Asn Lys Asn Pro Arg Thr Leu Gly
        275                 280                 285

Gly Asn Gly Glu Ser Lys Asp Leu Ser Gln Ala Leu Ile Gly Gly Gln
    290                 295                 300

Thr Ser Ser Asp Ile Met Gly Asn Val Asn Ala Ser Asn Ser Ile Ile
305                 310                 315                 320

Asn Leu Ala Ser Glu Pro Leu Gly Gly Val Phe Asn Gln Lys Gly Gly
                325                 330                 335

Ile Asp Val Gly Gly Ala Pro Ala Ile Thr Thr Gln Gly Gln Val Thr
            340                 345                 350

Tyr Leu Gly Ser Tyr Ser Gly Asn Ser Ile Pro Ile Gly Gln Ile
        355                 360                 365

Ser Ser Asn Leu Phe Ala Ser Thr Leu Leu Gly Gln Arg Glu Lys Phe
    370                 375                 380

Asp Asp Tyr Ser Val Phe Phe Gly Gly Phe Ile Glu Ala Asp Ala Gln
385                 390                 395                 400

Ala Trp Phe Gly Ser Ala Val Thr Lys Val Gln Asn Ala Gly Gln Leu
                405                 410                 415

Ser Ser Asn Gly Gln Asn Ile Tyr Leu Thr Ser Ala Asn Leu Tyr Phe
            420                 425                 430

Leu Ser Asn Leu Gly His Tyr Val Thr Ala Gln Phe Asp Phe Asp Thr
        435                 440                 445

Asn Glu Ser Gly Ser Phe Ser Asn Leu Asp Ile Ser Pro Phe Phe Val
    450                 455                 460

Thr Ala Gly Arg Asn Lys Leu Ser Val Gly Ser Tyr Gly Gly Gly Gly
465                 470                 475                 480

Thr Trp Thr Ser Gly Ile Thr Lys Phe Leu Ser Pro Asn Gln Val Thr
                485                 490                 495

Asn Val Ser Ile Asp Tyr Lys Asp Gln Val Trp Asn Ala Asn Ile Ala
            500                 505                 510

Val Phe Gly Ser Asp Asp Arg Arg Ala Asn Phe Ser Thr Gly Leu Phe
        515                 520                 525

Tyr Ala Asp Ser Trp Thr Pro Asn Leu Ala Ala Gly Phe Asn Val Gly
    530                 535                 540

Tyr Val Phe Asn Ile Ala Gly Ala Gly Asn Ser Ser Ile Ala Asn Ser
545                 550                 555                 560

Leu Ala Asn Leu Asn Arg Ser Ser Asp Asn Val Gly Ala Leu Asn Val
                565                 570                 575
```

```
Asp Gly Asn Leu Thr Tyr Ala Ile Trp Asp Gly Phe Leu Asn Leu Gly
            580                 585                 590

Ala Gly Trp Ala Ser Thr Thr Thr Lys Glu Asp Phe Asn Asn Asn Gly
            595                 600                 605

Gly Ser Val Leu Ala Gly Ala Trp Tyr Gly Ala Leu Asn Tyr Ser Ala
            610                 615                 620

Ile Leu Gly Gly Arg Asn Thr Asn Phe Gly Val Thr Tyr Gly Gln Ser
625                 630                 635                 640

Tyr Asn Ala Ala Ala Ile Pro Met Glu Thr Ala Asn Ala Ser Pro Thr
                    645                 650                 655

Phe Gly Gln Thr Ala Ser Gly Ile Lys Gln Gln Leu Ile Phe Ser Ala
            660                 665                 670

Gln Arg Ala Tyr Phe Asp Asp Asn Val Leu Phe Gly Pro Glu Tyr Ala
            675                 680                 685

Tyr Gln Arg Leu Tyr Thr Gly Glu His Met Asn Thr Ile Thr Leu Asp
            690                 695                 700

Met Ser Val Tyr Val Thr Ser His His His His His
705                 710                 715
```

```
<210> SEQ ID NO 65
<211> LENGTH: 5
<212> TYPE: PRT
<213> ORGANISM: Listeria monocytogenes

<400> SEQUENCE: 65

Asp Lys Ala Leu Thr
1               5

<210> SEQ ID NO 66
<211> LENGTH: 5
<212> TYPE: PRT
<213> ORGANISM: Bacillus subtillis

<400> SEQUENCE: 66

Val Gly Ala Phe Gly
1               5

<210> SEQ ID NO 67
<211> LENGTH: 19
<212> TYPE: PRT
<213> ORGANISM: Artificial Sequence
<220> FEATURE:
<223> OTHER INFORMATION: Synthetic

<400> SEQUENCE: 67

Lys Glu Asn Ser Ile Ser Ser Met Ala Pro Pro Ala Ser Pro Pro Ala
1               5                   10                  15

Ser Pro Lys

<210> SEQ ID NO 68

<400> SEQUENCE: 68

000

<210> SEQ ID NO 69
<211> LENGTH: 66
<212> TYPE: PRT
<213> ORGANISM: Artificial Sequence
<220> FEATURE:
<223> OTHER INFORMATION: Synthetic
```

-continued

```
<400> SEQUENCE: 69

Ala Ser Lys Val Leu Glu Ser Asn Gln Ser Val Glu Asp Lys His Asn
1               5                   10                  15

Glu Phe Met Leu Thr Glu Tyr Gly Ser Cys Ala Asp Gly Ser Val Lys
            20                  25                  30

Thr Ser Ala Ser Lys Val Ala Glu Ser Asn Gln Ser Val Glu Asp Lys
        35                  40                  45

His Asn Glu Phe Met Leu Thr Glu Tyr Gly Ser Cys Gly Asp Gly Ser
    50                  55                  60

Ile Lys
65

<210> SEQ ID NO 70
<211> LENGTH: 66
<212> TYPE: PRT
<213> ORGANISM: Artificial Sequence
<220> FEATURE:
<223> OTHER INFORMATION: Synthetic

<400> SEQUENCE: 70

Ala Ser Lys Val Leu Pro Ala Ser Arg Ala Val Asp Asp His His Ala
1               5                   10                  15

Gln Phe Leu Leu Ser Glu Lys Gly Ser Cys Ala Asp Gly Ser Val Lys
            20                  25                  30

Thr Ser Ala Ser Lys Val Ala Pro Ala Ser Arg Ala Val Asp Asp His
        35                  40                  45

His Ala Gln Phe Leu Leu Ser Glu Lys Gly Ser Cys Gly Asp Gly Ser
    50                  55                  60

Ile Lys
65

<210> SEQ ID NO 71
<211> LENGTH: 98
<212> TYPE: PRT
<213> ORGANISM: Artificial Sequence
<220> FEATURE:
<223> OTHER INFORMATION: Synthetic

<400> SEQUENCE: 71

Ala Ser Lys Val Leu Glu Ser Asn Gln Ser Val Glu Asp Lys His Asn
1               5                   10                  15

Glu Phe Met Leu Thr Glu Tyr Gly Ser Cys Ala Asp Gly Ser Val Lys
            20                  25                  30

Thr Ser Ala Ser Lys Val Ala Glu Ser Asn Gln Ser Val Glu Asp Lys
        35                  40                  45

His Asn Glu Phe Met Leu Thr Glu Tyr Gly Ser Cys Gly Asp Gly Ser
    50                  55                  60

Ile Lys Leu Ser Lys Val Leu Glu Ser Asn Gln Ser Val Glu Asp Lys
65                  70                  75                  80

His Asn Glu Phe Met Leu Thr Glu Tyr Gly Ser Cys Ala Asp Gly Ser
                85                  90                  95

Val Lys

<210> SEQ ID NO 72
<211> LENGTH: 98
<212> TYPE: PRT
<213> ORGANISM: Artificial Sequence
<220> FEATURE:
<223> OTHER INFORMATION: Synthetic
```

```
<400> SEQUENCE: 72

Ala Ser Lys Val Leu Pro Ala Ser Arg Ala Val Asp Asp His His Ala
1               5                   10                  15

Gln Phe Leu Leu Ser Glu Lys Gly Ser Cys Ala Asp Gly Ser Val Lys
            20                  25                  30

Thr Ser Ala Ser Lys Val Ala Pro Ala Ser Arg Ala Val Asp Asp His
        35                  40                  45

His Ala Gln Phe Leu Leu Ser Glu Lys Gly Ser Cys Gly Asp Gly Ser
    50                  55                  60

Ile Lys Leu Ser Lys Val Leu Pro Ala Ser Arg Ala Val Asp Asp His
65                  70                  75                  80

His Ala Gln Phe Leu Leu Ser Glu Lys Gly Ser Cys Ala Asp Gly Ser
                85                  90                  95

Val Lys

<210> SEQ ID NO 73
<211> LENGTH: 130
<212> TYPE: PRT
<213> ORGANISM: Artificial Sequence
<220> FEATURE:
<223> OTHER INFORMATION: Synthetic

<400> SEQUENCE: 73

Ala Ser Lys Val Leu Glu Ser Asn Gln Ser Val Glu Asp Lys His Asn
1               5                   10                  15

Glu Phe Met Leu Thr Glu Tyr Gly Ser Cys Ala Asp Gly Ser Val Lys
            20                  25                  30

Thr Ser Ala Ser Lys Val Ala Glu Ser Asn Gln Ser Val Glu Asp Lys
        35                  40                  45

His Asn Glu Phe Met Leu Thr Glu Tyr Gly Ser Cys Gly Asp Gly Ser
    50                  55                  60

Ile Lys Leu Ser Lys Val Leu Glu Ser Asn Gln Ser Val Glu Asp Lys
65                  70                  75                  80

His Asn Glu Phe Met Leu Thr Glu Tyr Gly Ser Cys Ala Asp Gly Ser
                85                  90                  95

Val Lys Ala Ser Lys Val Ala Glu Ser Asn Gln Ser Val Glu Asp Lys
            100                 105                 110

His Asn Glu Phe Met Leu Thr Glu Tyr Gly Ser Cys Gly Asp Gly Ser
        115                 120                 125

Ile Lys
    130

<210> SEQ ID NO 74
<211> LENGTH: 130
<212> TYPE: PRT
<213> ORGANISM: Artificial Sequence
<220> FEATURE:
<223> OTHER INFORMATION: Synthetic

<400> SEQUENCE: 74

Ala Ser Lys Val Leu Pro Ala Ser Arg Ala Val Asp Asp His His Ala
1               5                   10                  15

Gln Phe Leu Leu Ser Glu Lys Gly Ser Cys Ala Asp Gly Ser Val Lys
            20                  25                  30

Thr Ser Ala Ser Lys Val Ala Pro Ala Ser Arg Ala Val Asp Asp His
        35                  40                  45
```

```
His Ala Gln Phe Leu Leu Ser Glu Lys Gly Ser Cys Gly Asp Gly Ser
    50                  55                  60

Ile Lys Leu Ser Lys Val Leu Pro Ala Ser Arg Ala Val Asp Asp His
65                  70                  75                  80

His Ala Gln Phe Leu Leu Ser Glu Lys Gly Ser Cys Ala Asp Gly Ser
                85                  90                  95

Val Lys Ala Ser Lys Val Ala Pro Ala Ser Arg Ala Val Asp Asp His
                100                 105                 110

His Ala Gln Phe Leu Leu Ser Glu Lys Gly Ser Cys Gly Asp Gly Ser
                115                 120                 125

Ile Lys
    130

<210> SEQ ID NO 75
<211> LENGTH: 6
<212> TYPE: PRT
<213> ORGANISM: Artificial Sequence
<220> FEATURE:
<223> OTHER INFORMATION: Synthetic

<400> SEQUENCE: 75

Lys Leu Ser Lys Val Leu
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic

<400> SEQUENCE: 76

Gly Asp Gly Asn Lys
1               5

<210> SEQ ID NO 77
<211> LENGTH: 18
<212> TYPE: PRT
<213> ORGANISM: Artificial Sequence
<220> FEATURE:
<223> OTHER INFORMATION: Synthetic

<400> SEQUENCE: 77

Ala Thr Asp Ser Glu Asp Ser Ser Leu Asn Thr Asp Glu Trp Glu Glu
1               5                   10                  15

Glu Lys
```